US009278222B2

(12) United States Patent
Thacker et al.

(10) Patent No.: US 9,278,222 B2
(45) Date of Patent: Mar. 8, 2016

(54) SYSTEM AND METHOD FOR CONVERTING TISSUE STIMULATION PROGRAMS IN A FORMAT USABLE BY AN ELECTRICAL CURRENT STEERING NAVIGATOR

(75) Inventors: James R. Thacker, Eureka, MO (US); Michael Moffitt, Valencia, CA (US); Kerry Bradley, Glendale, CA (US); David K. L. Peterson, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1581 days.

(21) Appl. No.: 12/501,282

(22) Filed: Jul. 10, 2009

(65) Prior Publication Data
US 2010/0010566 A1 Jan. 14, 2010

Related U.S. Application Data

(60) Provisional application No. 61/080,187, filed on Jul. 11, 2008.

(51) Int. Cl.
*A61N 1/36* (2006.01)
*A61N 1/372* (2006.01)
*G06F 19/00* (2011.01)

(52) U.S. Cl.
CPC .......... *A61N 1/37247* (2013.01); *A61N 1/3615* (2013.01); *A61N 1/36071* (2013.01); *A61N 1/36146* (2013.01); *A61N 1/36167* (2013.01); *A61N 1/36185* (2013.01); *A61N 1/37264* (2013.01); *G06F 19/3406* (2013.01)

(58) Field of Classification Search
USPC .................................. 607/2, 46, 59, 60, 117
See application file for complete search history.

(56) References Cited

U.S. PATENT DOCUMENTS 6,516,227 B1   2/2003   Meadows et al.
6,609,032 B1 *  8/2003   Woods et al. ................... 607/46
6,895,280 B2   5/2005   Meadows et al.

(Continued)

OTHER PUBLICATIONS

PCT International Preliminary Report on Patentability (Chapter I of the Patent Cooperation Treaty) for PCT/US2009/050309, Applicant: Boston Scientific Neuromodulation Corporation, Form PCT/IB/326 and 373, dated Jan. 30, 2011 (6 pages).

(Continued)

*Primary Examiner* — Eugene Wu
(74) *Attorney, Agent, or Firm* — Schwegman Lundberg & Woessner, P.A.

(57) ABSTRACT

A method, computer medium, and system for programming a controller is provided. The controller controls electrical stimulation energy output to electrodes, and stores a set of programmed stimulation parameters associated with the electrodes. The programmed stimulation parameter set is compared with sets of reference stimulation parameters, each of the reference sets of stimulation parameters being associated with the electrodes. If an identical match is determined between the programmed stimulation parameter set and any one of the reference stimulation parameter sets exists based on the comparison, the identically matched stimulation parameter set is selected as an initial stimulation parameter set. If an identical match does not exist, a best between the programmed stimulation parameter set and the reference stimulation parameter sets is determined and selected as the initial stimulation parameter set. The controller is then programmed with a new set of programmable stimulation parameters based on the initial stimulation parameter set.

5 Claims, 26 Drawing Sheets

(56) References Cited

U.S. PATENT DOCUMENTS

| | | | |
|---|---|---|---|
| 6,993,384 B2 | 1/2006 | Bradley et al. | |
| 7,819,909 B2 * | 10/2010 | Goetz et al. | 607/1 |
| 7,890,182 B2 * | 2/2011 | Parramon et al. | 607/70 |
| 2003/0139781 A1 | 7/2003 | Bradley et al. | |
| 2005/0245987 A1 * | 11/2005 | Woods et al. | 607/46 |
| 2007/0203542 A1 * | 8/2007 | Goetz et al. | 607/59 |
| 2007/0239228 A1 * | 10/2007 | Bradley | 607/59 |
| 2008/0114416 A1 | 5/2008 | Theriot et al. | |

OTHER PUBLICATIONS

PCT International Search Report for PCT/US2009/050309, Applicant: Boston Scientific Neuromodulation Corporation, Form PCT/ISA/210 and 220, dated Sep. 15, 2010 (7 pages).

PCT Written Opinion of the International Search Authority for PCT/US2009/050309, Applicant: Boston Scientific Neuromodulation Corporation, Form PCT/ISA/237, dated Sep. 15, 2010 (6 pages).

* cited by examiner

SYSTEM AND METHOD FOR CONVERTING TISSUE STIMULATION PROGRAMS IN A FORMAT USABLE BY AN ELECTRICAL CURRENT STEERING NAVIGATOR

RELATED APPLICATION

The present application claims the benefit under 35 U.S.C. §119 to U.S. provisional patent application Ser. No. 61/080,187, filed Jul. 11, 2008. The foregoing application is hereby incorporated by reference into the present application in its entirety.

FIELD OF THE INVENTION

The present invention relates to tissue stimulation systems, and more particularly, to a system and method for programming an implantable tissue stimulator.

BACKGROUND OF THE INVENTION

Spinal cord stimulation (SCS) is a well-accepted clinical method for reducing pain in certain populations of patients. Spinal cord stimulator and other implantable tissue stimulator systems come in two general types: radio-frequency (RF)-controlled and fully implanted. The type commonly referred to as an "RF" system includes an external RF transmitter inductively coupled via an electromagnetic link to an implanted receiver-stimulator connected to one or more leads with one or more electrodes for stimulating tissue. The power source, e.g., a battery, for powering the implanted receiver, as well as control circuitry to command the receiver-stimulator, is contained in the RF transmitter—a hand-held sized device typically worn on the patient's belt or carried in a pocket. Data/power signals are transcutaneously coupled from a cable-connected transmission coil connected to the RF transmitter and placed over the implanted receiver-stimulator. The implanted receiver-stimulator receives the signal and generates the stimulation. In contrast, the fully implanted type of stimulating system contains the control circuitry, as well as a power supply, e.g., a battery, all within an implantable pulse generator (IPG), so that once programmed and turned on, the IPG can operate independently of external hardware. The IPG is turned on and off and programmed to generate the desired stimulation pulses from an external portable programming device using transcutaneous electromagnetic or RF links.

In both the RF-controlled or fully implanted systems, the electrode leads are implanted along the dura of the spinal cord. Individual wires within one or more electrode leads connect with each electrode on the lead. The electrode leads exit the spinal column and attach to one or more electrode lead extensions, when necessary. The electrode leads or extensions are typically tunneled along the torso of the patient to a subcutaneous pocket where the receiver-stimulator or IPG is implanted. The RF transmitter or IPG can then be operated to generate electrical pulses that are delivered, through the electrodes, to the targeted tissue, and in particular, the dorsal column and dorsal root fibers within the spinal cord. The stimulation creates the sensation known as paresthesia, which can be characterized as an alternative sensation that replaces the pain signals sensed by the patient. Individual electrode contacts (the "electrodes") are arranged in a desired pattern and spacing in order to create an electrode array.

The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied in SCS include the amplitude, width, and rate of the electrical pulses provided through the electrode array. Each electrode combination, along with the electrical pulse parameters, can be referred to as a "stimulation parameter set".

Amplitude may be measured in milliamps, volts, etc., as appropriate, depending on whether the system provides stimulation from current sources or voltage sources. With some SCS systems, and in particular, SCS systems with independently controlled current or voltage sources, the distribution of the current to the electrodes (including the case of the receiver-stimulator or IPG, which may act as an electrode) may be varied such that the current is supplied via numerous different electrode configurations. In different configurations, the electrodes may provide current (or voltage) in different relative percentages of positive and negative current (or voltage) to create different fractionalized electrode configurations.

As briefly discussed above, an external control device, such as an RF controller or portable programming device, can be used to instruct the receiver-stimulator or IPG to generate electrical stimulation pulses in accordance with the selected stimulation parameters. Typically, the stimulation parameters programmed into the external device, itself, can be adjusted by manipulating controls on the external device itself to modify the electrical stimulation provided by the SCS system to the patient. However, the number of electrodes available, combined with the ability to generate a variety of complex stimulation pulses, presents a huge selection of stimulation parameter sets to the clinician or patient.

To facilitate such selection, the clinician generally programs the external control device, and if applicable the IPG, through a computerized programming system. This programming system can be a self-contained hardware/software system, or can be defined predominantly by software running on a standard personal computer (PC). The PC or custom hardware may actively control the characteristics of the electrical stimulation generated by the receiver-stimulator or IPG to allow the optimum stimulation parameters to be determined based on patient feedback and to subsequently program the RF transmitter or portable programming device with the optimum stimulation parameters. The computerized programming system may be operated by a clinician attending the patient in several scenarios.

For example, in order to achieve an effective result from SCS, the lead or leads must be placed in a location, such that the electrical stimulation will cause paresthesia. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When electrical leads are implanted within the patient, the computerized programming system, in the context of an operating room (OR) mapping procedure, may be used to instruct the RF transmitter or IPG to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the IPG, with a set of stimulation parameters that best addresses the painful site. Thus, the navigation session may be used to pinpoint the stimulation region or areas correlating to the pain. Such programming ability is particularly advantageous after implantation should the leads gradually or unexpectedly move, or in the case of a single-source system if the relative impedances of the contacts should change in a clinically significant way, thereby relocating the paresthesia away from the pain site. By reprogramming the external control device, the stimulation region can often be moved back to the effective pain site without having to reoperate on the patient in order to reposition the lead and its electrode array.

One known computerized programming system for SCS is called the Bionic Navigator®, available from Boston Scientific Neuromodulation, Valencia, Calif. The Bionic Navigator® is a software package that operates on a suitable PC and allows clinicians to program stimulation parameters into an external handheld programmer (referred to as a remote control). Each set of stimulation parameters, including fractionalized current distribution to the electrodes (as percentage cathodic current, percentage anodic current, or off), programmed by the Bionic Navigator® may be stored in both the Bionic Navigator® and the remote control and combined into a stimulation program that can then be used to stimulate multiple regions within the patient.

Prior to creating the stimulation programs, the Bionic Navigator® may be operated by a clinician in a "manual mode" to manually select the percentage cathodic current and percentage anodic current flowing through the electrodes, or may be operated by the clinician in a "navigation mode" to electrically "steer" the current along the implanted leads in real-time, thereby allowing the clinician to determine the most efficient stimulation parameter sets that can then be stored and eventually combined into stimulation programs. In the navigation mode, the Bionic Navigator® can store selected fractionalized electrode configurations that can be displayed to the clinician as marks representing corresponding stimulation regions relative to the electrode array.

The Bionic Navigator® performs current steering in accordance with a steering or navigation table. For example, as shown in Appendix A, an exemplary navigation table, which includes a series of reference electrode combinations (for a lead of 8 electrodes) with associated fractionalized current values (i.e., fractionalized electrode configurations), can be used to gradually steer electrical current from one basic electrode combination to the next, thereby electronically steering the stimulation region along the leads. The marks can then be created from selected fractionalized electrode configurations within the navigation table that can be combined with the electrical pulse parameters to create one or more stimulation programs.

For example, the navigation table can be used to gradually steer current between a basic electrode combination consisting of a cathodic electrode 3 and an anodic electrode 5 (represented by stimulation set 161) and either a basic electrode combination consisting of a cathodic electrode 3 and an anodic electrode 1 (represented by stimulation set 141) or a basic electrode combination consisting of a cathodic electrode 3 and an anodic electrode 6 (represented by stimulation set 181). That is, electrical current can be incrementally shifted from anodic electrode 5 to the anodic electrode 1 as one steps upward through the navigation table from stimulation set 161 to stimulation set 141, and from anodic electrode 5 to anodic electrode 6 as one steps downward through the navigation table from stimulation set 161 to stimulation set 181. The step size of the current should be small enough so that steering of the current does not result in discomfort to the patient, but should be large enough to allow refinement of a basic electrode combination in a reasonable amount of time.

Assuming, a current step size of 5% in the navigation table, there are literally billions of fractionalized electrode configurations that can be selected. However, due to memory and time constraints, only a limited number of fractionalized electrode configurations are stored within the navigation table. While this does not necessarily create an issue when the remote control is originally programmed by the Bionic Navigator®, if the remote control is to be reprogrammed; for example, if the patient returns to a physician's office to be refitted to improve the stimulation therapy provided by the IPG, the clinician may have to start the fitting from scratch when creating marks in the navigation mode.

In particular, while the remote control is capable of uploading the stimulation parameter sets to the Bionic Navigator® to aid in reprogramming the remote control, they may be different from any stimulation parameter sets that are capable of being generated using the navigation table due to the limited number of fractionalized electrode configurations within the navigation table; that is, the fractionalized electrode configurations currently stored in the remote control may not match any fractionalized electrode configurations stored in the navigation table because they were originally generated when the Bionic Navigator® was operated in the manual mode.

In any event, if the stimulation parameter sets uploaded from the remote control to the Bionic Navigator® do not identically match any stimulation parameter set corresponding to a fractionalized electrode configuration stored in the navigation table, it cannot be used as a starting point in reprogramming the remote control/IPG. As a result, the amount of time required to reprogram the remote control/IPG may be as long as the amount of time required to originally program the remote control/IPG with the Bionic Navigator®. Because programming the remote control can be quite complex, even when the Bionic Navigator® is operated in the navigation mode, the time lost as a result of having to reprogram the remote control/IPG from scratch, can be quite significant.

There, thus, remains a need for an improved method and system for reprogramming remote controls and other external devices used to control the electrical stimulation energy output by implantable devices.

SUMMARY OF THE INVENTION

In accordance with a first aspect of the present inventions, a method of programming a controller that controls electrical stimulation energy output to a plurality of electrodes. In one method, the controller is an external controller (e.g., a programming device or an RF transmitter) for controlling the stimulation energy output by an implantable device to the plurality of electrodes, although the controller could alternatively be an implantable device, such as an implantable pulse generator or receiver-stimulator. The controller stores a set of programmed stimulation parameters associated with the electrodes.

The method comprises comparing the programmed stimulation parameter set with a plurality of sets of reference stimulation parameters. Each of the reference sets of stimulation parameters is associated with the plurality of electrodes. One exemplary method comprises uploading the programmable stimulation parameter set from the controller to a computerized programming system that stores the reference stimulation parameter sets. In another exemplary method, the reference stimulation parameter sets are stored in a navigation table as a series of stimulation parameter sets.

The method comprises determining if an identical match between the programmed stimulation parameter set and any one of the reference stimulation parameter sets exists based on the comparison. If an identical match exists, the method comprises selecting the identically matched stimulation parameter set as an initial stimulation parameter set. If an identical match does not exist, the method comprises determining a best fit between the programmed stimulation parameter set and the reference stimulation parameter sets and selecting the best fit stimulation parameter set as the initial stimulation parameter set.

In one method, the best fit determination comprises prioritizing the electrodes (e.g., based on magnitudes of stimulation energy independently associated with the electrodes and/or polarities independently associated with the electrodes), and narrowing the reference stimulation parameter sets down to a single stimulation parameter set based on the electrode prioritization, wherein the single stimulation parameter set is selected as the initial stimulation parameter set. The narrowing step may, e.g., comprise initially determining a first set of the reference stimulation parameter sets that best match the programmable stimulation parameter set for the highest priority electrode, determining a next set of reference stimulation parameter sets from the first set of the reference stimulation parameter sets that best match the programmed stimulation parameter set for the next highest priority electrode, and repeating this step until the single stimulation parameter set remains.

In another method, the best fit determination comprises deriving a first set of data points from the programmed stimulation parameter set, and deriving a second set of data points from each of the reference stimulation parameter sets. Each data point in the first and second sets of data points may represent, e.g., a magnitude of stimulation energy associated with a respective one of the plurality of electrodes, or a voltage as a neural activation function of the plurality of electrodes. The best fit determination further comprises computationally comparing the first set of data points with each of the second sets of data points (e.g., using a comparison function selected from the group consisting of a correlation coefficient function, a least squares based function, and a cross-correlation function), and selecting one of the reference parameter sets as the initial stimulation parameter set based on the comparison. The data points associated with a subset or all of the electrodes may be compared.

The method further comprises programming the controller with a new set of programmable stimulation parameters based on the initial stimulation parameter set. An optional method comprises deriving an effective stimulation parameter set from the initial stimulation parameter set, wherein the effective stimulation parameter set is selected as the new programmable stimulation set. The derivation of the effective stimulation parameter set may, e.g., comprise gradually changing the initial stimulation parameter set to the effective stimulation parameter set while stimulating tissue (e.g., neural tissue, such as spinal cord tissue) of a patient in accordance with the gradually changing stimulation parameter set. For example, the initial stimulation parameter set may comprise a first electrical current values for a plurality of electrodes, the effective stimulation parameter set may comprise second electrical current values for the plurality of electrodes, in which case, the initial stimulation parameter set can be gradually changed to the effective stimulation parameter set by gradually shifting the first electrical current values to the second electrical current values. This shifting may occur with the pulses from both stimulation parameter sets being either simultaneous or interleaved in time. Each of the first and second electrical current values may be, e.g., fractionalized electrical current values.

In accordance with a second aspect of the present inventions, a computer readable medium for programming a controller that controls electrical stimulation energy output to a plurality of electrodes is provided. The controller stores a set of programmed stimulation parameters associated with the plurality of electrodes. The medium contains instructions, which when executed, comprise performing the steps described above.

In accordance with a third aspect of the present inventions, a tissue stimulation system is provided. The system comprises a plurality of electrodes configured for being placed in contact with tissue of a patient, an implantable device configured for conveying electrical stimulation energy to the plurality of electrodes, thereby creating a stimulation region in the tissue, an external controller configured for controlling the stimulation energy output by the implantable device to the plurality of electrodes in accordance with a set of programmed stimulation parameters, and a computerized programming system configured for performing the steps described above.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

Appendix A is an exemplary navigation table containing different fractionalized electrode combinations that can be used in a Spinal Cord Stimulation (SCS) system.

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
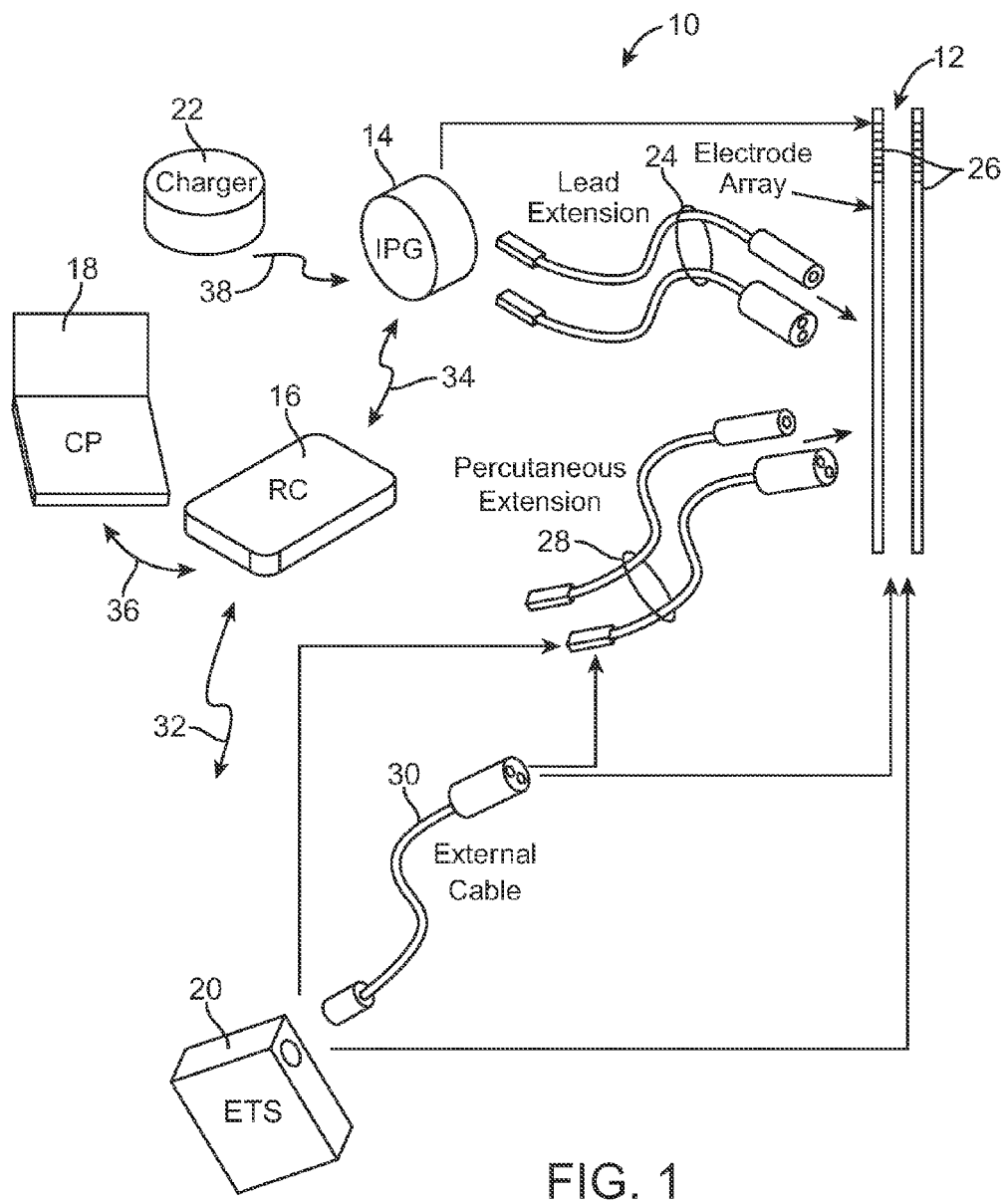
FIG. 1 is perspective view of one embodiment of a SCS system arranged in accordance with the present inventions.

Turning first to FIG. 1, an exemplary SCS system 10 generally includes one or more (in this case, two) implantable stimulation leads 12, an implantable pulse generator (IPG) 14, an external remote controller RC 16, a clinician's programmer (CP) 18, an External Trial Stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bidirectional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
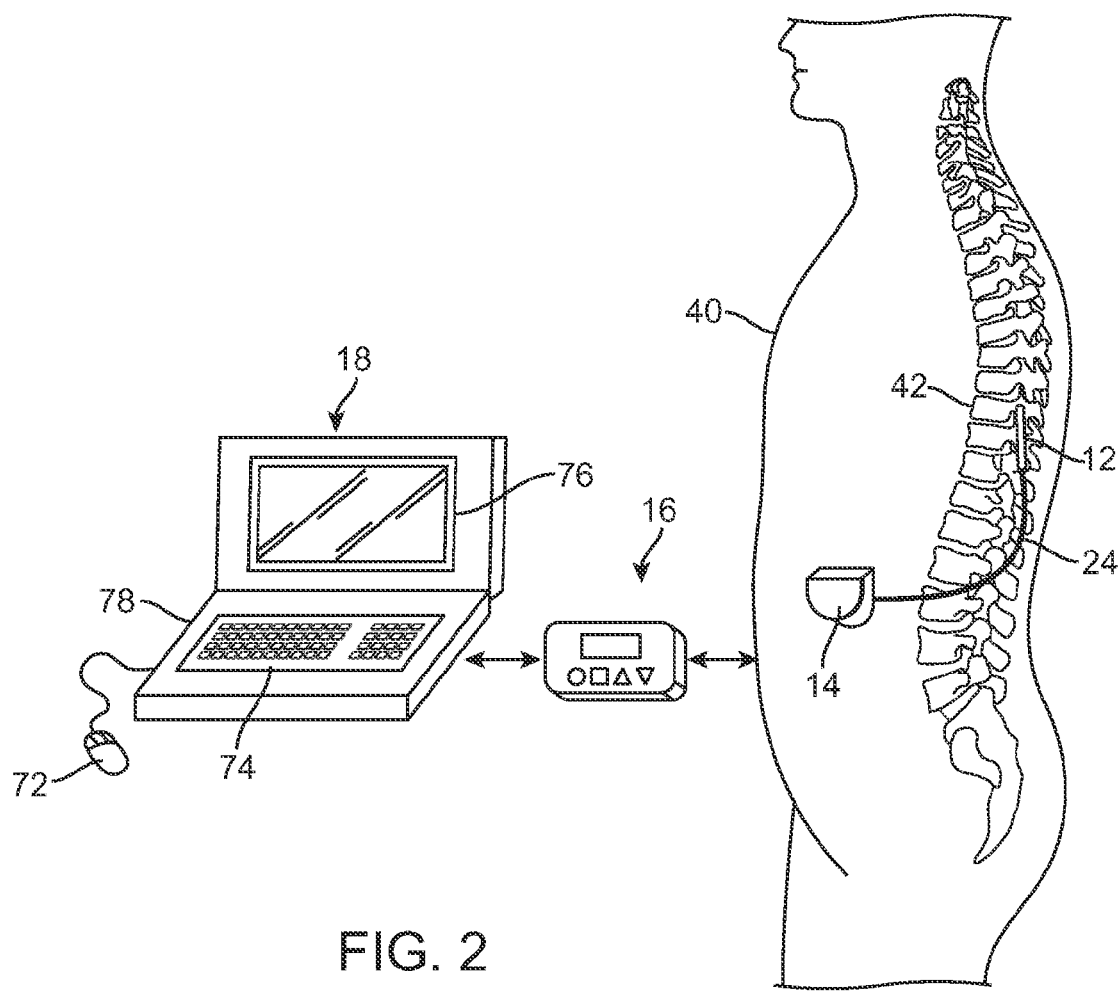
FIG. 2 is a plan view of the SCS system of FIG. 2 in use with a patient.

As shown in FIG. 2, the electrode leads 12 are implanted within the spinal column 42 of a patient 40. The preferred placement of the electrode leads 12 is adjacent, i.e., resting upon, the dura near the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

Figure 3:
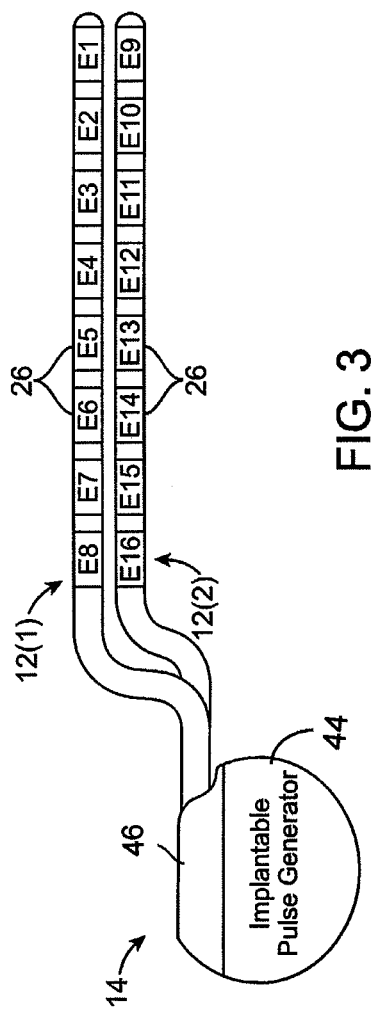
FIG. 3 is a side view of an implantable pulse generator and a pair of stimulation leads that can be used in the SCS system of FIG. 1.

Referring now to FIG. 3, the external features of the stimulation leads 12 and the IPG 14 will be briefly described. One of the stimulation leads 12 has eight electrodes 26 (labeled E1-E8), and the other stimulation lead 12 has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the stimulation leads 12 mates in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
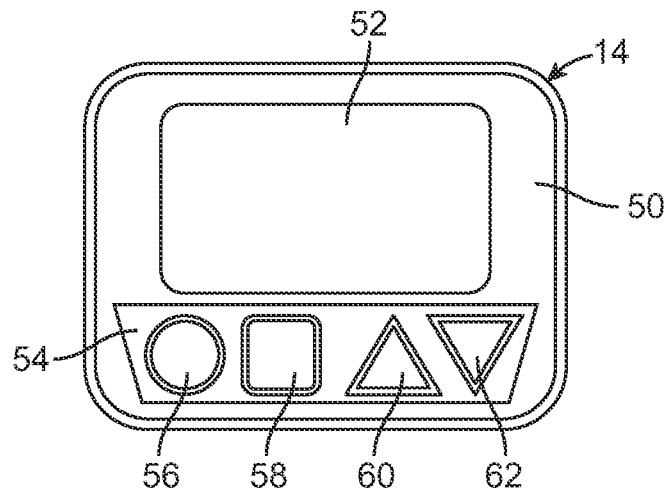
FIG. 4 is a plan view of a remote control that can be used in the SCS system of FIG. 1.

Referring now to FIG. 4, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touchscreen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can actuated to increment or decrement any of stimulation parameters of the pulse generated by the IPG 14, including pulse amplitude, pulse width, and pulse rate. For example, the selection button 58 can be actuated to place the RC 16 in an "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 5:
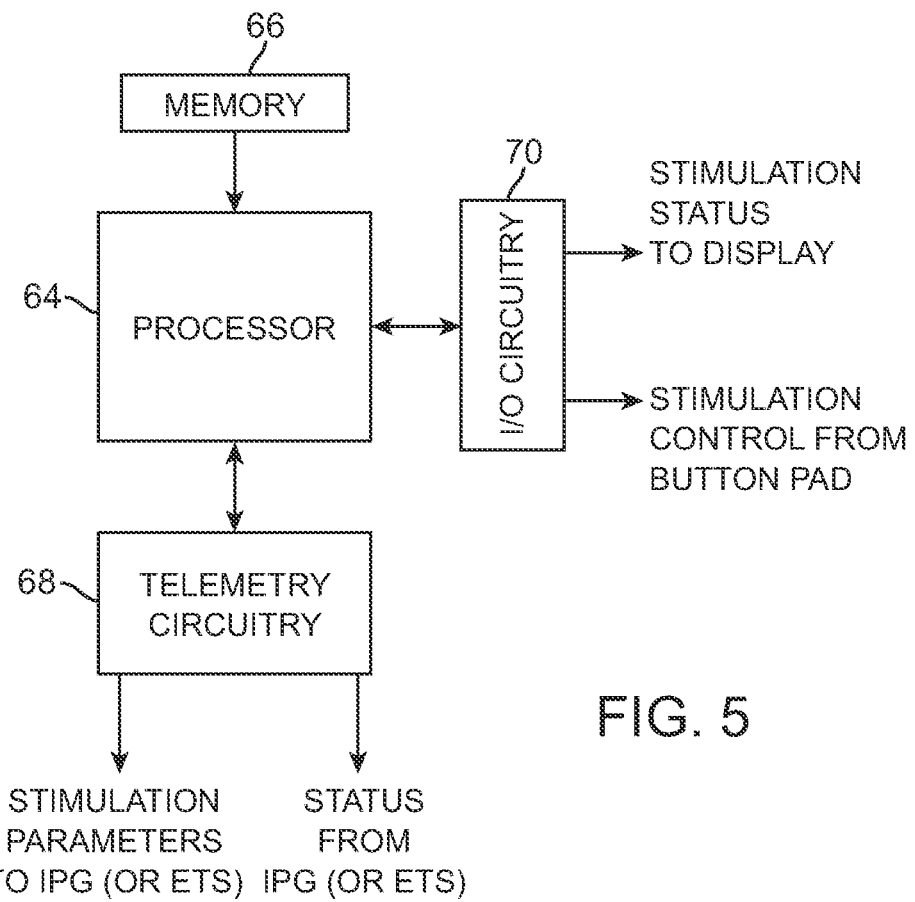
FIG. 5 is a block diagram of the internal componentry of the remote control of FIG. 4.

Referring to FIG. 5, the internal components of an exemplary RC 16 will now be described. The RC 16 generally includes a processor 64 (e.g., a microcontroller), memory 66 that stores an operating program for execution by the processor 64, as well as stimulation parameter sets in a look-up table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 4). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 (or EPS 20) via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 near the spinal cord.

As shown in FIG. 2, the overall appearance of the CP 18 is that of a laptop personal computer (PC), and in fact, may be implanted using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 (or ETS 20) to allow the optimum stimulation parameters to be determined based on patient feedback and for subsequently programming the IPG 14 (or ETS 20) with the optimum stimulation parameters.

Figure 6:
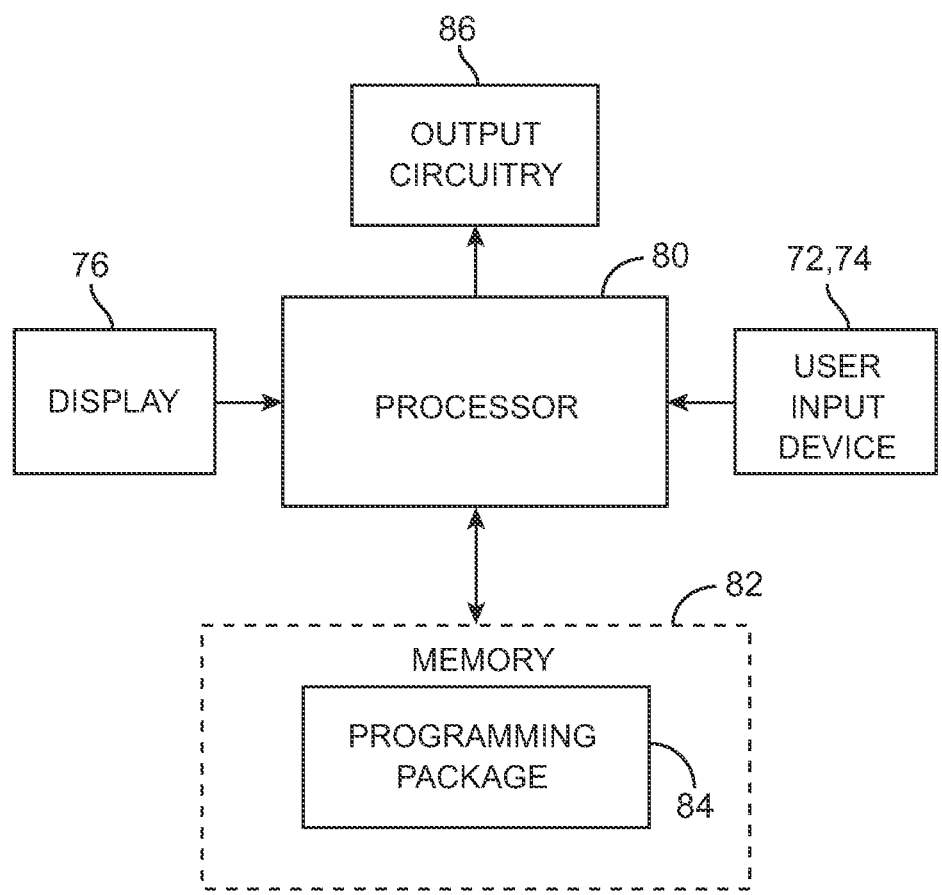
FIG. 6 is a block diagram of the components of a computerized programming system that can be used in the SCS system of FIG. 1.

To allow the clinician to perform these functions, the CP 18 includes a mouse 72, a keyboard 74, and a programming display screen 76 housed in a case 78. It is to be understood that in addition to, or in lieu of, the mouse 72, other directional programming devices may be used, such as a joystick, or directional keys included as part of the keys associated with the keyboard 74. As shown in FIG. 6, the CP 18 generally includes a processor 80 (e.g., a central processor unit (CPU)) and memory 82 that stores a stimulation programming package 84, which can be executed by the processor 80 to allow a clinician to program the IPG 14, and RC 16. The CP 18 further includes output circuitry 86 (e.g., via the telemetry circuitry of the RC 16) for downloading stimulation parameters to the IPG 14 and RC 16 and for uploading stimulation parameters already stored in the memory 66 of the RC 16, via the telemetry circuitry 68 of the RC 16.

Figure 7:
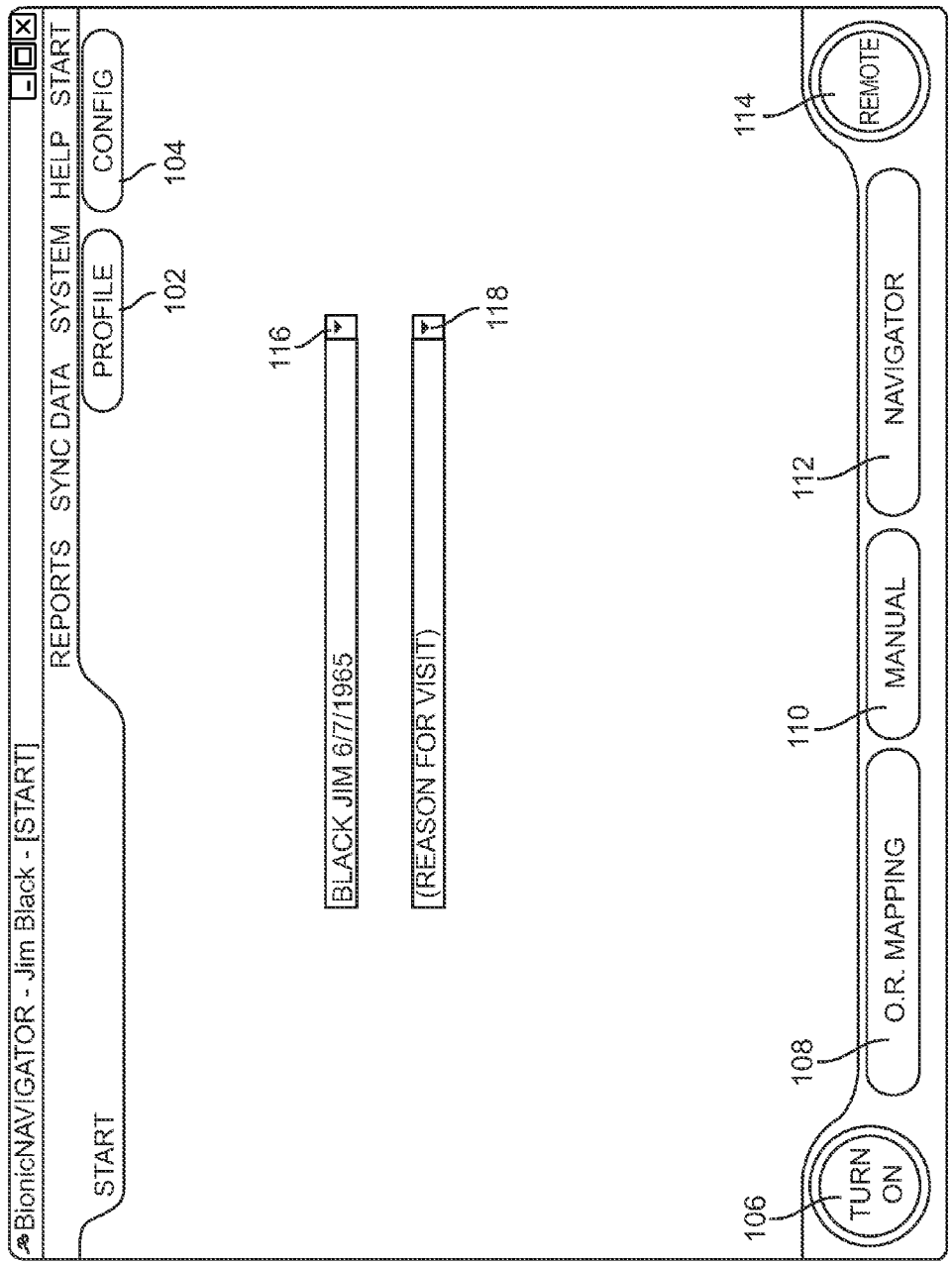
FIG. 7 is a start screen that can be displayed by the computerized programming system of FIG. 6.

Referring to FIGS. 7-24, execution of the programming package 84 by the processor 80 provides a multitude of display screens 100 that can be navigated through via use of the mouse 72. As shown, a profile button 102 and a configuration button 104 are located at the top of each of the display screens, and a power-on button 106, operating room button 108, manual button 110, navigator button 112, and remote button 114 are located at the bottom of each of the display screens 100. These buttons can be actuated, and in particular, clicked using the mouse 72, in order to perform various programming functions during the session. When the programming package 84 is initially executed, a start screen 100(1) is displayed to the clinician, as shown in FIG. 7. As there shown, the start screen 100(1) includes a patient pull down menu 116 that allows the clinician to select the specific patient profile or create a new patient profile, and a procedure pull down menu 118 that allows the clinician to select the specific procedure (e.g., programming/follow-up, implant trial system, implant IPG, implant IPG and lead(s), replace IPG, replace IPG and leads, replace or revise leads, explant, etc.).

Figure 8:
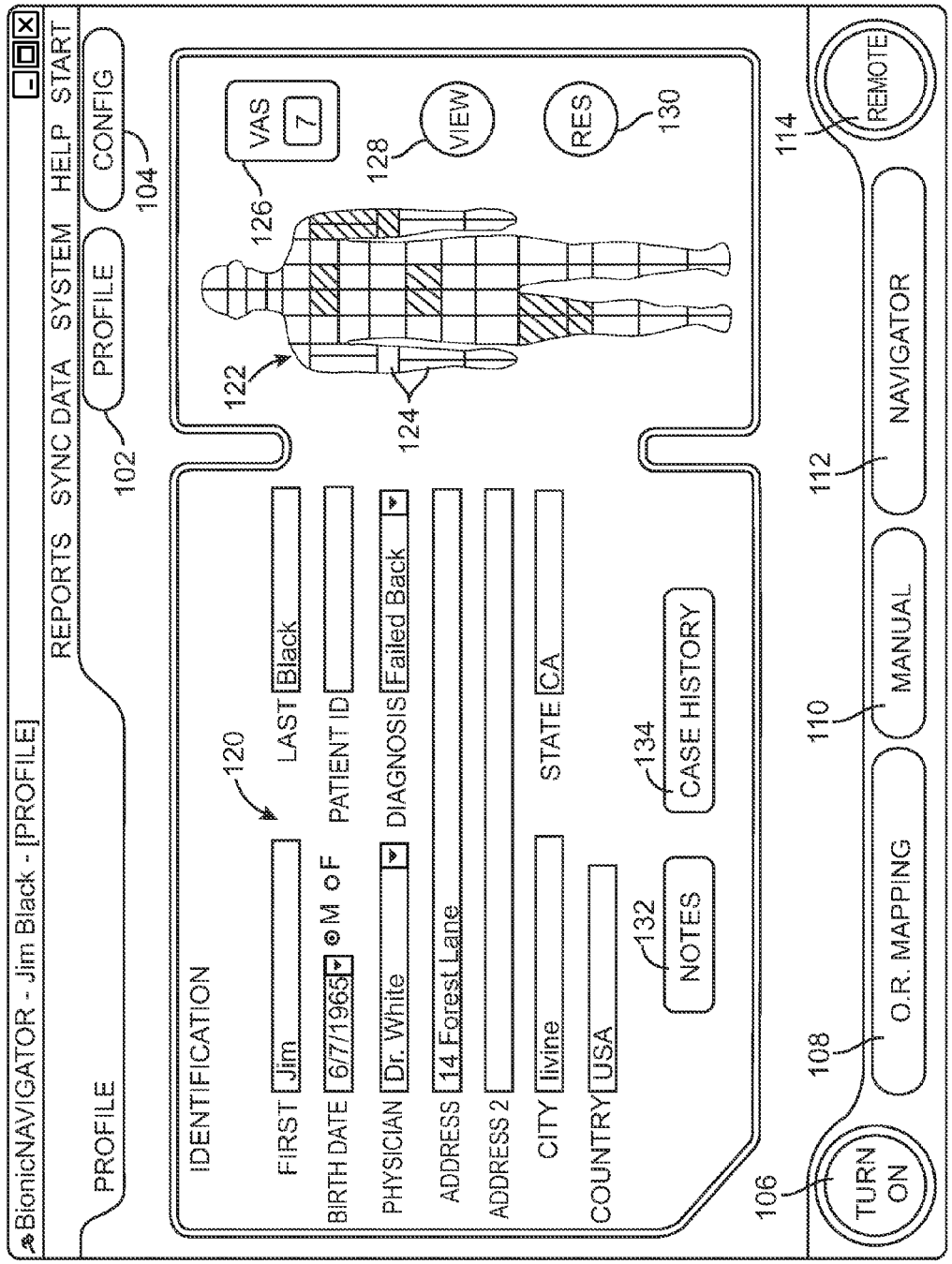
FIG. 8 is a patient profiles screen that can be displayed by the computerized programming system of FIG. 6.
Figure 9:
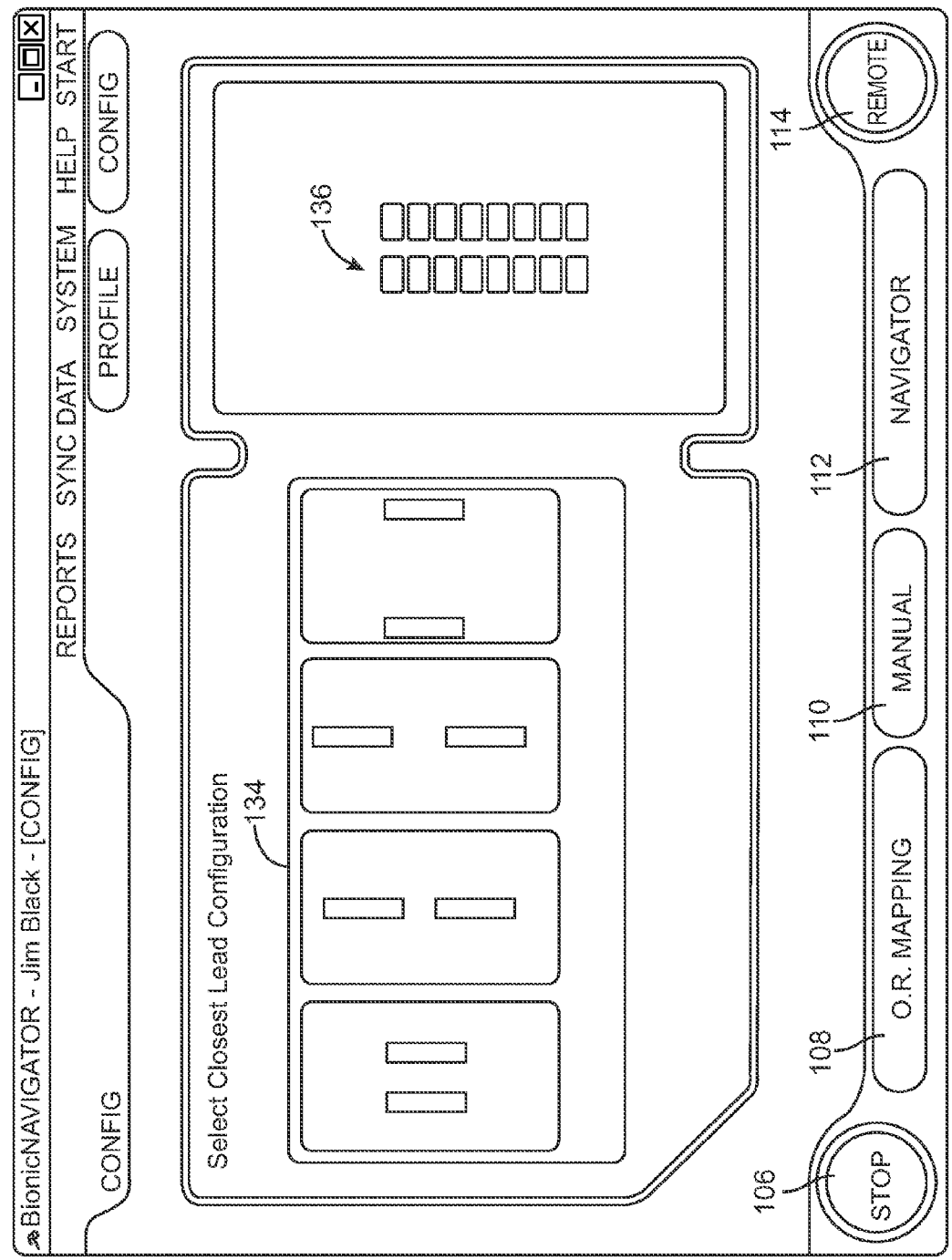
FIG. 9 is a lead configuration screen that can be displayed by the computerized programming system of FIG. 6.

As shown in FIG. 8, actuation of the profile button 102 opens a patient profile screen 100(2) that includes a multitude of identification boxes 120 that allows the clinician to create, edit information required to generate or update a patient record, such as, e.g., name, birth date, patient identification, physician, diagnosis, and address. The patient profile screen 100(2) also provides a pain map of the human body 122 divided into several regions 124. Clicking on one or more of these regions 124 allows the clinician to record the regions of pain experienced by the patient. In the illustrated embodiment, the upper back, lower back, right arm, and left thigh of the patient are highlighted, indicating that these are the regions of pain experienced by the patient. The patient profile screen 100(2) also has a visual analog scale (VAS) 126 that can be clicked to allow the clinician to manually record the amount of pain experienced by the patient from a scale of 0 (no pain) to 10 (worst imaginable pain), both without therapy and during therapy. The patient profile screen 100(2) also has a view button 128 that can be clicked to toggle the pain map 122 between a front view and a rear view, and a resolution button 128 that can be clicked to toggle the resolution of the regions 124 in the pain map 122 between low and high. The patient profile screen 100(2) also has a case history button 130 that can be clicked to allow the clinician to review the date and time of each procedure performed on the patient, and a notes button 132 that can be clicked to allow the clinician to enter notes in a free-form manner that can be subsequently reviewed in the case history.

Figure 10:
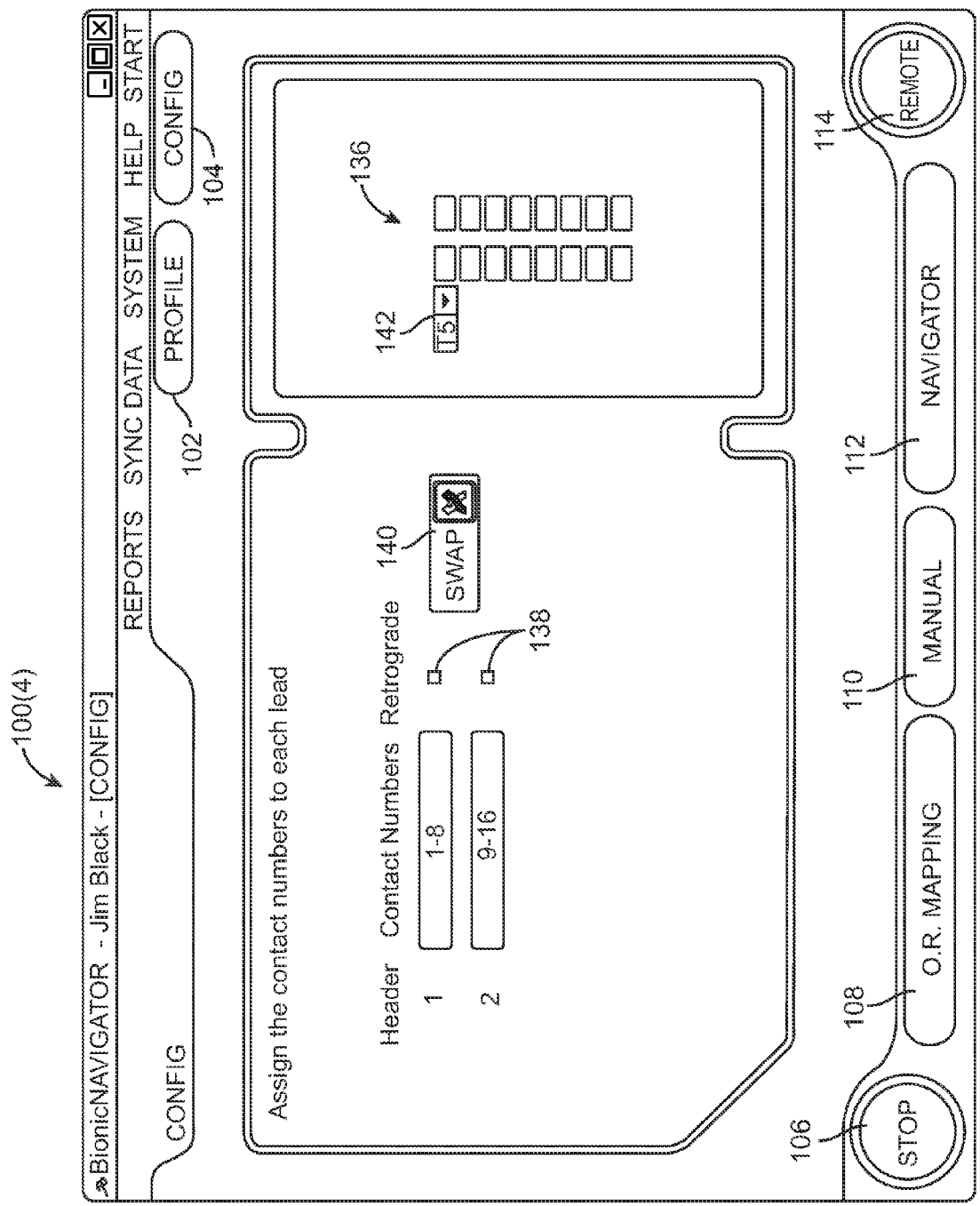
FIG. 10 is a lead orientation screen that can be displayed by the computerized programming system of FIG. 6.

Actuation of the configuration button 104 allows a clinician to access a lead configuration screen 100(3) (shown in FIG. 9) and a lead orientation screen 100(4) (shown in FIG. 10).

The lead configuration screen 100(3) has four different graphical configurations 134 that can be clicked on to select a specific lead configuration (e.g., a closely spaced side-by-side configuration, a closely spaced top-bottom configuration, a widely spaced top-bottom configuration, or a widely spaced side-by-side configuration) that matches the actual configuration of the implanted leads 12. In this case, the closely spaced side-by-side configuration is shown selected, which is shown in a graphical representation of two electrode octets 136.

The lead orientation screen 100(4) allows the clinician to select the lead direction, assign the electrode numbers to each lead, and the vertebral position of the leads. In particular, the lead orientation screen 100(4) has a retrograde box 138 that can be clicked to indicate how the lead is vertically oriented. In this case, neither of the retrograde boxes 138 has been checked, so that first octet of electrodes will be numbered from 1 to 8 starting from the top of the first lead, and the second octet of electrodes will be numbered from 9 to 16 starting from the top of the second lead. However, in the case where the first retrograde box 138 is checked, the first octet of electrodes will be numbered from 8 to 1 starting from the top of the first lead, and the second octet of electrode will be numbered from 16 to 9 starting from the top of the second lead. The lead orientation screen 100(4) also has a swap button 140 that can be clicked to associate the electrode octets (1-8 and 9-16) to the first and second leads, with the nominal designation being electrodes 1-8 on the first lead and electrodes 9-16 on the second lead. The lead orientation screen 100(4) has a vertebral location pull down menu 142 next to the graphical electrode representation 136 that a clinician can use to indicate the vertebral position of the leads (e.g., C1-C7.5, T1-T12.5, L1-L5.5, S1-S5). In the example, the T5 vertebral position has been selected.

Figure 11:
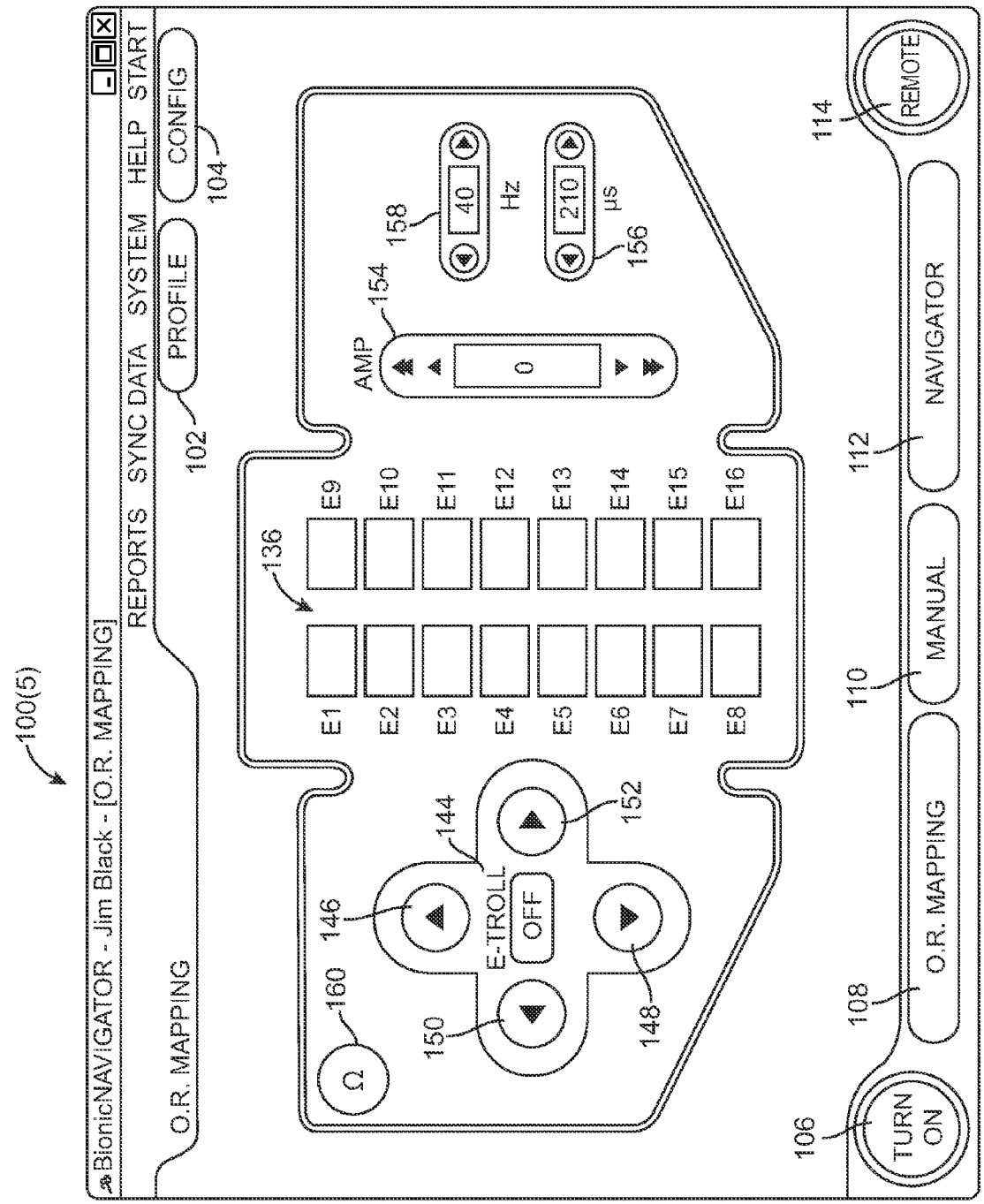
FIG. 11 is a first operating room mapping screen that can be displayed by the computerized programming system of FIG. 6.

As shown in FIG. 11, actuation of the OR mapping button 108 opens an OR mapping screen 100(5) that allows a clinician to assess lead position and evaluate paresthesia coverage during surgery. In particular, the OR mapping screen 100(5) allows both Electronic Trolling (E-Troll) and manual electrode selection. Actuation of the power-on button 106 in the OR mapping screen 100(5) directs the IPG 14 to alternatively deliver or cease delivering stimulation energy to the electrode array 26 in accordance with the stimulation parameters generated during the E-troll and manual electrode selection functions.

E-Troll is a quick way to sweep the electrode array by gradually moving a cathode in bipolar stimulation. To this end, the OR mapping screen 100(5) includes an E-Troll button 144 that can be clicked to enable the E-trolling function, and up, down, left, and right arrows 146-152 to respectively move the cathode up, down, left and right in the electrode array, thereby steering the electrical current, and thus, the resulting stimulation region, up, down, left, and right in the electrode array.

Figure 12:
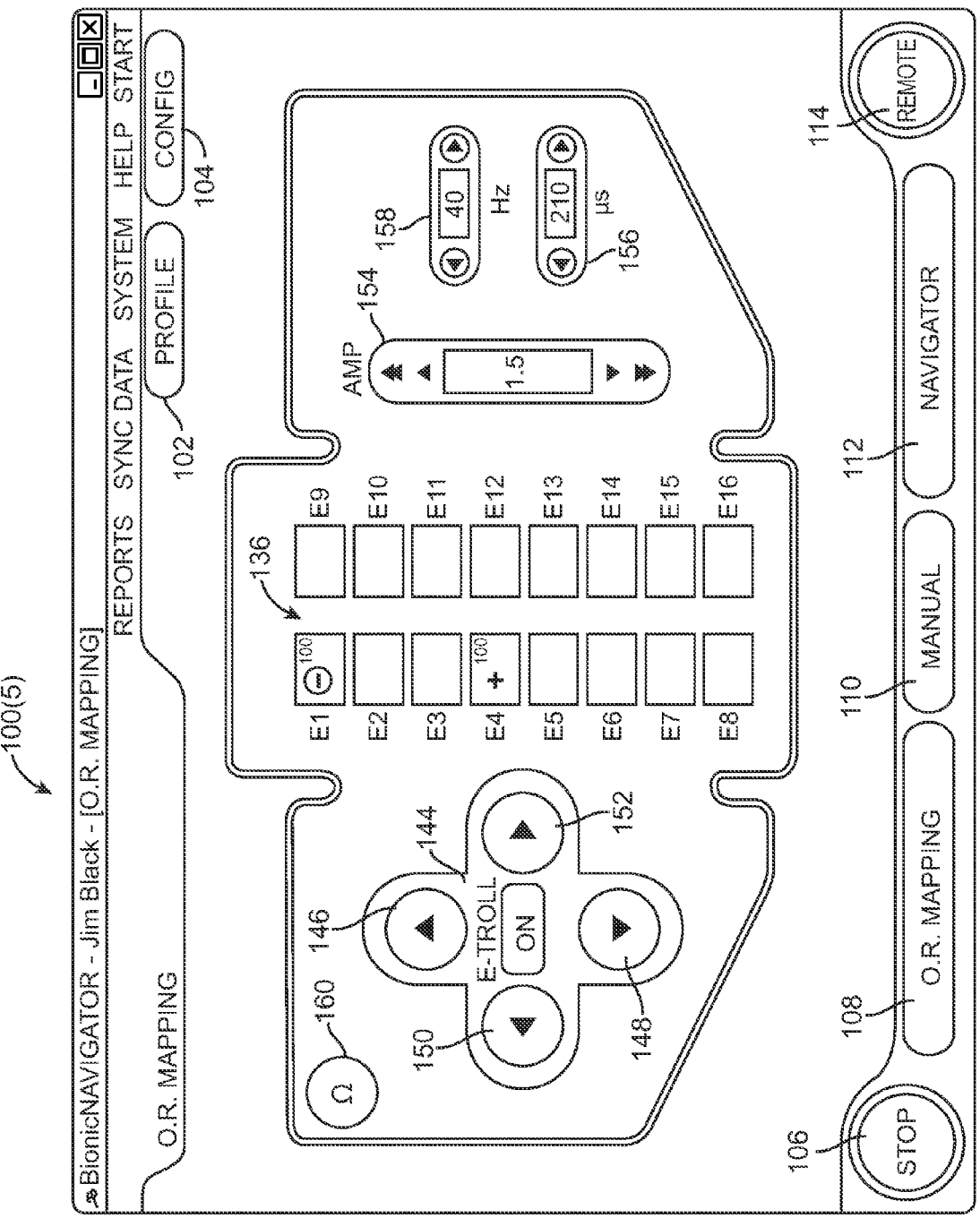
FIG. 12 is a second operating room mapping screen that can be displayed by the computerized programming system of FIG. 6, particularly showing a first fractionalized electrode configuration in the E-Troll mode.
Figure 13:
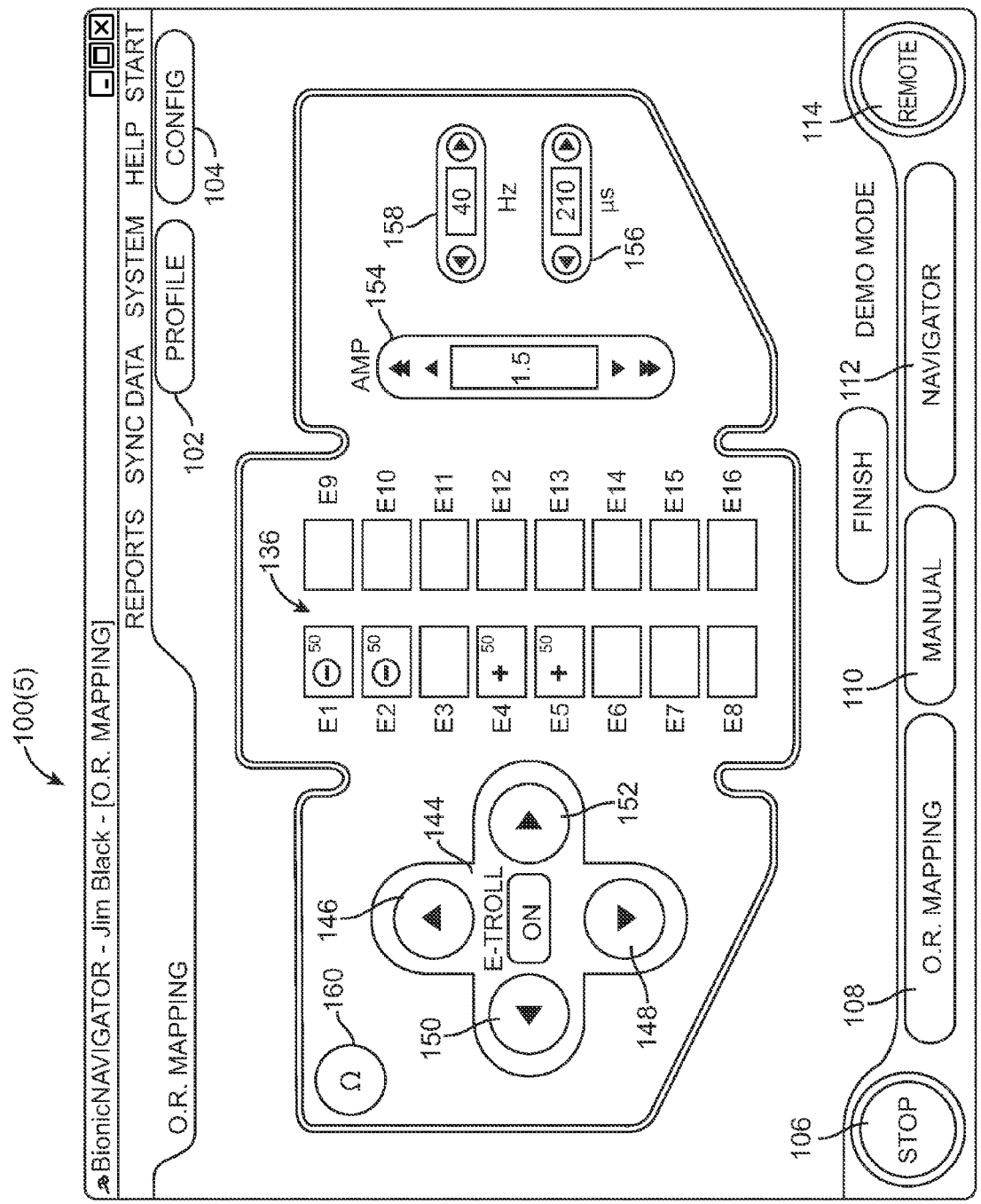
FIG. 13 is a third operating room mapping screen that can be displayed by the computerized programming system of FIG. 6, particularly showing a second fractionalized electrode configuration in the E-troll mode.
Figure 14:
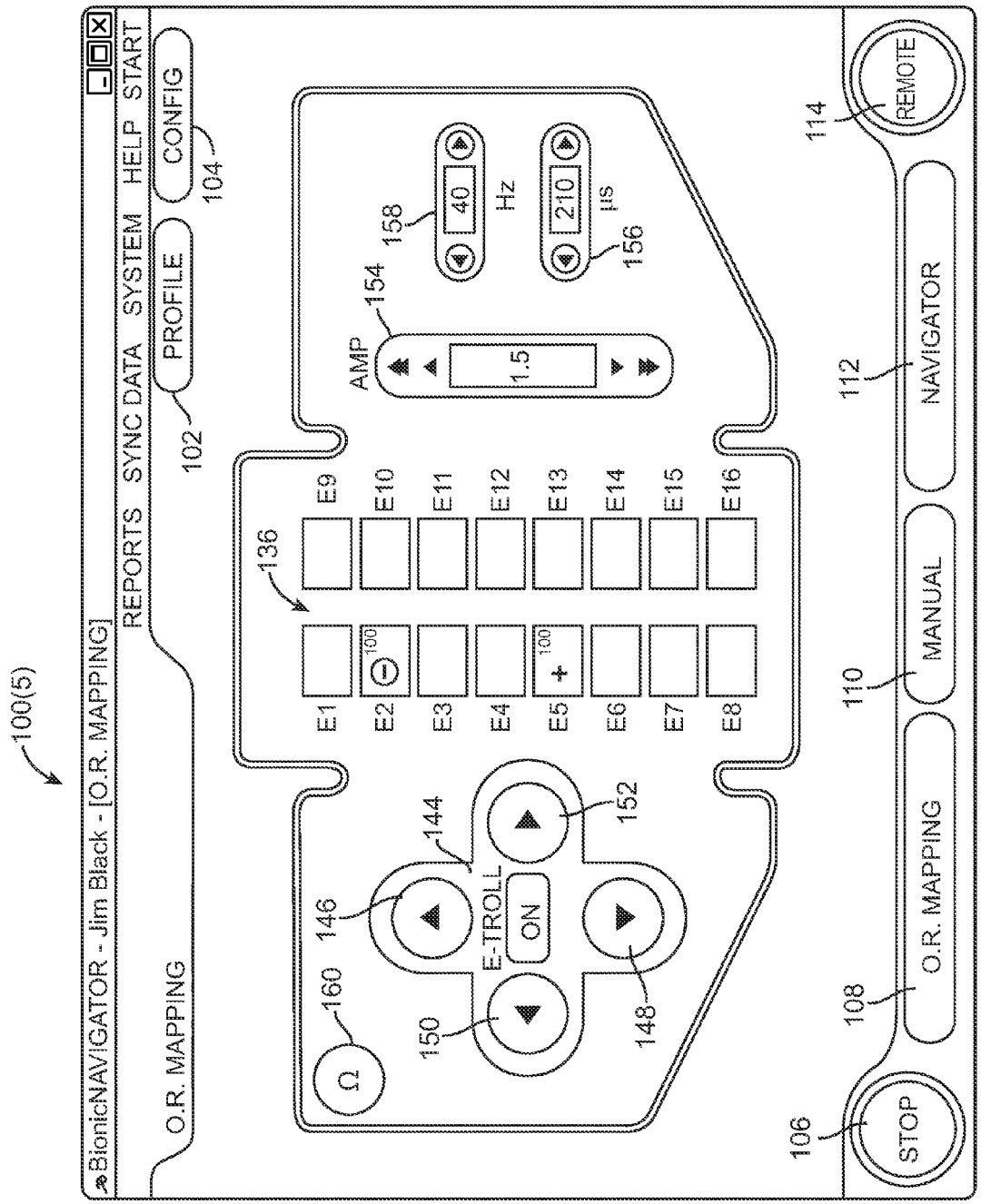
FIG. 14 is a fourth operating room mapping screen that can be displayed by the computerized programming system of FIG. 6, particularly showing a third fractionalized electrode configuration in the E-troll mode.

For example, as shown in FIG. 12, the E-Troll process may begin by designating electrode E1 as the sole cathode and electrode 4 as the sole anode. As there shown, electrode E1 has a fractionalized cathodic current value of 100%, and electrode 4 has a fractionalized anodic current value of 100%. If the down button 148 is clicked, the cathodic current is gradually shifted from electrode E1 to electrode E2, and the anodic current is gradually shifted from electrode E4 to electrode E5, which gradually shifting occurs in 10% increments. For example, as shown in FIG. 13, the electrical current is shifted, such that electrode E1 has a fractionalized cathodic current value of 50%, electrode E2 has a fractionalized cathodic current value of 50%, electrode E4 has a fractionalized anodic current value of 50%, electrode E5 has a fractionalized anodic current value of 50%. As shown in FIG. 14, the electrical current is further shifted, such that electrode E2 has a fractionalized cathodic current value of 100%, and electrode E5 has a fractionalized anodic current value of 100%. Further clicking of the down button 148 shifts the cathodic current and anodic current further down the electrode array in a similar manner. Likewise, clicking the up button 146, left button 150, or right button 152 causes the cathodic currents and anodic currents to respectively shift up, left, and right within the electrode array in a similar manner.

In the illustrated embodiment, a navigation table, such as the one shown in Appendix A, is used to generate fractionalized electrode configurations for each lead 12. Because the navigation table only contains fractionalized electrode configurations for a single lead (i.e., 8 electrodes), two identical navigation tables will be used to independently generate fractionalized electrode configurations for each lead 12 (one for electrodes E1-E8 and one for electrodes E9-E16), which for purposes of displaying to the clinician in OR mapping screen 100(5), can then be combined into a single fractionalized electrode configuration and normalized, such that the fractionalized cathodic current for both leads 12 (i.e., the entire electrode array 26) totals 100% and the fractionalized anodic current for both leads 12 (i.e., the entire electrode array 26) totals 100%.

The cathodic and anodic currents can be shifted up and down along each lead 12 by stepping up and down through the fractionalized electrode configurations within the navigation table. The cathodic and anodic currents can be shifted left and right by scaling the currents on the first and second leads relative to each other. That is, to steer current from the second lead to the first lead, the fractionalized electrode configuration for the second lead is scaled down, and the fractionalized electrode configuration for the first lead is scaled up, and to steer current from the first lead to the second lead, the fractionalized electrode configuration for the first lead is scaled down, and the fractionalized electrode configuration for the second lead is scaled up.

Figure 15:
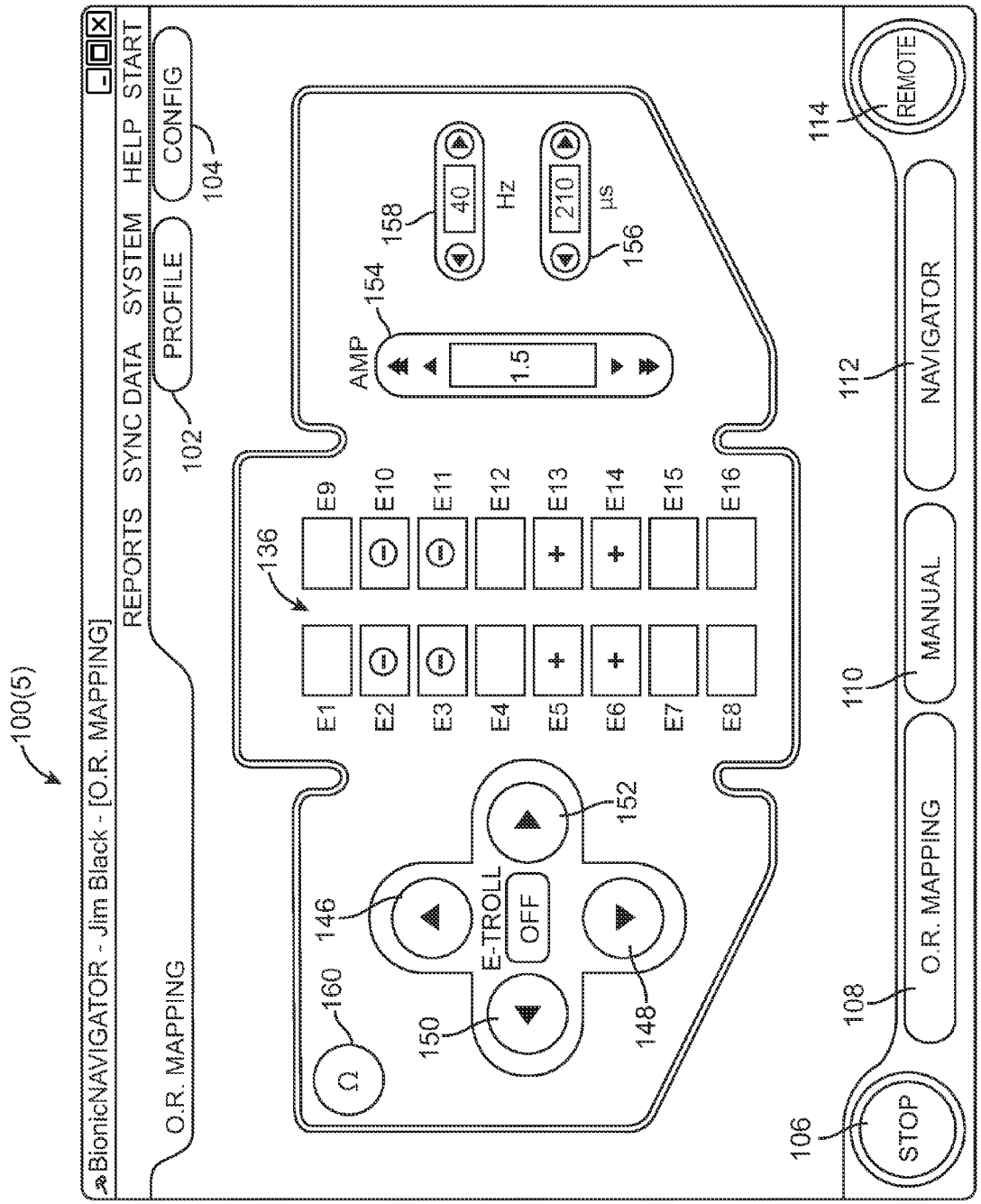
FIG. 15 is a fifth operating room mapping screen that can be displayed by the computerized programming system of FIG. 6, particularly showing an electrode combination in a manual mode.

The E-Troll button 144 can be clicked again to allow the clinician to manually select the electrodes. In particular, any of the electrodes E1-E16 can be clicked to select the electrode as being either an anode (+), cathode (−), or off (0). In the illustrated embodiment, such selection can be accomplished simply by clicking on the respective electrode multiple times to designate the electrode as an anode (−), then a cathode (+), and then off (0). If a multipolar electrode arrangement is desired, at least one of the electrodes E1-E16 will be selected as an anode (+) and at least one other of the electrodes E1-E16 will be selected as a cathode (−). As shown in FIG. 15, electrodes E2, E3, E10, and E11 are designated as cathodes, and electrodes E5, E6, E13, and E14 are designated as anodes. If a monopolar electrode arrangement is desired, none of the electrodes E1-E16 will be selected as an anode (+).

The OR mapping screen 100(5) also allows the clinician to modify the stimulation energy (i.e., the electrical pulse parameters) output by the IPG 14 to the electrodes during either of the E-troll or manual electrode selection functions by adjusting each of a pulse amplitude, pulse width, or pulse rate. To this end, OR mapping screen 100(5) includes a pulse amplitude adjustment control 154, the top arrow of which can be clicked to incrementally increase the pulse amplitude of the stimulation energy, and the bottom arrow of which can be clicked to incrementally decrease the pulse amplitude of the stimulation energy. The OR mapping screen 100(5) further includes a pulse width adjustment control 156, the right arrow of which can be clicked to incrementally increase the pulse width of the stimulation energy, and the left arrow of which can be clicked to incrementally decrease the pulse width of the stimulation energy. The OR mapping screen 100(5) further includes a pulse rate adjustment control 158, the right arrow of which can be clicked to incrementally increase the pulse rate of the stimulation energy, and the left arrow of which can be clicked to incrementally decrease the pulse rate of the stimulation energy. Notably, the adjustment of the pulse amplitude, pulse width, and pulse rate will be performed globally for all of the electrodes activated as either an anode (+) or a cathode (−). The OR mapping screen also includes an impedance button 160 that can be clicked to allow the clinician to verify electrical impedance. In particular, the lead impedance can be measured and displayed on an impedance map (not shown) for each of the electrodes E1-E16.

Figure 16:
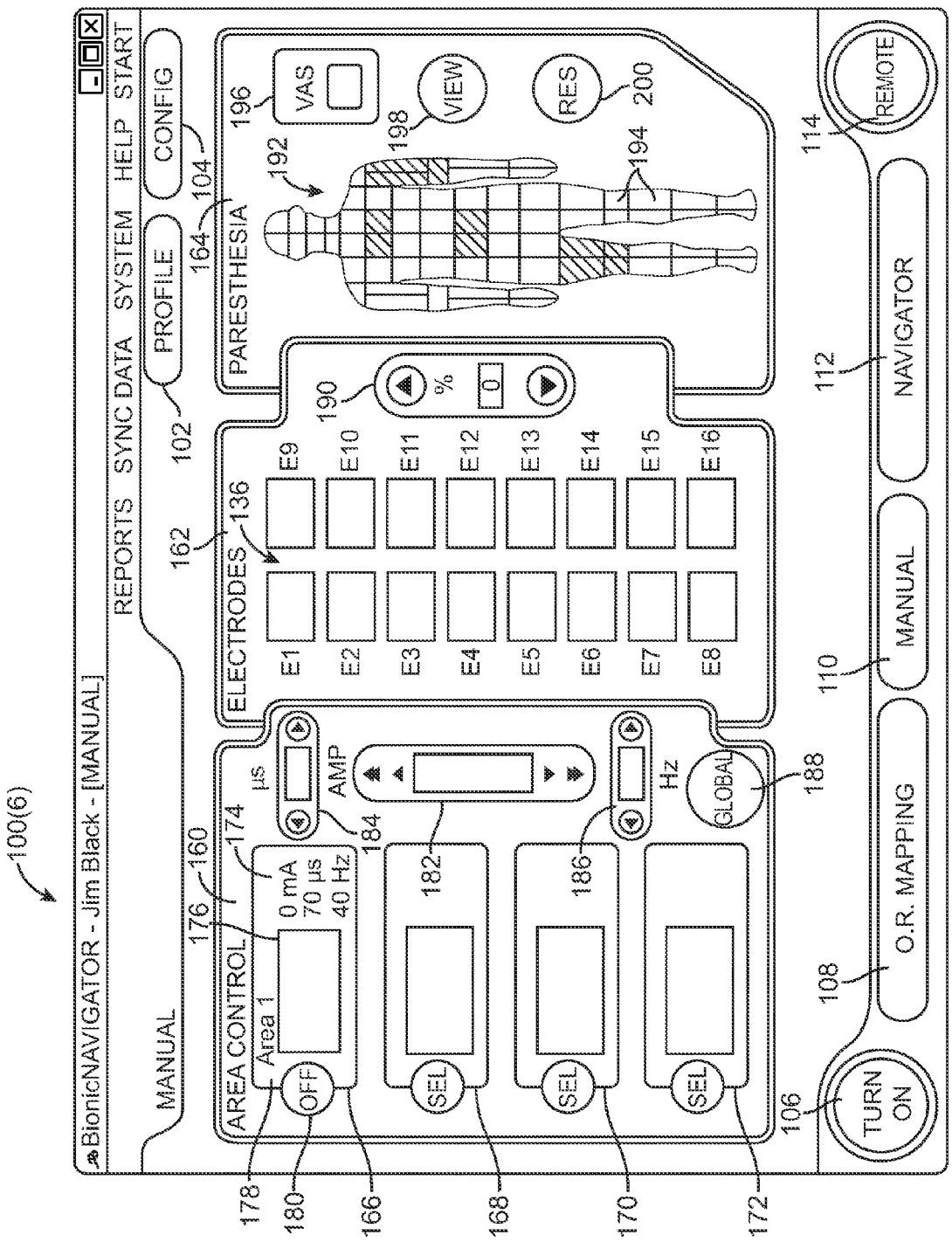
FIG. 16 is a first manual programming screen that can be displayed by the computerized programming system of FIG. 6.

As shown in FIG. 16, actuation of the manual button 110 opens a manual programming screen 100(6) that allows a clinician to manually select stimulation parameter sets, including the fractionalized electrode configurations. To this end, the manual programming screen 100(6) includes an area control panel 160, an electrodes panel 162, and a paresthesia panel 164.

Figure 17:
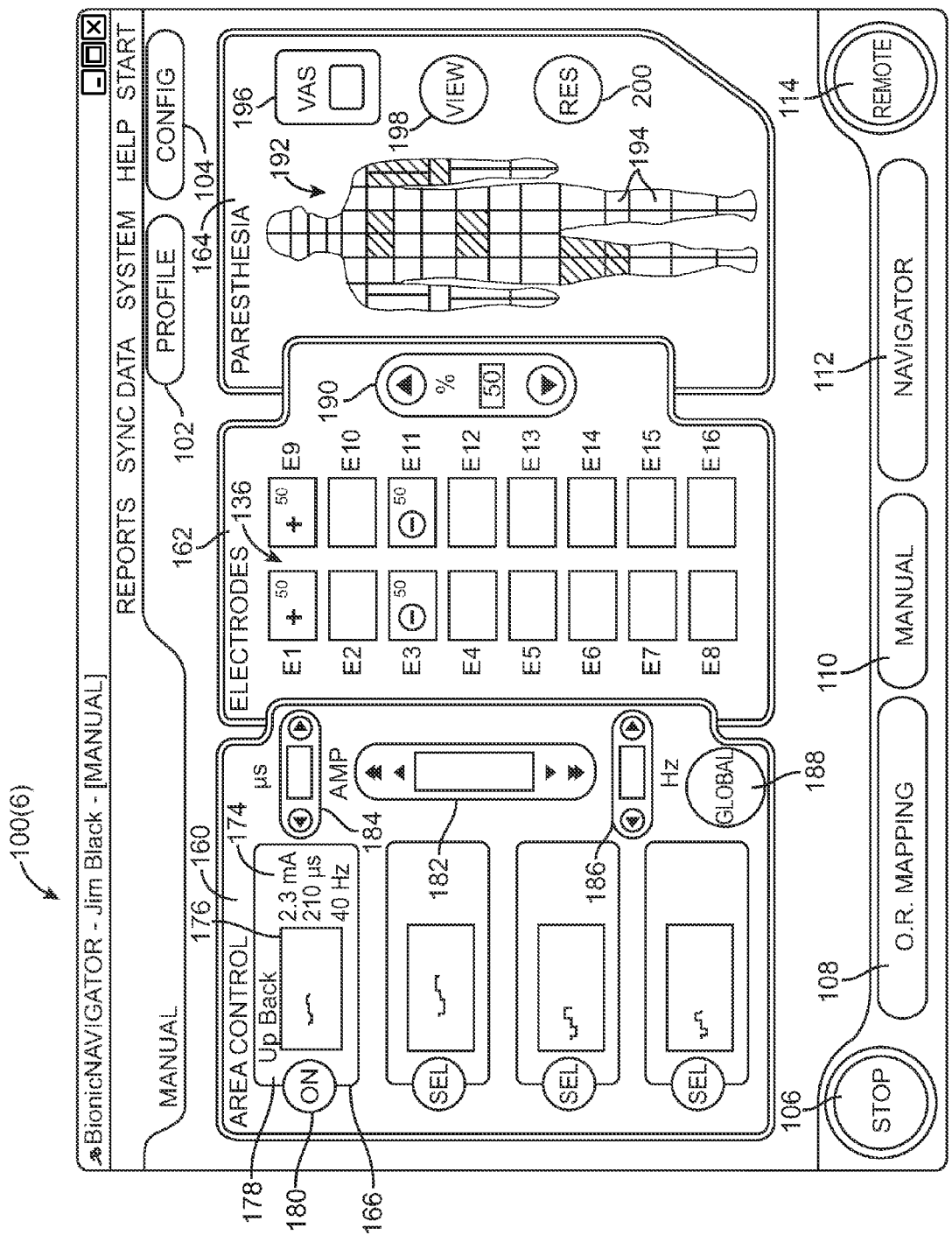
FIG. 17 is a second manual programming screen that can be displayed by the computerized programming system of FIG. 6, particularly showing a first fractionalized electrode configuration.
Figure 18:
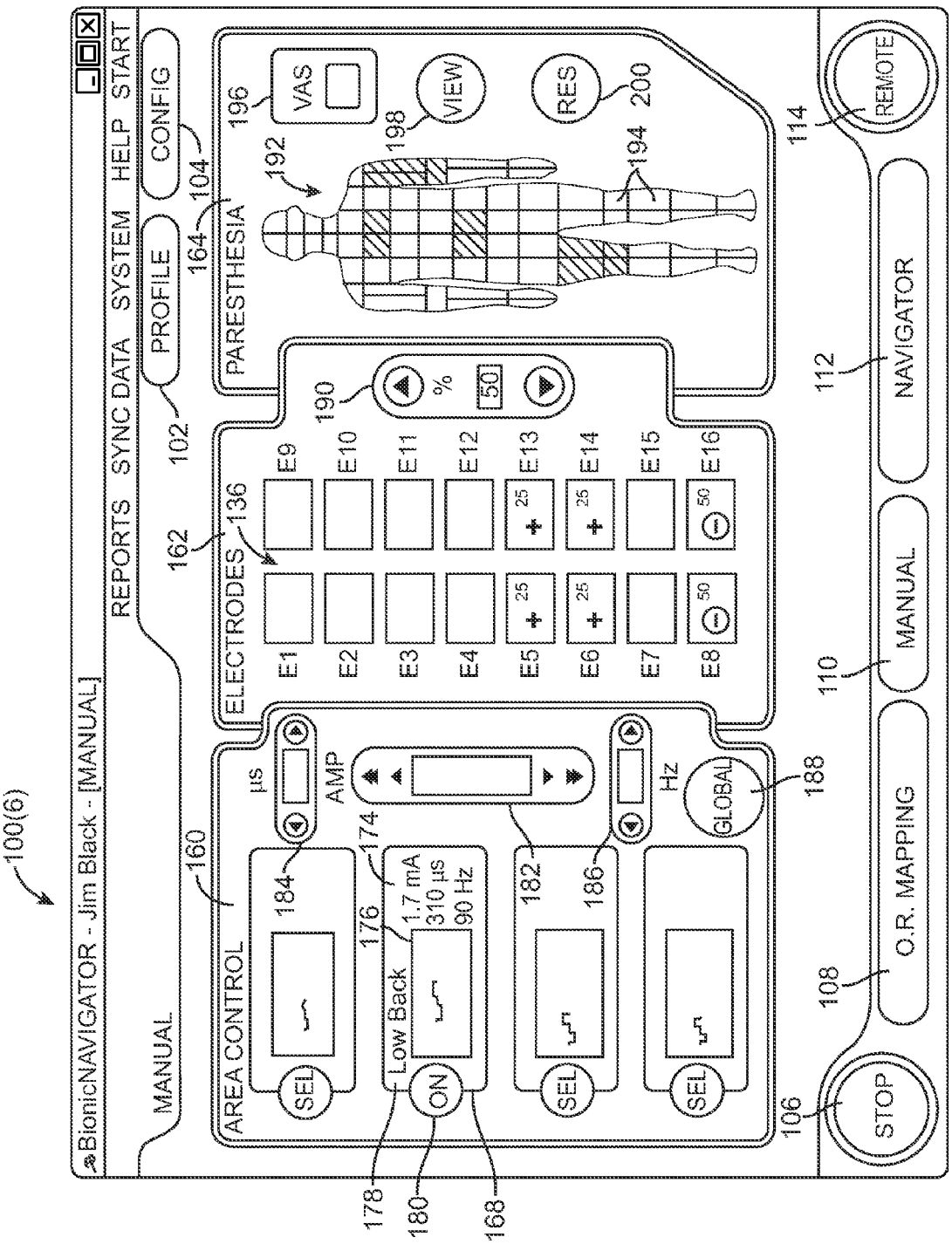
FIG. 18 is a third manual programming screen that can be displayed by the computerized programming system of FIG. 6, particularly showing a second fractionalized electrode configuration.
Figure 19:
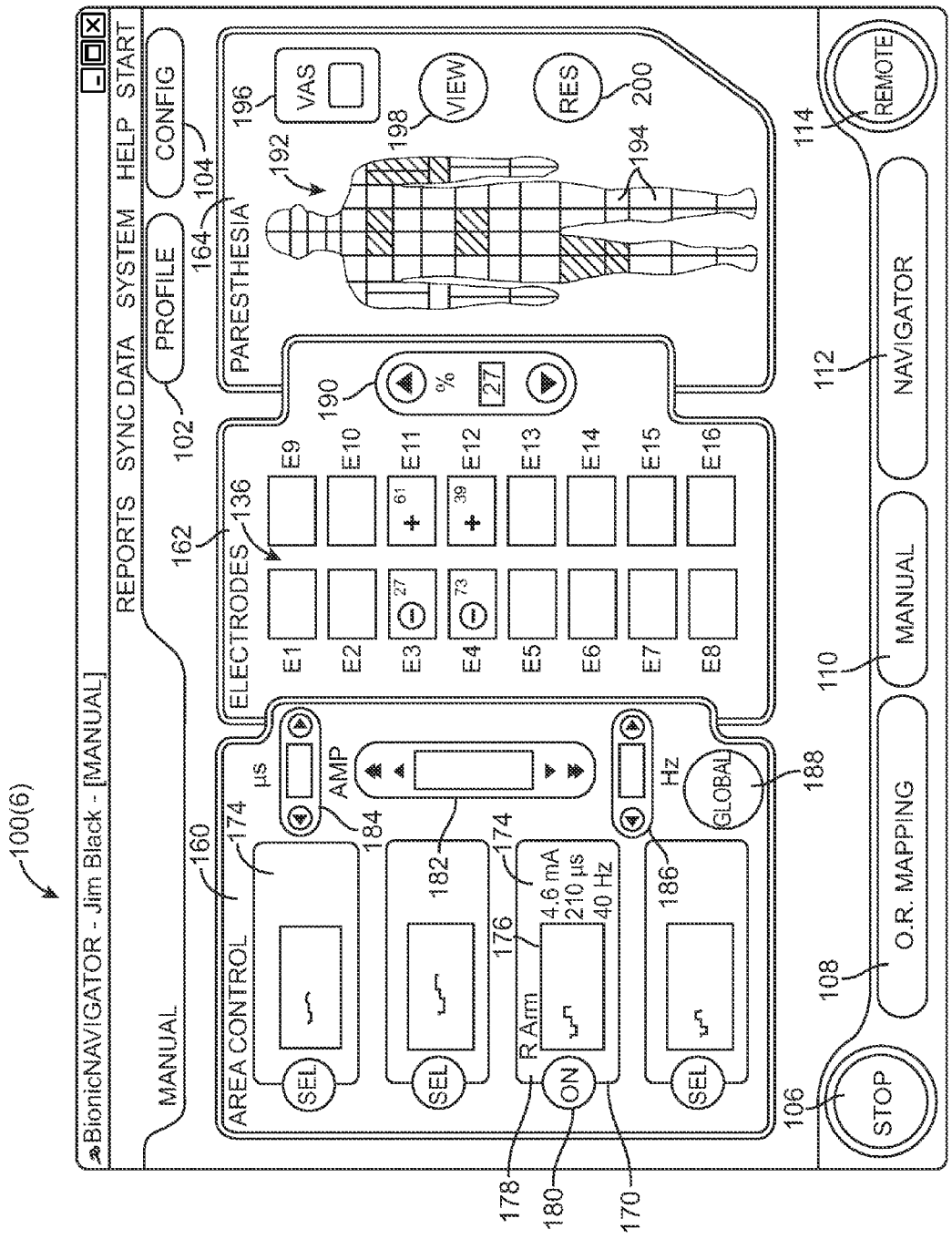
FIG. 19 is a fourth manual programming screen that can be displayed by the computerized programming system of FIG. 6, particularly showing a third fractionalized electrode configuration.
Figure 20:
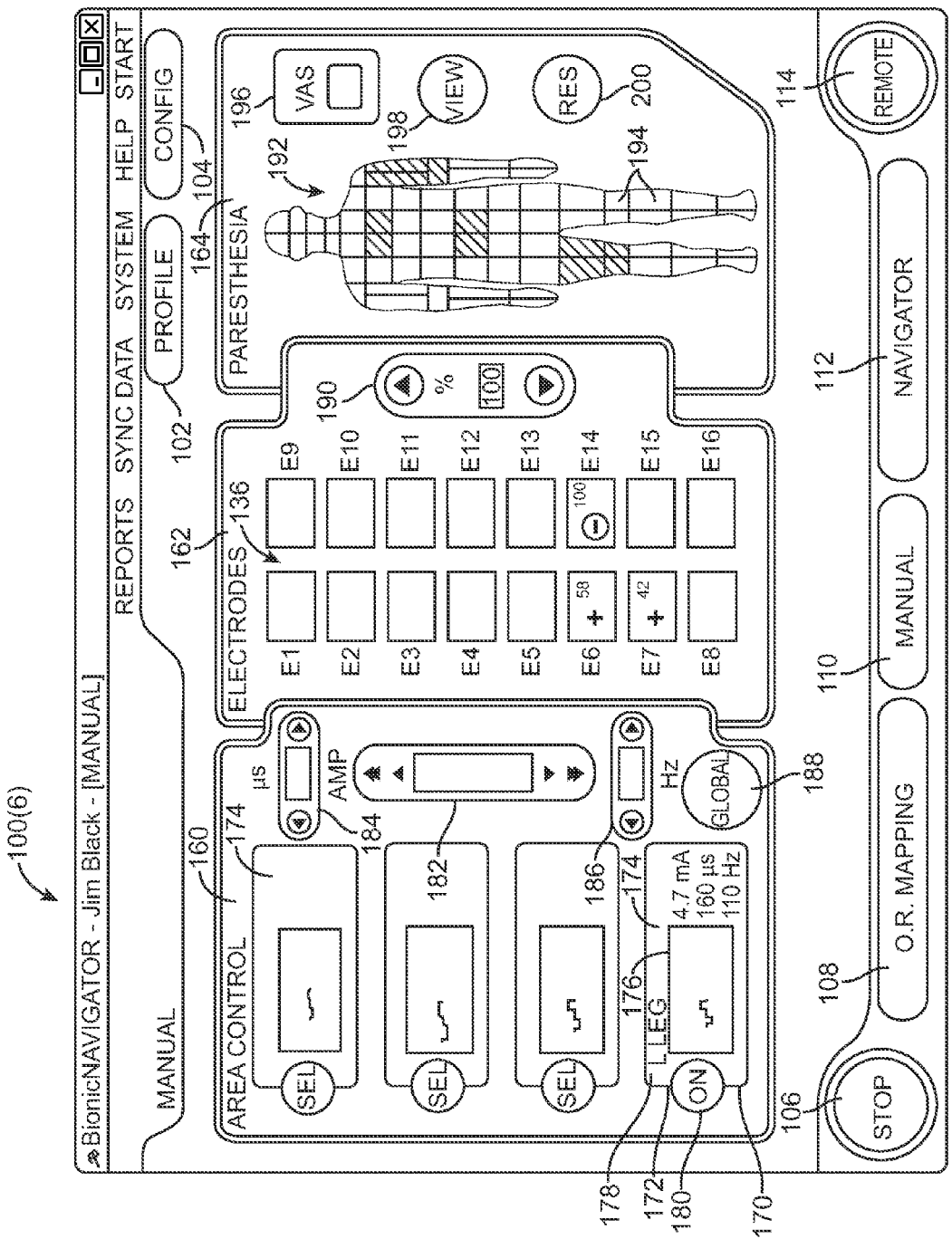
FIG. 20 is a fifth manual programming screen that can be displayed by the computerized programming system of FIG. 6, particularly showing a fourth fractionalized electrode configuration.

The area control panel 160 includes four coverage areas 166-172 with which up to four stimulation parameter sets can respectively be associated to create a stimulation program. Each of the coverage areas 166-172 displays the electrical pulse parameters 174, and specifically, the pulse amplitude, pulse width, and pulse rate, of the stimulation parameter set associated with the coverage area, a graphical display 176 of the pulse waveform characterized by the electrical pulse parameters, and a coverage area designator 178. In this example, the first coverage area 166, which is designated as the upper back, has a pulse amplitude of 2.3 mA, a pulse width of 210 µs, and a pulse rate of 40 Hz, as illustrated in FIG. 17; the second coverage area 168, which is designated as the lower back, has a pulse amplitude of 3.7 mA, a pulse width of 310 µs, and a pulse rate of 90 Hz, as illustrated in FIG. 18; the third simulation region 170, which is designated as the right arm, has a pulse amplitude of 4.6 mA, a pulse width of 210 µs, and a pulse rate of 40 Hz, as illustrated in FIG. 19; and the fourth coverage area 172, which is designated as the left leg, has a pulse amplitude of 4.7 mA, a pulse width of 160 µs, and a pulse rate of 110 Hz, as illustrated in FIG. 20.

Each of the coverage areas 166-172 also has a selection button 180 that can be clicked to activate or deactivate the coverage area. When a coverage area is activated by clicking the power-on button 106, stimulation energy is delivered from the IPG 14 to the electrode array 26 in accordance with the stimulation parameter set associated with coverage area. The graphical display 176 shows the pulse waveform as moving to indicate that the coverage area has been activated. As shown in FIGS. 17-20, four coverage areas with different electrical pulse parameters can be activated. Notably, multiple ones of the coverage areas 166-172 can be simultaneously activated by clicking selection buttons 180 for the respective coverage areas.

The area control panel 160 allows the clinician to modify the stimulation energy (i.e., the electrical pulse parameters) output by the IPG 14 to the electrode array 26 for the respective one of the coverage areas 166-172 that is selected by adjusting each of a pulse amplitude, pulse width, or pulse rate. To this end, the area control panel 160 includes a pulse amplitude adjustment control 182, the top arrow of which can be clicked to incrementally increase the pulse amplitude of the stimulation energy, and the bottom arrow of which can be clicked to incrementally decrease the pulse amplitude of the stimulation energy. The area control panel 160 further includes a pulse width adjustment control 184, the right arrow of which can be clicked to incrementally increase the pulse width of the stimulation energy, and the left arrow of which can be clicked to incrementally decrease the pulse width of the stimulation energy. The area control panel 160 further includes a pulse rate adjustment control 186, the right arrow of which can be clicked to incrementally increase the pulse rate of the stimulation energy, and the left arrow of which can be clicked to incrementally decrease the pulse rate of the stimulation energy. The area control panel 160 further includes a global button 188 that can be clicked to allow the clinician to globally modify the pulse amplitude of selected ones of the coverage areas 166-172.

The electrode panel 162 includes the graphical electrode representation 136, which can be clicked by the clinician to select each electrode as being either an anode (+), cathode (−), or off (0) to form fractionalized electrode configurations for each of the coverage areas. In the illustrated embodiment, such selection can be accomplished simply by clicking on the respective electrode multiple times to designate the electrode as an anode (−), then a cathode (+), and then off (0). If a multipolar electrode arrangement is desired, at least one of the electrodes E1-E16 will be selected as an anode (+) and at least one other of the electrodes E1-E16 will be selected as a cathode (−). If a monopolar electrode arrangement is desired, none of the electrodes E1-E16 will be selected as an anode (+). The electrode panel 162 also includes an up-down current adjustment control 190 that can be manipulated to assign a fractionalized current for each of the active electrodes E1-E16. In particular, for each electrode selected to be activated as either a cathode or anode, the clinician can click on the upper arrow of the control 190 to incrementally increase the absolute value of the fractionalized current of the selected electrode, and the clinician can click on the lower arrow of the control 190 to incrementally decrease the absolute value of the fractionalized current. Notably, the total fractionalized current value for any group of anodes will equal 100% and the total fractionalized current value for any group of cathodes will equal 100%.

For the first coverage area 166, electrodes E1 and E9 each has a fractionalized anodic current value of 50%, and electrodes E3 and E11 each has a fractionalized cathodic current value of 50%, as shown in FIG. 17. For the second coverage area 168, electrodes E5, E6, E13, and E14 each has a fractionalized anodic current value of 25%, and electrodes E8 and E16 each has a fractionalized cathodic current value of 50%, as shown in FIG. 18. For the third coverage area 170, electrodes E11 and E12 respectively have fractionalized anodic current values of 61% and 39%, and electrodes E3 and E4 respectively have fractionalized cathodic current values of 27% and 73%, as shown in FIG. 19. For the fourth coverage area 172, electrodes E6 and E7 respectively have fractionalized anodic current values of 58% and 42%, and electrode E14 has a fractionalized cathodic current value of 100%, as shown in FIG. 20. Each of the fractionalized electrode configurations are combined with the electrical pulse parameters of the corresponding coverage area to form a set of stimulation parameters.

The paresthesia panel 164 includes a paresthesia map of the human body 192 divided into several regions 194. Clicking on one or more of these regions 194 allows the clinician to record the regions of paresthesia experienced by the patient for the currently selected coverage area. The paresthesia map 192 also includes the regions 194 previously highlighted as indicating pain in the patient profiles screen 100(2). Thus, the upper back, lower back, right arm, and left thigh of the patient are highlighted, indicating that these are the regions of pain experienced by the patient. Clicking on any of the regions 194 in the paresthesia map 192 further highlights the regions (shown with hatched lines) experienced by the patient has having paresthesia. Any region of paresthesia that corresponds to the same region previously indicated as having pain will be highlighted with a different color.

As shown in FIG. 17, the upper back of the patient is highlighted to indicate the region where the patient is experiencing paresthesia when the first coverage area 166 is turned on. As shown in FIG. 18, the lower back of the patient is highlighted to indicate the region where the patient is experiencing paresthesia when the second coverage area 168 is turned on. As shown in FIG. 19, the right arm of the patient is highlighted to indicate the region where the patient is experiencing paresthesia when the third coverage area 170 is turned on. As shown in FIG. 20, the left leg of the patient is highlighted to indicate the region where the patient is experiencing paresthesia when the fourth coverage area 172 is turned on. The paresthesia panel 164 also has a visual analog scale (VAS) 196 that can be clicked to allow the clinician to manually record the amount of pain experienced by the patient from a scale of 0 (no pain) to 10 (worst imaginable pain) when the respective coverage area or areas are turned on. The paresthesia panel 164 also has a view button 198 that can be clicked to toggle the paresthesia map 192 between a front view and a rear view, and a resolution button 200 that can be clicked to toggle the resolution of the regions 194 in the paresthesia map 192 between low and high.

Figure 21:
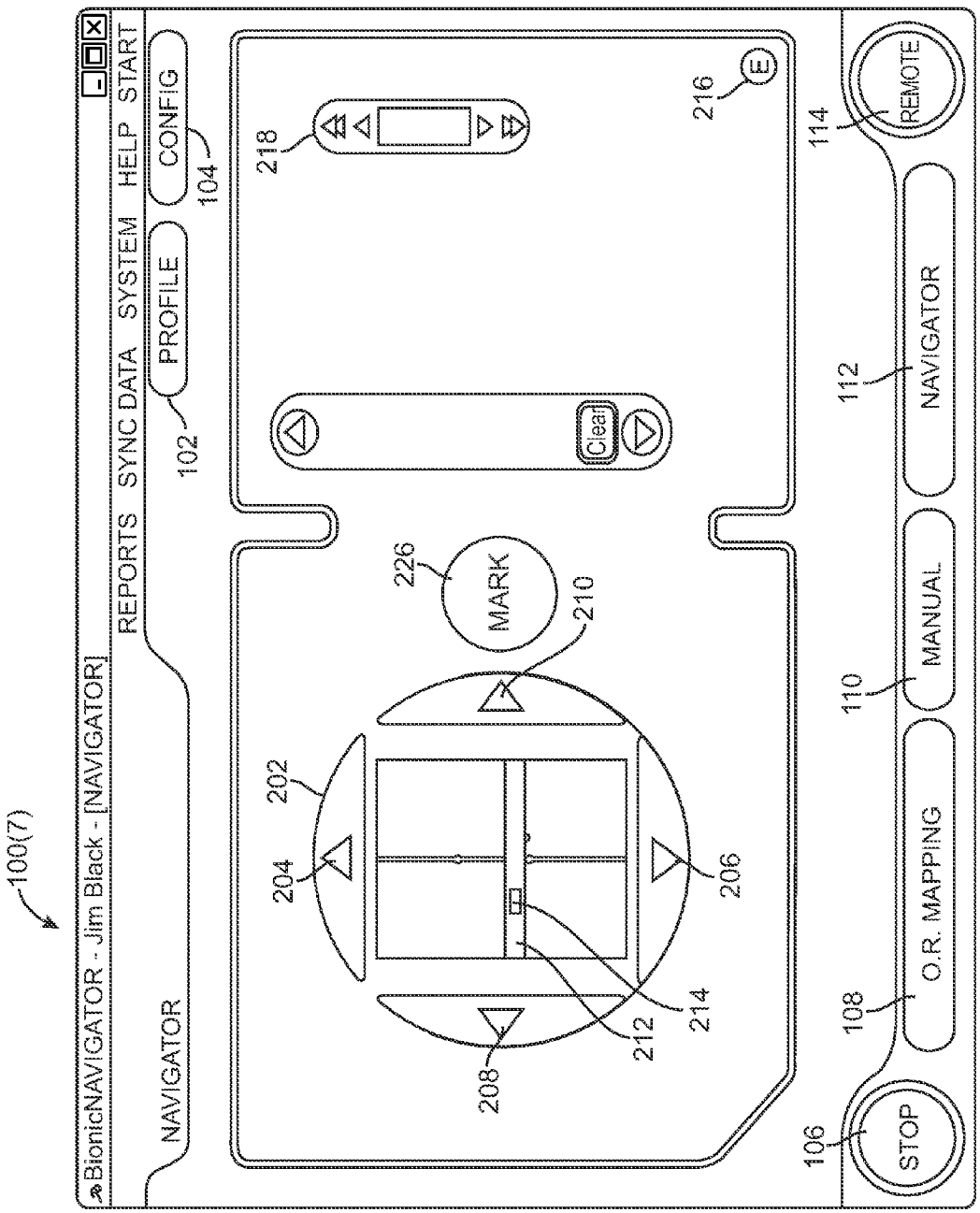
FIG. 21 is a first navigator programming screen that can be displayed by the computerized programming system of FIG. 6.

As shown in FIG. 21, actuation of the navigator button 112 opens a navigator screen 100(7) that allows a clinician to shift current between multiple electrode combinations to fine tune and optimize stimulation coverage for patient comfort. To this end, the navigator screen 100(7) includes a navigator scope 202 that represents the stimulation region along the spinal cord relative to the electrode array that can be targeted using directional controls 204-210 (up, down, left, and right arrows). The navigator scope 202 has a horizontal bar 212 with a location designator (represented by a rectangular opening) 214 that indicates the current location of the stimulation region relative to the electrode array. Clicking on the up and down control arrows 204, 206 displaces the horizontal bar 212, and thus the location designator 214, up and down within the navigator scope 202, and clicking on the left and right control arrows 208, 210 displaces the location designator 214 left and right along the horizontal bar 212. Thus, the stimulation region can be displaced upward by clicking on the up control arrow 204, displaced downward by clicking on the down control arrow 206, displaced to the left by clicking on the left control arrow 208, and displaced to the right by clicking on the right control arrow 210.

Significantly, the navigator scope 202 displaces the stimulation region by steering the electrical current (i.e., shifting electrical current between the electrodes E1-E16) in a manner similar to that used by the E-Troll function described above to shift current between the electrodes E1-E16. Thus, clicking the up control arrow 204 displaces the cathode upward in the electrode array, thereby displacing the stimulation region upward relative the spinal cord; clicking the down control arrow 206 displaces the cathode downward in the electrode array, thereby displacing the stimulation region downward relative to the spinal cord; clicking the left control arrow 208 displaces the cathode to the left in the electrode array, thereby displacing the stimulation region to the left relative to the spinal cord; and clicking the right control arrow 210 displaces the cathode to the right in the electrode array, thereby displacing the stimulation region to the left relative to the spinal cord.

Notably, a steering table, such as the one shown in Appendix A, is used to shift the cathodic and anodic currents up and down along each lead 12 by stepping through the fractionalized electrode configurations within the navigation table for each lead 12. The cathodic and anodic currents can be shifted left and right by scaling the currents on the first and second leads 12 relative to each other. In the same manner as the E-troll function described above, for purposes of displaying to the clinician in navigator screen 100(7) (described further below), can then be combined into a single fractionalized electrode configuration and normalized, such that the fractionalized cathodic current for both leads 12 (i.e., the entire electrode array 26) totals 100% and the fractionalized anodic current for both leads 12 (i.e., the entire electrode array 26) totals 100%.

It should be appreciated that, in the illustrated embodiment, the steering table shown in Appendix A is used shift the cathodic and anodic currents up and down along each lead 12 using simultaneously delivered pulses (and in this case, by using fractionalized current values in each row of the steering table to generate stimulation in only one timing channel). For example, to gradually shift from a fractionalized current value configuration of 100% cathodic current on electrode E1 and 100% anodic current on electrode E3 to 100% cathodic current on electrode E1 and 100% anodic current on electrode E4, the fractionalized electrode configurations between rows 21 and 41 will be stepped through.

However, this is not the only way of gradually shifting cathodic and anodic current up and down along each lead 12. For example, the cathodic and anodic currents can be gradually shifted up and down along each lead 12 using time-interleaved pulses, with the first interleaved pulse having a first set of fractionalized current values and the second interleaved pulse having a second set of fractionalized current values, and then gradually decreasing the total current for the first set of fractionalized current values, while gradually increasing the total current for the second set of fractionalized current values. For example, to gradually shift from a fractionalized current value configuration of 100% cathodic current on electrode E1 and 100% anodic current on electrode E3 to 100% cathodic current on electrode E1 and 100% anodic current on electrode E4, the two fractionalized electrode configurations will be respectively used to generate stimulation pulses that are interleaved between two timing channels. For each iteration, however, the total current of the first fractionalized configuration will be incrementally reduced, while the total current of the second fractionalized electrode configuration will be incrementally increased until the total current for the first fractionalized configuration is reduced to zero.

If the electrical current values are viewed in an absolute sense, the first technique gradually shifts a first set of absolute electrical current values to a second set of absolute electrical current values by generating a series of simultaneously delivered pulses of equal total current during a single timing channel, while gradually changing fractionalized electrode configurations. In contrast, the second technique gradually shifts the first set of absolute electrical current values to the second set of absolute electrical current values by generating a series of time-interleaved pulses from two fractionalized electrode configurations, while gradually shifting the total current of the first fractionalized electrode configuration in the first timing channel to the second fractionalized electrode configuration in the second timing channel.

Figure 22:
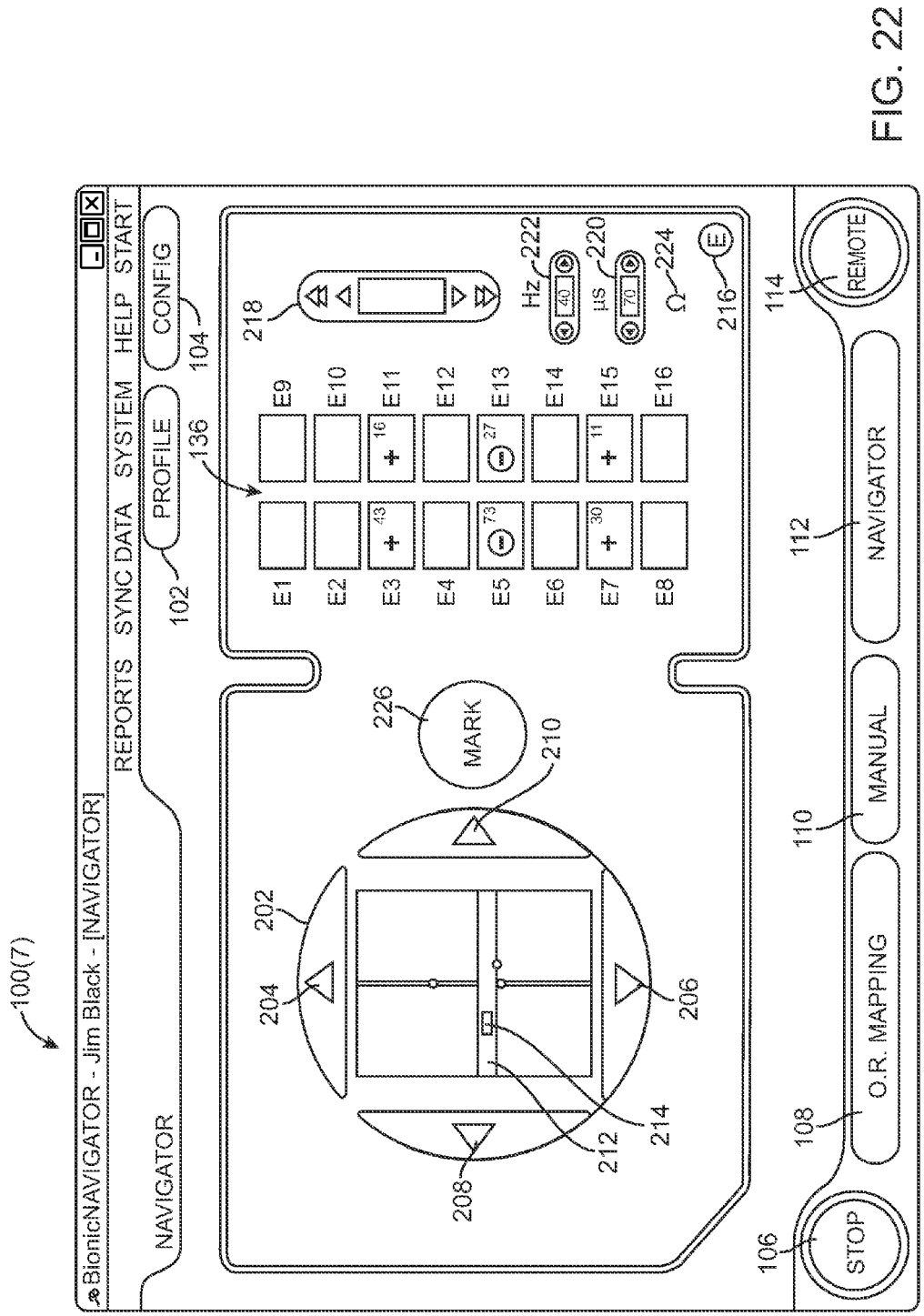
FIG. 22 is a second navigator programming screen that can be displayed by the computerized programming system of FIG. 6, particularly showing a fractionalized electrode configuration.

The navigator screen 100(7) also includes an electrode combination button 216 that can be clicked to allow clinician to view the fractionalized electrode configuration that corresponds to the stimulation region identified by the location designator 214, as shown in FIG. 22. As there shown, electrodes E2, E6, E10, and E14 respectively have fractionalized cathodic current values of 36%, 36%, 14%, and 14%, and electrodes E4 and E12 respectively have anodic current values of 71% and 29% to locate the stimulation region at the location currently pointed to by the location designator 214. The navigator screen 100(7) also allows the clinician to modify the stimulation energy (i.e., the electrical pulse parameters) output by the IPG 14 by adjusting each of a pulse amplitude or a pulse rate.

To this end, the navigator screen 100(7) includes a pulse amplitude adjustment control 218, the top arrow of which can be clicked to incrementally increase the pulse amplitude of the stimulation energy, and the bottom arrow of which can be clicked to incrementally decrease the pulse amplitude of the stimulation energy. The navigator screen 100(7) further includes a pulse width adjustment control 220 (provided only in the navigator screen 100(7) illustrated in FIG. 22), the right arrow of which can be clicked to incrementally increase the pulse width of the stimulation energy, and the left arrow of which can be clicked to incrementally decrease the pulse width of the stimulation energy. Notably, the adjustment of the pulse amplitude, pulse width, and pulse rate will be performed globally for all of the electrodes activated as either an anode (+) or a cathode (−). While the navigator screen 100(7) does not include a pulse rate adjustment control, it does include a pulse rate display 222 (provided only in the navigator screen 100(7) illustrated in FIG. 22) that provides the default pulse rate for the system to the clinician. The navigator screen 100(7) also includes an impedance button 224 (provided only in the navigator screen 100(7) illustrated in FIG. 22) that can be clicked to allow the clinician to verify electrical impedance by displaying an impedance map (not shown).

Figure 23:
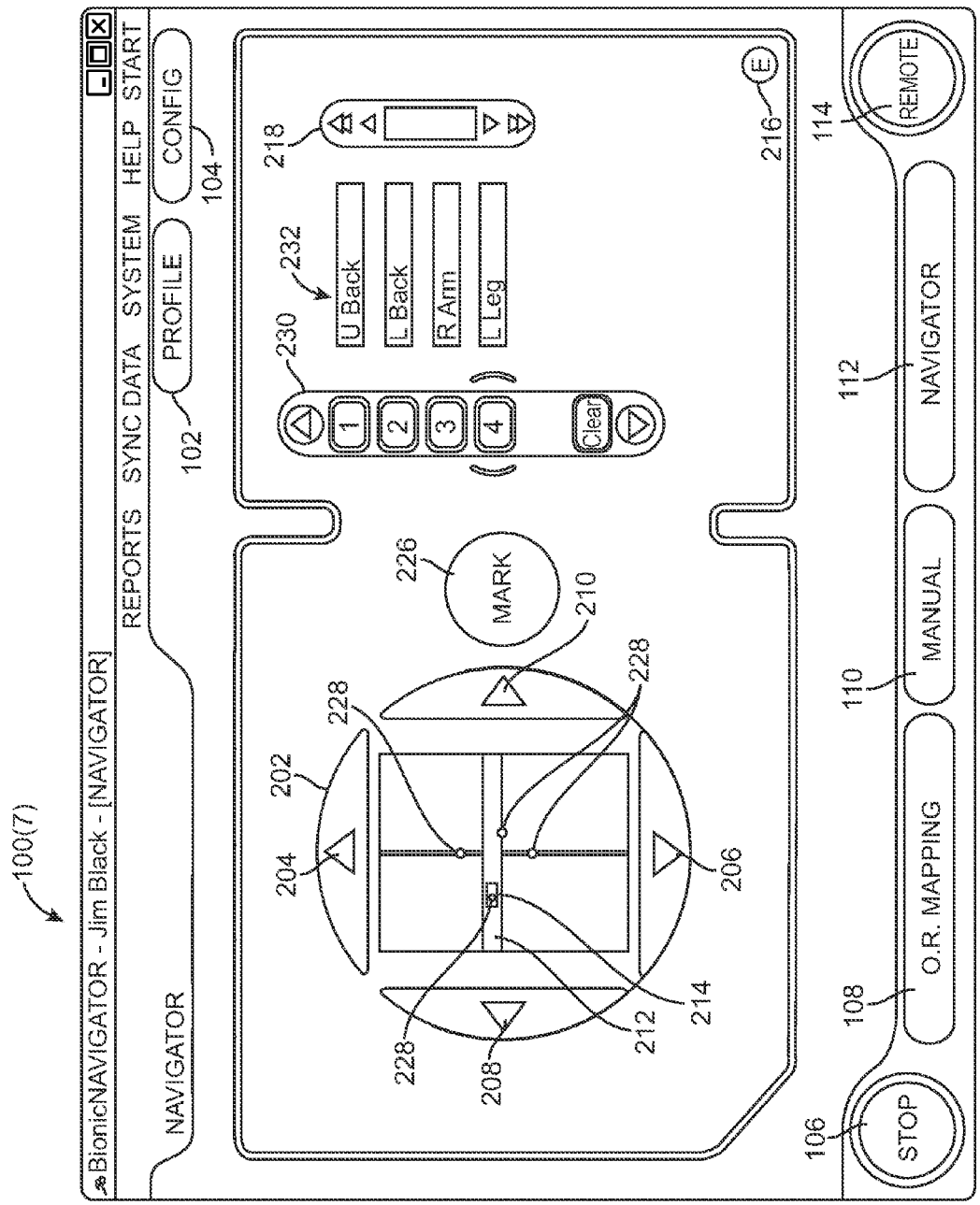
FIG. 23 is a third navigator programming screen that can be displayed by the computerized programming system of FIG. 6, particularly showing the creation of four marks and corresponding stimulation regions.

As shown in FIG. 23, the navigator screen 100(7) has a mark button 226 that can be clicked to mark points 228 where coverage is preferred for the target area; that is, the area that the location designator 214 currently points to when the mark button 226 is clicked will be marked. Each mark 228 is a set of stimulation parameters (including fractionalized electrode configuration, pulse amplitude, pulse width, and pulse rate) that corresponds to the location or area of the stimulation region. The navigator screen 100(7) includes a mark list 230 that includes numbered designators corresponding to all of the marks 228 generated by the navigator scope 202 and an area designator 232 that can be filled in by the clinician to associate an area of paresthesia for each mark 228. As shown in FIG. 23, four marks 228 have been generated, with the first mark being identified as causing paresthesia in the upper back of the patient, the second mark being identified as causing paresthesia in the lower back of the patient, the third mark being identified as causing paresthesia in the right arm of the patient, and the fourth mark being identified as causing paresthesia in the left leg of the patient. Notably, any one of the numbered designated within the mark list 230 can be clicked to center the area designator 232 on the corresponding mark 228 in the navigation scope 202.

Figure 24:
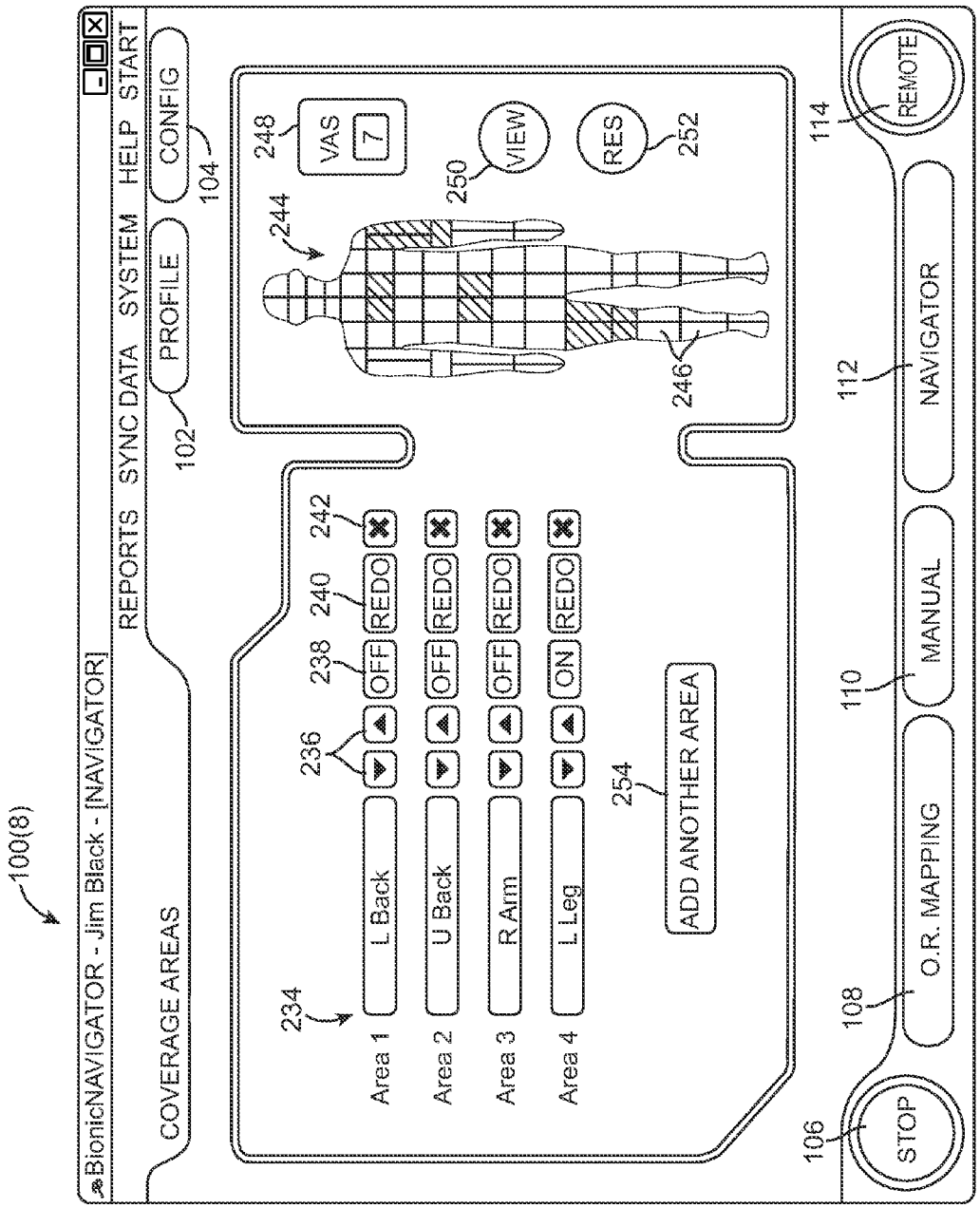
FIG. 24 is a coverage areas screen that can be displayed by the computerized programming system of FIG. 6.

After the marks 228 are generated, a coverage areas screen 100(8) that allows the clinician to generate a stimulation program from the marks 228 is provided, as shown in FIG. 24. The coverage areas screen 100(8) includes a list of the coverage areas 234 with corresponding control buttons. In particular, each coverage area 234 has associated with it amplitude up/down arrows 236 that can be clicked to modify the mark corresponding to that coverage area 234 by increasing or decreasing the amplitude of the stimulation energy conveyed by the electrode array 26. Each coverage area 234 also includes an on/off button 238 that can be clicked to alternately provide or cease the delivery of the stimulation energy from the IPG 14 to the electrode array 26. Any combination of the coverage areas 234 can be turned on, so that multiple coverage areas of the patient can be simultaneously stimulated. Each coverage area 234 also includes a redo button 240 that regenerates and stores the mark 228 with any new amplitude values that are adjusted by manipulation of the amplitude up/down arrows 236, and a deletion button 242 that deletes the mark 228 and associated area designation from the coverage areas screen 100(8).

The coverage areas screen 100(8) further includes a paresthesia map of the human body 244 divided into several regions 246. Clicking on one or more of these regions 246 allows the clinician to record the regions of paresthesia experienced by the patient for the areas that have been turned on. The paresthesia map 244 also includes the regions 246 previously highlighted as indicating pain in the patient profiles screen 100(2). Thus, the upper back, lower back, right arm, and left thigh of the patient are highlighted, indicating that these are the regions of pain experienced by the patient. Clicking on any of the regions 246 in the paresthesia map 244 further highlights the regions experienced by the patient has having paresthesia. Any region of paresthesia that corresponds to the same region previously indicated as having pain will be highlighted with a different color (shown hatched). As shown in FIG. 24, the left leg of the patient is highlighted to indicate the region where the patient is experiencing paresthesia when the fourth coverage area 234 is turned on. The coverage areas screen 100(8) includes a VAS button 248, view button 250, and resolution button 252 that can be clicked or manipulate the paresthesia map 244 in the same manner described above with respect to the paresthesia map 192 in the manual programming screen 100(6).

The coverage areas screen 100(8) further includes an add another area button 254 that can be clicked to allow the clinician to add additional marks 228, and thus, coverage areas 234 in the navigator screen 100(7) illustrated in FIG. 23. As will described in further detail below, the groups of stimulation parameter sets can be combined into a single stimulation program that can then be stored in the RC 16 and IPG 14.

Figure 25:
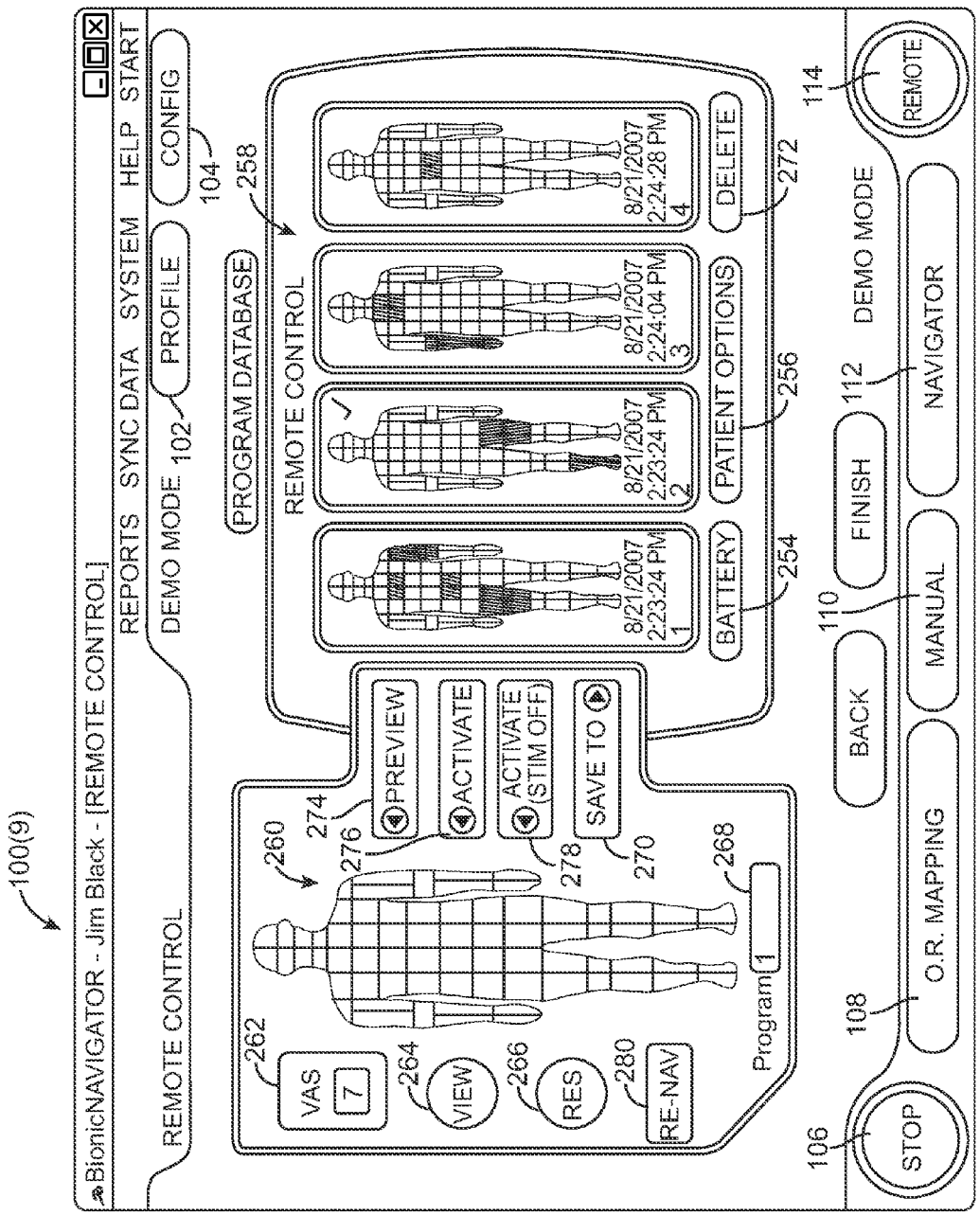
FIG. 25 is a remote control screen that can be displayed by the computerized programming system of FIG. 6.

As shown in FIG. 25, actuation of the remote button 114 opens a remote screen 100(9) that allows the clinician to check battery status and modify patient options for the RC 16, activate stimulation programs previously stored in the RC 16 and IPG 14, and store the stimulation parameter sets created during the navigation or manual programming sessions in the RC 16 and IPG 14 as a new stimulation program.

To this end, the remote screen 100(9) has a battery status button 254 that can be clicked to provide a battery status screen (not shown) that displays the battery status of the IPG 14. The remote screen 100(9) further has a patient options button 256 that can be clicked to provide a patient options screen (not shown) that allows the clinician to view and edit additional program settings for a patient, such as stimulation cycling, ramp up time, and maximum amplitude, and to provide lockout options that prevent the patient from modifying stimulation parameters, such as pulse width and pulse width. The remote screen 100(9) further includes a program database 258 that has four slots for storing up to four stimulation programs. As there shown, four different stimulation programs, which are represented by corresponding paresthesia maps, are stored in the program database 258, along with the date/time that the stimulation programs were stored in the program database 258 and the program identification. Any of the stimulation programs stored in the program database 258 can be selected for activation by clicking on the corresponding slot containing the stimulation program. A check mark is placed next to the paresthesia map corresponding to the last activated or last saved stimulation program.

The remote screen 100(9) includes a paresthesia map 260 corresponding to the currently activated stimulation program, and a VAS button 262, view button 264, and resolution button 266 that can be clicked or manipulate the paresthesia map 260 in the same manner described above with respect to the paresthesia map 192 in the manual programming screen 100(6). Notably, when the remote screen 100(9) is entered from the navigator screen 100(7) or the manual programming screen 100(6), the currently activated stimulation program will be the new stimulation program generated in these screens. The remote screen 100(9) also includes a program entry box 268 that identifies the currently activated stimulation program using a designator that can be manipulated by the clinician. The remote screen 100(9) further includes a save to button 270 that can be clicked to save the currently activated stimulation program into a selected slot of the program data base 258. If the selected slot already contains a previously stored stimulation program, this program will be overwritten by the currently activated stimulation program. The remote screen 100(9) also includes a delete button 272 that can be clicked to delete the stimulation program currently selected in the program database 258.

The remote screen 100(9) further includes a preview/end preview button 274 that can be clicked to allow the clinician to preview a stimulation program currently selected within the program database 258 without overwriting the currently activated stimulation program. In this case, the currently activated stimulation program will be stopped and the selected stimulation program will be activated temporarily until the preview/end preview button 274 is clicked again, after which the original stimulation program will be reactivated. The remote screen 100(9) further includes an activate button 276 that can be clicked to overwrite the currently activated stimulation program with a stimulation program selected within the program database 258. Notably, clicking the activate button 276 will provide stimulation energy from the IPG 14 to the electrode array 26 in accordance with the newly activated stimulation program. The remote screen 100(9) further includes an activation/stimulation off button 278 that, like the activate button 276, can be can clicked to overwrite the currently activated stimulation program with a stimulation program selected within the program database 258. However, in this case, stimulation energy is not provided from the IPG 14 to the electrode array 26.

The currently activated stimulation program can be modified or edited in one of two ways. The first way is to click on manual button 110, which opens the manual programming screen 100(6) shown in FIG. 16 to allow the clinician to manually revise the stimulation parameter sets that make up the currently activated stimulation program, including the fractionalized electrode configurations. The remote screen 100(9) includes a renavigation button 280 that provides the second way to modify the currently activated stimulation program.

In particular, the renavigation button 280 can be clicked to provide the coverage areas screen 100(8) illustrated FIG. 24, which includes a list of the coverage areas 234 contained within the currently activated stimulation program. The redo button 240 for one of the coverage areas 234 can be clicked or the navigator button 112 can be clicked to provide the navigator screen 100(7) illustrated in FIG. 23. The fractionalized electrode configurations corresponding to the coverage areas 234 will be generated as marks 228 for display on the navigator scope 202 and placement in the mark list 230. Any of these marks 228 can then be used as a starting point to create other marks by clicking on the corresponding mark designator in the mark list 230, moving the location designator 214 away from the selected mark 228 via manipulation of the directional controls 202-210, and then clicking the mark button 226. These new marks, along with the electrical parameters associated with it (i.e., pulse amplitude, pulse width, and pulse rate), can then be used as initial stimulation parameter sets to program the RC 16 with one or more new stimulation programs in the same manner described above. In particular, an effective stimulation parameter set, which can be selected as the new programmable stimulation set, can be derived from each mark by gradually changing the initial stimulator parameter set to the effective stimulation parameter set while stimulating the patient in accordance with the gradually changing stimulation parameter set, and in particular, by using the navigation table to steer current along and between the leads 12, as discussed above.

Significantly, if the fractionalized electrode configurations corresponding to any of the coverage areas 234 were manually selected by the clinician using the manual programming screen 100(6) illustrated in FIG. 16, it is quite possible that the fractionalized electrode configuration may not identically match a fractionalized electrode configuration found in the navigation table, since manual selection of fractionalized electrode configuration is performed completely independent of the navigation table used in the navigation screen. However, a mark can be still be generated from any mismatched fractionalized electrode configurations manually selected by the clinician and displayed in the navigation scope 202, so that it could be used as a starting point (i.e., the initial fractionalized electrode configuration) in the subsequent navigation procedure. This is accomplished by selecting the fractionalized electrode configuration in the navigation table that best fits the mismatched fractionalized electrode configuration and generating a mark from the selected fractionalized electrode configuration.

In particular, and with reference to FIG. 16, one exemplary methodology employed by the CP 18 to generate a mark from a previously programmed set of stimulation parameters, which in this case, is the stimulation parameter set associated with the stimulation program uploaded from the RC 16 to the CP 18 in response to clicking the remote button 114 and selected in the coverage areas screen 100(8) illustrated in FIG. 24, will now be described. As just discussed above, the previously programmed stimulation parameter set obtained from the RC 16 (and in this case, the fractionalized electrode configuration associated with the previously programmed stimulation parameter set) may not identically match any reference stimulation parameter sets stored in the CP 18 (and in this case, the fractionalized electrode configurations stored in the navigation table).

Figure 26:
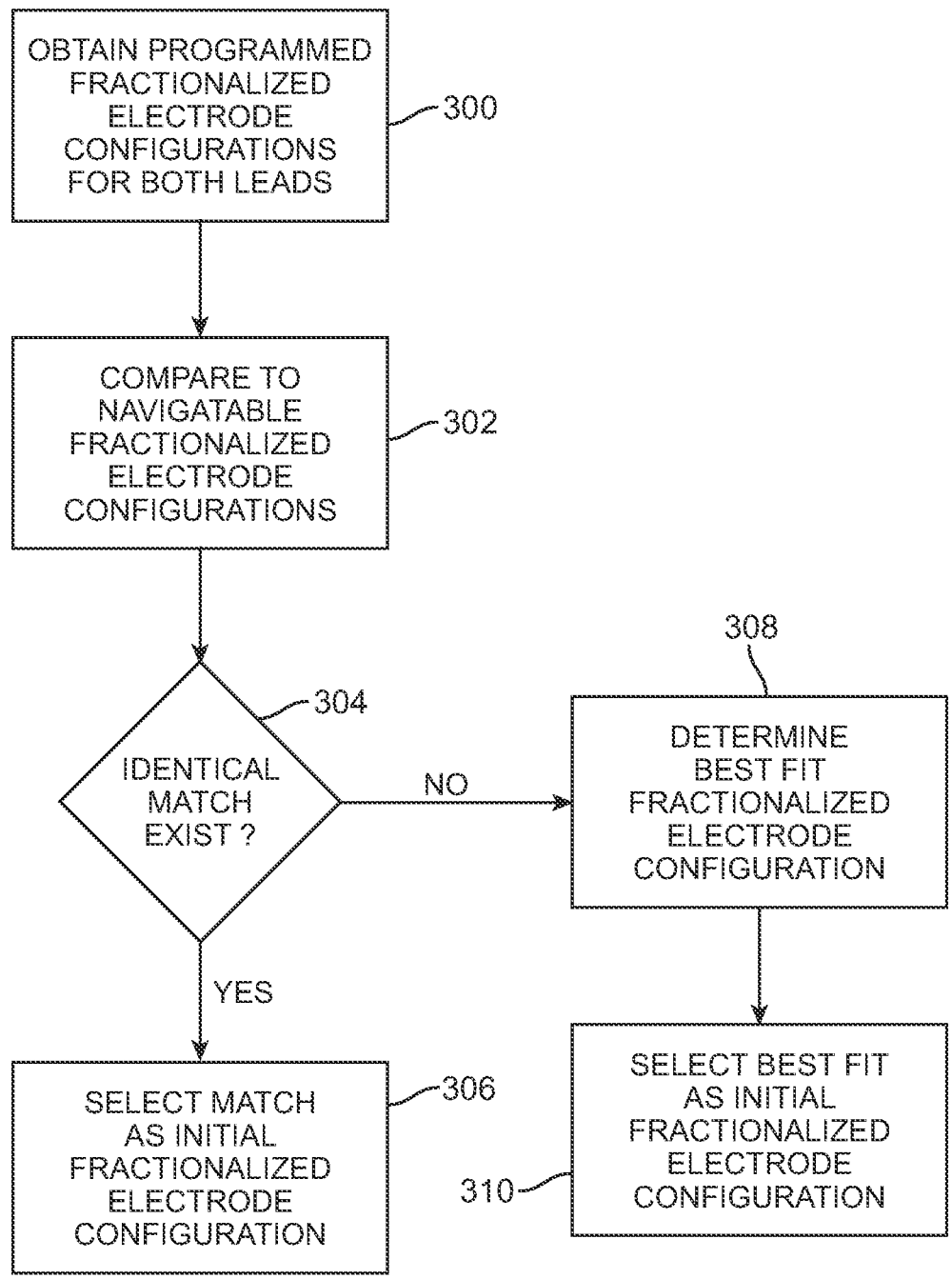
FIG. 26 is a flow diagram showing a methodology used by the computerized programming system of FIG. 6 to generate a mark from a previously programmed fractionalized electrode configuration.

The methodology used by the CP 18 to generate an initial fractionalized electrode configuration for both leads 12 from a previously programmed stimulation parameter set will now be described with reference to FIG. 26. At step 300, the CP 18 obtains the fractionalized electrode configurations for the respective leads 12 from the previously programmed stimulation parameter set (one for electrodes E1-E8 and one for electrodes E9-E16), and at step 302, compares each one to the fractionalized electrode configurations contained in the navigation table (i.e., navigatable fractionalized electrode combinations). At step 304, the CP 18 determines if an identical match between each of the fractionalized electrode configurations and any of the navigatable fractionalized electrode combinations exists. At step 306, if an identical match exists between one of the programmed fractionalized electrode configurations (for either or both leads) and a navigatable electrode configuration, the CP 18 selects the matching fractionalized electrode configuration as an initial fractionalized electrode configuration for that lead.

If an identical match does not exist between one of the programmed fractionalized electrode configurations and a navigatable fractionalized electrode configuration at step 306, the CP 18 determines a best fit between that programmed fractionalized electrode configuration and the navigatable fractionalized electrode configurations at step 308. As will be described in further detail below, the best fit fractionalized electrode configuration can be determined in any one of a number of manners. At step 310, the CP 18 then selects the best fit navigatable fractionalized electrode configuration as an initial fractionalized electrode configuration for that lead. The initial fractionalized electrode combinations for both leads can then be stored as a new mark that can be used to generate a new stimulation program for the remote control 16 and/or IPG 14, as discussed above.

As briefly discussed above, a best fit between a mismatched fractionalized electrode configuration (i.e., a non-navigatable fractionalized electrode configuration) and the fractionalized electrode configurations contained in the navigation table (i.e., the navigatable fractionalized electrode configurations) can be determined in any one of a number of manners.

In one method, the best fit determination is a sorting methodology for prioritizing the electrodes and narrowing the navigatable fractionalized electrode configurations to a single fractionalized electrode configuration based on the electrode prioritization. The electrodes may be prioritized based on any suitable criteria, such as the magnitude of stimulation energy (in this case, electrical current) associated with the electrodes and/or the polarities independently associated with the electrodes. For example, it is known that for SCS applications, the electrodes that affect stimulation the most are the cathodes having the highest current. Based on this, the electrodes on each lead may be prioritized in accordance with the following criteria:
1) cathode with the $1^{st}$ highest current;
2) cathode with the $2^{nd}$ highest current;
3) cathode with the $3^{rd}$ highest current;
4) cathode with the $4^{th}$ highest current;
5) anode with the $1^{st}$ highest current;
6) anode with the $2^{nd}$ highest current;
7) anode with the $3^{rd}$ highest current;
8) anode with the $4^{th}$ highest current.

The fractionalized electrode configurations can be narrowed, e.g., by determining a first set of the navigatable fractionalized electrode configurations that best match the non-navigatable fractionalized electrode configuration for the highest priority electrode, determining a next set of the navigatable fractionalized electrode configurations from the first set that best match the non-navigatable fractionalized electrode configuration for the next highest priority electrode, and so forth.

For example, the navigatable fractionalized electrode configurations that best match the cathode with the $1^{st}$ highest current in the non-navigatable fractionalized electrode configuration will be determined, then from these, the navigatable fractionalized electrode configurations that best match the cathode with the 2nd highest current in the non-navigatable fractionalized electrode configuration will be determined, then from these, the navigatable fractionalized electrode configurations that best match the cathode with the 3rd highest current in the non-navigatable fractionalized electrode configuration will be determined, and then from these, the navigatable fractionalized electrode configurations that best match the cathode with the 4th highest current in the non-navigatable fractionalized electrode configuration will be determined.

From these remaining navigatable fractionalized electrode configurations, the navigatable fractionalized electrode configurations that best match the anode with the 1st highest current in the non-navigatable fractionalized electrode configuration will be determined, then from these, the navigatable fractionalized electrode configurations that best match the cathode with the 2nd highest current in the non-navigatable fractionalized electrode configuration will be determined, and then from these, the navigatable fractionalized electrode configurations that best match the cathode with the 3rd highest current in the non-navigatable fractionalized electrode configuration will be determined, and then from these, the navigatable fractionalized electrode configuration that best matches the cathode with the 4th highest current in the non-navigatable fractionalized electrode configuration will be determined.

As one example, assume that the non-navigatable fractionalized electrode configuration is defined by electrodes E2 having a cathodic current of 43%, E3 having a cathodic current of 57%, E7 as having an anodic current of 55%, and E8 as having an anodic current of 45%, which is then compared with the fractionalized electrode configurations contained in the navigation table of Appendix A. The cathode with the $1^{st}$ highest current is E3 at 57%, and thus, fractionalized electrode configurations 112 and 190 are selected, since they both define a fractionalized current of 55% for electrode E3. The cathode with the $2^{nd}$ highest current is E2 at 43%, and thus, fractionalized electrode configuration 112 is selected, since it is the only one that defines any current for electrode E2 at 45%. Thus, fractionalized electrode configuration 112 will be selected as the best fit for the non-navigatable fractionalized electrode configuration, defining electrode E2 to have a cathodic current of 45%, electrode E3 to have a cathodic current of 55%, electrode E5 to have an anodic current of 45%, and electrode E8 to have an anodic current of 55%.

In another method, the best fit determination comprises deriving a first set of data points from the non-navigatable fractionalized electrode configuration, deriving a second set of data points from each of the navigatable fractionalized electrode configurations, computationally comparing the first set of data points with each of the second set of data points, and determining the navigatable fractionalized electrode configuration as the best fit based on the computational comparison.

Figure 27:
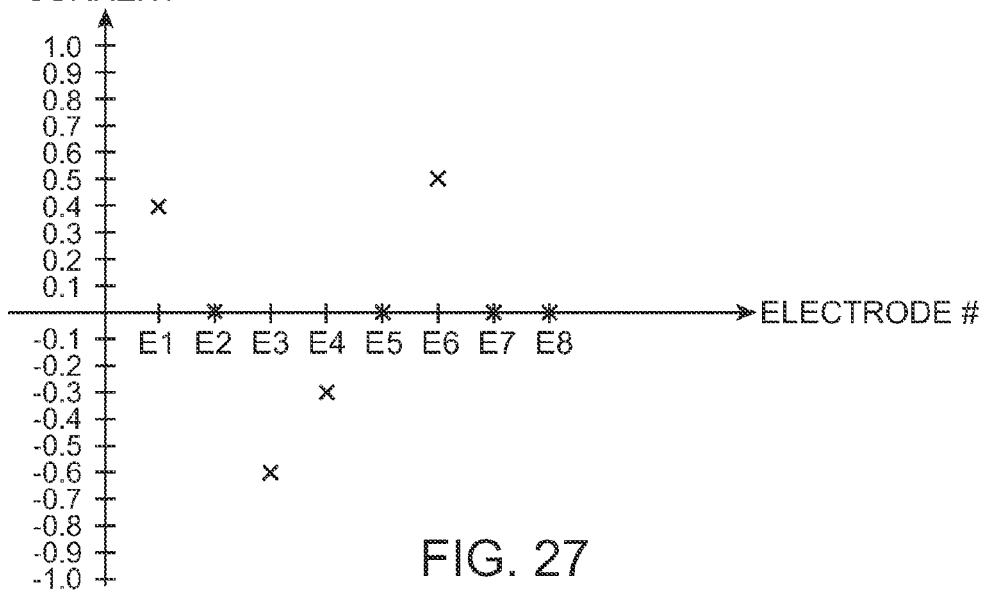
FIG. 27 is a plot of data points representing the fractionalized current values for the respective electrodes of a lead.
Figure 28:
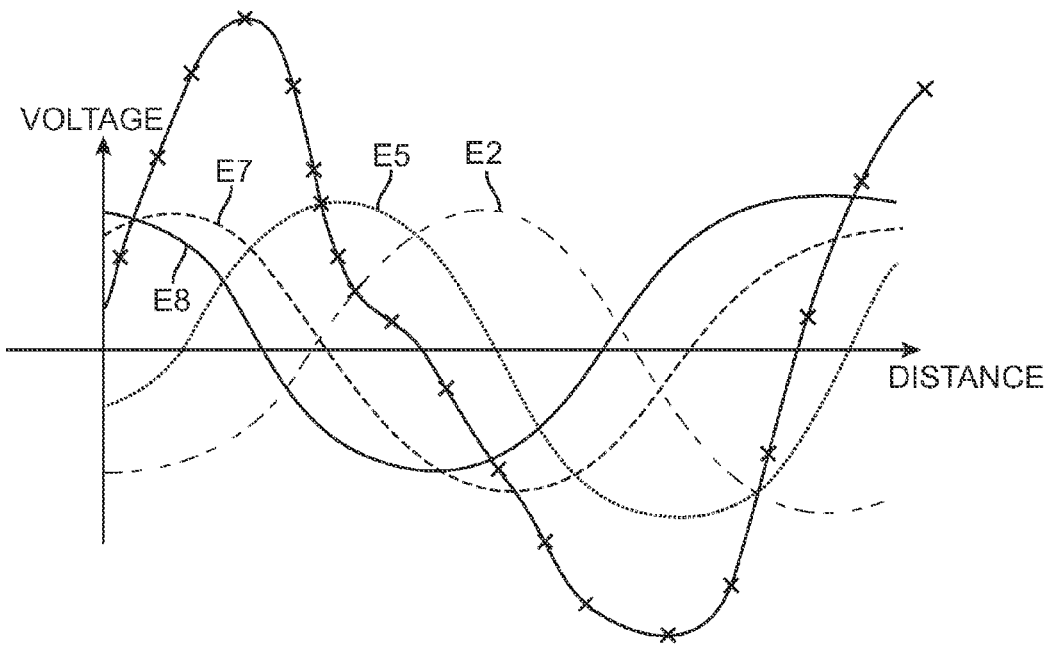
FIG. 28 is a plot of data points representing voltage values as a function of a neural activation function of the electrodes of a lead.

The data points can represent any characteristic that would provide a sufficient indication of best fit between fractionalized electrode configurations with respect to the effects of the stimulation energy experienced by the patient. As one example, each data point may represent a magnitude of stimulation energy (in this case, a fractionalized current value) associated with a respective one of the electrodes. For example, FIG. 27 illustrates a plurality of data points representing the fractionalized current values of navigatable fractionalized electrode configuration 188 from the navigation table of Appendix A. As there shown, the data points for electrodes E1-E8 are respectively 0.35, 0, −0.65, −0.35, 0, 0.65, 0, 0, and 0. As another example, each data point may represent a voltage as a neural activation function of the electrode array 26. For example, FIG. 28 illustrates a voltage waveform (shown in dashed lines) generated by navigatable fractionalized electrode configuration 188 along a spinal cord, with the composite of the voltage waveforms (shown in solid) being considered the neural activation function. As shown, data points can then be plotted along the neural activation function.

The first data point set (i.e., the data points derived from the non-navigatable fractionalized electrode configuration) can be computationally compared to each of the second data point sets (i.e., the data points derived from the navigatable fractionalized electrode configurations) in any one of a variety of manners; for example by using a comparison function that returns a value indicative of the best fit navigatable fractionalized electrode configuration.

For example, one comparison function that can be used is a correlation coefficient function, such as a Pearson Correlation Coefficient function, which can be expressed as the following equation:

$$r = \frac{\sum_i (FIR_i - M_{FIR})(SEC_i - M_{SEC})}{sqrt\left(\sum_i (FIR_i - M_{FIR}) \sum_i (SEC_i - M_{SEC})^2\right)}, \text{ where}$$

r is the coefficient, FIR represents the data derived from the non-navigatable fractionalized electrode configuration (i.e., the first data set), SEC represents the data derived from a navigatable fractionalized electrode configuration (i.e., one of the second data sets), M represents the mean of the data set (either first or second), and i represents a single element of the data set (either first or second). Advantageously, the correlation coefficient is not sensitive to magnitude scaling, and ranges from −1 (perfect inverse correlation) to 1 (perfect correlation). With this function, the navigatable fractionalized electrode configuration that results in the maximum coefficient is the one that is selected as the best fit for the programmable fractionalized electrode configuration.

Another comparison function that can be used is a least squares based function, and in particular, a sum of squared differences function, which can be expressed as the following equation:

$$SSD = \sum_i ((FIR_i - SEC_i)^2), \text{ where}$$

SSD is the sum of squared difference, and FIR, SEC, and i have been defined above. The SSD function measures the difference between the actual data and an instance of the model-based estimate of the data. With this function, the navigatable fractionalized electrode configuration that results in the minimum sum of squared difference is the one that is selected as the best fit for the programmable fractionalized electrode configuration.

Other comparison functions, including cross-correlation functions, wavelet functions, and associated matching measures, may be alternatively used.

It should be noted that the data sets may be derived from a subset of the electrodes before initially performing the computation function. For example, the first data set may be derived from only the cathodes of the non-navigatable fractionalized electrode configuration, and each of the second data sets may be derived from only the cathodes of the navigatable fractionalized electrode configurations. In addition to decreasing the data needed to be processed, and therefore the processing time, the data that has the greatest impact on stimulation can be focused on, while ignoring insignificant data, thereby increasing the chances that the navigatable fractionalized electrode configuration that returns the best computational value (maximum coefficient in the case of a Pearson Correlation Coefficient function or minimal value in the case of the sum of squared differences function) is truly the best fit for the programmable fractionalized electrode configuration.

It should be noted that, in the case of a tie (i.e., there are multiple navigatable fractionalized electrode configurations associated with the best computational vale), the best fit can be selected arbitrarily from these navigatable fractionalized electrode configurations, or a tie-breaking function, can be used.

For example, if the comparison function initially took into account all of the electrodes, the performance of a tie breaking function may comprise deriving the first data set only from the cathodes of the non-navigatable fractionalized electrode configuration and deriving the second data sets only from the navigatable fractionalized electrode configurations that are tied. As another example, if the comparison function initially took into account only a subset of the electrodes (such as only the cathodes), the performance of a tie breaking function may comprise deriving the first data set from all of the electrodes of the non-navigatable fractionalized electrode configuration and deriving the second data sets from all of the electrodes of the navigatable fractionalized electrode configurations that are tied. As still another example, if the data points represent the fractionalized current values of the electrodes, the performance of the tie breaking function can comprise performing a comparison function on data points representing the voltage as a neural activation function of the electrodes with respect to the navigatable fractionalized electrode configurations that are tied, or vice versa.

In either of these cases, the computational comparison function is then performed on the data sets, and the navigatable fractionalized electrode configuration that results in the best computational value is the one that is ultimately selected as the best fit for the non-navigatable fractionalized electrode configuration.

Notably, to the extent that a steering table of absolute electrical current values (as opposed to fractionalized electrical current values) is used (such as may be used when gradually shifting current using time-interleaved pulses, as described above), the comparison and matching functions described above will be performed on absolute electrical current values as opposed to fractionalized electrical current values. Furthermore, to the extent that a steering table of electrical voltage values (as opposed to electrical current values) is used, such as may be used in voltage-regulated systems, the comparison and matching functions described above will be performed on electrical voltage values as opposed to electrical current values.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

APPENDIX A

Simplified Steering Table

| Stim# | Electrode# | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| 1 | −1 | 0 | 0 | 0 | 0 | 0 | 0.5 | 0.5 | 0 | 0 | 0 | 0 | 0 | 0 | 0 | 0 |
| 2 | −1 | 0 | 0.05 | 0 | 0 | 0 | 0.45 | 0.5 | 0 | 0 | 0 | 0 | 0 | 0 | 0 | 0 |
| 3 | −1 | 0 | 0.1 | 0 | 0 | 0 | 0.4 | 0.5 | 0 | 0 | 0 | 0 | 0 | 0 | 0 | 0 |

APPENDIX A-continued

Simplified Steering Table

| Stim# | Electrode# | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| 4 | −1 | 0 | 0.15 | 0 | 0 | 0 | 0.4 | 0.45 | 0 | 0 | 0 | 0 | 0 | 0 | 0 | 0 |
| 5 | −1 | 0 | 0.2 | 0 | 0 | 0 | 0.4 | 0.4 | 0 | 0 | 0 | 0 | 0 | 0 | 0 | 0 |
| 6 | −1 | 0 | 0.25 | 0 | 0 | 0 | 0.35 | 0.4 | 0 | 0 | 0 | 0 | 0 | 0 | 0 | 0 |
| 7 | −1 | 0 | 0.3 | 0 | 0 | 0 | 0.3 | 0.4 | 0 | 0 | 0 | 0 | 0 | 0 | 0 | 0 |
| 8 | −1 | 0 | 0.35 | 0 | 0 | 0 | 0.3 | 0.35 | 0 | 0 | 0 | 0 | 0 | 0 | 0 | 0 |
| 9 | −1 | 0 | 0.4 | 0 | 0 | 0 | 0.3 | 0.3 | 0 | 0 | 0 | 0 | 0 | 0 | 0 | 0 |
| 10 | −1 | 0 | 0.45 | 0 | 0 | 0 | 0.25 | 0.3 | 0 | 0 | 0 | 0 | 0 | 0 | 0 | 0 |
| 11 | −1 | 0 | 0.5 | 0 | 0 | 0 | 0.2 | 0.3 | 0 | 0 | 0 | 0 | 0 | 0 | 0 | 0 |
| 12 | −1 | 0 | 0.55 | 0 | 0 | 0 | 0.2 | 0.25 | 0 | 0 | 0 | 0 | 0 | 0 | 0 | 0 |
| 13 | −1 | 0 | 0.6 | 0 | 0 | 0 | 0.2 | 0.2 | 0 | 0 | 0 | 0 | 0 | 0 | 0 | 0 |
| 14 | −1 | 0 | 0.65 | 0 | 0 | 0 | 0.15 | 02 | 0 | 0 | 0 | 0 | 0 | 0 | 0 | 0 |
| 15 | −1 | 0 | 0.7 | 0 | 0 | 0 | 0.1 | 0.2 | 0 | 0 | 0 | 0 | 0 | 0 | 0 | 0 |
| 16 | −1 | 0 | 0.75 | 0 | 0 | 0 | 0.1 | 0.15 | 0 | 0 | 0 | 0 | 0 | 0 | 0 | 0 |
| 17 | −1 | 0 | 0.8 | 0 | 0 | 0 | 0.1 | 0.1 | 0 | 0 | 0 | 0 | 0 | 0 | 0 | 0 |
| 18 | −1 | 0 | 0.85 | 0 | 0 | 0 | 0.05 | 0.1 | 0 | 0 | 0 | 0 | 0 | 0 | 0 | 0 |
| 19 | −1 | 0 | 0.9 | 0 | 0 | 0 | 0 | 0.1 | 0 | 0 | 0 | 0 | 0 | 0 | 0 | 0 |
| 20 | −1 | 0 | 0.95 | 0 | 0 | 0 | 0 | 0.05 | 0 | 0 | 0 | 0 | 0 | 0 | 0 | 0 |
| 21 | −1 | 0 | 1 | 0 | 0 | 0 | 0 | 0 | 0 | 0 | 0 | 0 | 0 | 0 | 0 | 0 |
| 22 | −1 | 0 | 0.95 | 0.05 | 0 | 0 | 0 | 0 | 0 | 0 | 0 | 0 | 0 | 0 | 0 | 0 |
| 23 | −1 | 0 | 0.9 | 0.1 | 0 | 0 | 0 | 0 | 0 | 0 | 0 | 0 | 0 | 0 | 0 | 0 |
| 24 | −1 | 0 | 0.85 | 0.15 | 0 | 0 | 0 | 0 | 0 | 0 | 0 | 0 | 0 | 0 | 0 | 0 |
| 25 | −1 | 0 | 0.8 | 0.2 | 0 | 0 | 0 | 0 | 0 | 0 | 0 | 0 | 0 | 0 | 0 | 0 |
| 26 | −1 | 0 | 0.75 | 0.25 | 0 | 0 | 0 | 0 | 0 | 0 | 0 | 0 | 0 | 0 | 0 | 0 |
| 27 | −1 | 0 | 0.7 | 0.3 | 0 | 0 | 0 | 0 | 0 | 0 | 0 | 0 | 0 | 0 | 0 | 0 |
| 28 | −1 | 0 | 0.65 | 0.35 | 0 | 0 | 0 | 0 | 0 | 0 | 0 | 0 | 0 | 0 | 0 | 0 |
| 29 | −1 | 0 | 0.6 | 0.4 | 0 | 0 | 0 | 0 | 0 | 0 | 0 | 0 | 0 | 0 | 0 | 0 |
| 30 | −1 | 0 | 0.55 | 0.45 | 0 | 0 | 0 | 0 | 0 | 0 | 0 | 0 | 0 | 0 | 0 | 0 |
| 31 | −1 | 0 | 0.5 | 0.5 | 0 | 0 | 0 | 0 | 0 | 0 | 0 | 0 | 0 | 0 | 0 | 0 |
| 32 | −1 | 0 | 0.45 | 0.55 | 0 | 0 | 0 | 0 | 0 | 0 | 0 | 0 | 0 | 0 | 0 | 0 |
| 33 | −1 | 0 | 0.4 | 0.6 | 0 | 0 | 0 | 0 | 0 | 0 | 0 | 0 | 0 | 0 | 0 | 0 |
| 34 | −1 | 0 | 0.35 | 0.65 | 0 | 0 | 0 | 0 | 0 | 0 | 0 | 0 | 0 | 0 | 0 | 0 |
| 35 | −1 | 0 | 0.3 | 0.7 | 0 | 0 | 0 | 0 | 0 | 0 | 0 | 0 | 0 | 0 | 0 | 0 |
| 36 | −1 | 0 | 0.25 | 0.75 | 0 | 0 | 0 | 0 | 0 | 0 | 0 | 0 | 0 | 0 | 0 | 0 |
| 37 | −1 | 0 | 0.2 | 0.8 | 0 | 0 | 0 | 0 | 0 | 0 | 0 | 0 | 0 | 0 | 0 | 0 |
| 38 | −1 | 0 | 0.15 | 0.85 | 0 | 0 | 0 | 0 | 0 | 0 | 0 | 0 | 0 | 0 | 0 | 0 |
| 39 | −1 | 0 | 0.1 | 0.9 | 0 | 0 | 0 | 0 | 0 | 0 | 0 | 0 | 0 | 0 | 0 | 0 |
| 40 | −1 | 0 | 0.05 | 0.95 | 0 | 0 | 0 | 0 | 0 | 0 | 0 | 0 | 0 | 0 | 0 | 0 |
| 41 | −1 | 0 | 0 | 1 | 0 | 0 | 0 | 0 | 0 | 0 | 0 | 0 | 0 | 0 | 0 | 0 |
| 42 | −0.95 | −0.05 | 0 | 0.95 | 0 | 0 | 0 | 0.05 | 0 | 0 | 0 | 0 | 0 | 0 | 0 | 0 |
| 43 | −0.9 | −0.1 | 0 | 0.9 | 0 | 0 | 0 | 0.1 | 0 | 0 | 0 | 0 | 0 | 0 | 0 | 0 |
| 44 | −0.85 | −0.15 | 0 | 0.85 | 0 | 0 | 0 | 0.15 | 0 | 0 | 0 | 0 | 0 | 0 | 0 | 0 |
| 45 | −0.8 | −0.2 | 0 | 0.8 | 0 | 0 | 0 | 0.2 | 0 | 0 | 0 | 0 | 0 | 0 | 0 | 0 |
| 46 | −0.75 | −0.25 | 0 | 0.75 | 0 | 0 | 0 | 0.25 | 0 | 0 | 0 | 0 | 0 | 0 | 0 | 0 |
| 47 | −0.7 | −0.3 | 0 | 0.7 | 0 | 0 | 0 | 0.3 | 0 | 0 | 0 | 0 | 0 | 0 | 0 | 0 |
| 48 | −0.65 | −0.35 | 0 | 0.65 | 0 | 0 | 0 | 0.35 | 0 | 0 | 0 | 0 | 0 | 0 | 0 | 0 |
| 49 | −0.6 | −0.4 | 0 | 0.6 | 0 | 0 | 0 | 0.4 | 0 | 0 | 0 | 0 | 0 | 0 | 0 | 0 |
| 50 | −0.55 | −0.45 | 0 | 0.55 | 0 | 0 | 0 | 0.45 | 0 | 0 | 0 | 0 | 0 | 0 | 0 | 0 |
| 51 | −0.5 | −0.5 | 0 | 0.5 | 0 | 0 | 0 | 0.5 | 0 | 0 | 0 | 0 | 0 | 0 | 0 | 0 |
| 52 | −0.45 | −0.55 | 0 | 0.45 | 0 | 0 | 0 | 0.55 | 0 | 0 | 0 | 0 | 0 | 0 | 0 | 0 |
| 53 | −0.4 | −0.6 | 0 | 0.4 | 0 | 0 | 0 | 0.6 | 0 | 0 | 0 | 0 | 0 | 0 | 0 | 0 |
| 54 | −0.35 | −0.65 | 0 | 0.35 | 0 | 0 | 0 | 0.65 | 0 | 0 | 0 | 0 | 0 | 0 | 0 | 0 |
| 55 | −0.3 | −0.7 | 0 | 0.3 | 0 | 0 | 0 | 0.7 | 0 | 0 | 0 | 0 | 0 | 0 | 0 | 0 |
| 56 | −0.25 | −0.75 | 0 | 0.25 | 0 | 0 | 0 | 0.75 | 0 | 0 | 0 | 0 | 0 | 0 | 0 | 0 |
| 57 | −0.2 | −0.8 | 0 | 0.2 | 0 | 0 | 0 | 0.8 | 0 | 0 | 0 | 0 | 0 | 0 | 0 | 0 |
| 58 | −0.15 | −0.85 | 0 | 0.15 | 0 | 0 | 0 | 0.85 | 0 | 0 | 0 | 0 | 0 | 0 | 0 | 0 |
| 59 | −0.1 | −0.9 | 0 | 0.1 | 0 | 0 | 0 | 0.9 | 0 | 0 | 0 | 0 | 0 | 0 | 0 | 0 |
| 60 | −0.05 | −0.95 | 0 | 0.05 | 0 | 0 | 0 | 0.95 | 0 | 0 | 0 | 0 | 0 | 0 | 0 | 0 |
| 61 | 0 | −1 | 0 | 0 | 0 | 0 | 0 | 1 | 0 | 0 | 0 | 0 | 0 | 0 | 0 | 0 |
| 62 | 0 | −1 | 0 | 0.05 | 0 | 0 | 0 | 0.95 | 0 | 0 | 0 | 0 | 0 | 0 | 0 | 0 |
| 63 | 0 | −1 | 0 | 0.1 | 0 | 0 | 0 | 0.9 | 0 | 0 | 0 | 0 | 0 | 0 | 0 | 0 |
| 64 | 0 | −1 | 0 | 0.15 | 0 | 0 | 0 | 0.85 | 0 | 0 | 0 | 0 | 0 | 0 | 0 | 0 |
| 65 | 0 | −1 | 0 | 0.2 | 0 | 0 | 0 | 0.8 | 0 | 0 | 0 | 0 | 0 | 0 | 0 | 0 |
| 66 | 0 | −1 | 0 | 0.25 | 0 | 0 | 0 | 0.75 | 0 | 0 | 0 | 0 | 0 | 0 | 0 | 0 |
| 67 | 0 | −1 | 0 | 0.3 | 0 | 0 | 0 | 0.7 | 0 | 0 | 0 | 0 | 0 | 0 | 0 | 0 |
| 68 | 0 | −1 | 0 | 0.35 | 0 | 0 | 0 | 0.65 | 0 | 0 | 0 | 0 | 0 | 0 | 0 | 0 |
| 69 | 0 | −1 | 0 | 0.4 | 0 | 0 | 0 | 0.6 | 0 | 0 | 0 | 0 | 0 | 0 | 0 | 0 |
| 70 | 0 | −1 | 0 | 0.45 | 0 | 0 | 0 | 0.55 | 0 | 0 | 0 | 0 | 0 | 0 | 0 | 0 |
| 71 | 0 | −1 | 0 | 0.5 | 0 | 0 | 0 | 0.5 | 0 | 0 | 0 | 0 | 0 | 0 | 0 | 0 |
| 72 | 0 | −1 | 0 | 0.55 | 0 | 0 | 0 | 0.45 | 0 | 0 | 0 | 0 | 0 | 0 | 0 | 0 |
| 73 | 0 | −1 | 0 | 0.6 | 0 | 0 | 0 | 0.4 | 0 | 0 | 0 | 0 | 0 | 0 | 0 | 0 |
| 74 | 0 | −1 | 0 | 0.65 | 0 | 0 | 0 | 0.35 | 0 | 0 | 0 | 0 | 0 | 0 | 0 | 0 |
| 75 | 0 | −1 | 0 | 0.7 | 0 | 0 | 0 | 0.3 | 0 | 0 | 0 | 0 | 0 | 0 | 0 | 0 |
| 76 | 0 | −1 | 0 | 0.75 | 0 | 0 | 0 | 0.25 | 0 | 0 | 0 | 0 | 0 | 0 | 0 | 0 |
| 77 | 0 | −1 | 0 | 0.8 | 0 | 0 | 0 | 0.2 | 0 | 0 | 0 | 0 | 0 | 0 | 0 | 0 |

APPENDIX A-continued

Simplified Steering Table

| Stim# | Electrode# | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| 78 | 0 | −1 | 0 | 0.85 | 0 | 0 | 0 | 0.15 | 0 | 0 | 0 | 0 | 0 | 0 | 0 | 0 |
| 79 | 0 | −1 | 0 | 0.9 | 0 | 0 | 0 | 0.1 | 0 | 0 | 0 | 0 | 0 | 0 | 0 | 0 |
| 80 | 0 | −1 | 0 | 0.95 | 0 | 0 | 0 | 0.05 | 0 | 0 | 0 | 0 | 0 | 0 | 0 | 0 |
| 81 | 0 | −1 | 0 | 1 | 0 | 0 | 0 | 0 | 0 | 0 | 0 | 0 | 0 | 0 | 0 | 0 |
| 82 | 0 | −1 | 0 | 0.95 | 0.05 | 0 | 0 | 0 | 0 | 0 | 0 | 0 | 0 | 0 | 0 | 0 |
| 83 | 0 | −1 | 0 | 0.9 | 0.1 | 0 | 0 | 0 | 0 | 0 | 0 | 0 | 0 | 0 | 0 | 0 |
| 84 | 0 | −1 | 0 | 0.85 | 0.15 | 0 | 0 | 0 | 0 | 0 | 0 | 0 | 0 | 0 | 0 | 0 |
| 85 | 0 | −1 | 0 | 0.8 | 0.2 | 0 | 0 | 0 | 0 | 0 | 0 | 0 | 0 | 0 | 0 | 0 |
| 86 | 0 | −1 | 0 | 0.75 | 0.25 | 0 | 0 | 0 | 0 | 0 | 0 | 0 | 0 | 0 | 0 | 0 |
| 87 | 0 | −1 | 0 | 0.7 | 0.3 | 0 | 0 | 0 | 0 | 0 | 0 | 0 | 0 | 0 | 0 | 0 |
| 88 | 0 | −1 | 0 | 0.65 | 0.35 | 0 | 0 | 0 | 0 | 0 | 0 | 0 | 0 | 0 | 0 | 0 |
| 89 | 0 | −1 | 0 | 0.6 | 0.4 | 0 | 0 | 0 | 0 | 0 | 0 | 0 | 0 | 0 | 0 | 0 |
| 90 | 0 | −1 | 0 | 0.55 | 0.45 | 0 | 0 | 0 | 0 | 0 | 0 | 0 | 0 | 0 | 0 | 0 |
| 91 | 0 | −1 | 0 | 0.5 | 0.5 | 0 | 0 | 0 | 0 | 0 | 0 | 0 | 0 | 0 | 0 | 0 |
| 92 | 0 | −1 | 0 | 0.45 | 0.55 | 0 | 0 | 0 | 0 | 0 | 0 | 0 | 0 | 0 | 0 | 0 |
| 93 | 0 | −1 | 0 | 0.4 | 0.6 | 0 | 0 | 0 | 0 | 0 | 0 | 0 | 0 | 0 | 0 | 0 |
| 94 | 0 | −1 | 0 | 0.35 | 0.65 | 0 | 0 | 0 | 0 | 0 | 0 | 0 | 0 | 0 | 0 | 0 |
| 95 | 0 | −1 | 0 | 0.3 | 0.7 | 0 | 0 | 0 | 0 | 0 | 0 | 0 | 0 | 0 | 0 | 0 |
| 96 | 0 | −1 | 0 | 0.25 | 0.75 | 0 | 0 | 0 | 0 | 0 | 0 | 0 | 0 | 0 | 0 | 0 |
| 97 | 0 | −1 | 0 | 0.2 | 0.8 | 0 | 0 | 0 | 0 | 0 | 0 | 0 | 0 | 0 | 0 | 0 |
| 98 | 0 | −1 | 0 | 0.15 | 0.85 | 0 | 0 | 0 | 0 | 0 | 0 | 0 | 0 | 0 | 0 | 0 |
| 99 | 0 | −1 | 0 | 0.1 | 0.9 | 0 | 0 | 0 | 0 | 0 | 0 | 0 | 0 | 0 | 0 | 0 |
| 100 | 0 | −1 | 0 | 0.05 | 0.95 | 0 | 0 | 0 | 0 | 0 | 0 | 0 | 0 | 0 | 0 | 0 |
| 101 | 0 | −1 | 0 | 0 | 1 | 0 | 0 | 0 | 0 | 0 | 0 | 0 | 0 | 0 | 0 | 0 |
| 102 | 0 | −0.95 | −0.05 | 0 | 0.95 | 0 | 0 | 0.05 | 0 | 0 | 0 | 0 | 0 | 0 | 0 | 0 |
| 103 | 0 | −0.9 | −0.1 | 0 | 0.9 | 0 | 0 | 0.1 | 0 | 0 | 0 | 0 | 0 | 0 | 0 | 0 |
| 104 | 0 | −0.85 | −0.15 | 0 | 0.85 | 0 | 0 | 0.15 | 0 | 0 | 0 | 0 | 0 | 0 | 0 | 0 |
| 105 | 0 | −0.8 | −0.2 | 0 | 0.8 | 0 | 0 | 0.2 | 0 | 0 | 0 | 0 | 0 | 0 | 0 | 0 |
| 106 | 0 | −0.75 | −0.25 | 0 | 0.75 | 0 | 0 | 0.25 | 0 | 0 | 0 | 0 | 0 | 0 | 0 | 0 |
| 107 | 0 | −0.7 | −0.3 | 0 | 0.7 | 0 | 0 | 0.3 | 0 | 0 | 0 | 0 | 0 | 0 | 0 | 0 |
| 108 | 0 | −0.65 | −0.35 | 0 | 0.65 | 0 | 0 | 0.35 | 0 | 0 | 0 | 0 | 0 | 0 | 0 | 0 |
| 109 | 0 | −0.6 | −0.4 | 0 | 0.6 | 0 | 0 | 0.4 | 0 | 0 | 0 | 0 | 0 | 0 | 0 | 0 |
| 110 | 0 | −0.55 | −0.45 | 0 | 0.55 | 0 | 0 | 0.45 | 0 | 0 | 0 | 0 | 0 | 0 | 0 | 0 |
| 111 | 0 | −0.5 | −0.5 | 0 | 0.5 | 0 | 0 | 0.5 | 0 | 0 | 0 | 0 | 0 | 0 | 0 | 0 |
| 112 | 0 | −0.45 | −0.55 | 0 | 0.45 | 0 | 0 | 0.55 | 0 | 0 | 0 | 0 | 0 | 0 | 0 | 0 |
| 113 | 0 | −0.4 | −0.6 | 0 | 0.4 | 0 | 0 | 0.6 | 0 | 0 | 0 | 0 | 0 | 0 | 0 | 0 |
| 114 | 0 | −0.35 | −0.65 | 0 | 0.35 | 0 | 0 | 0.65 | 0 | 0 | 0 | 0 | 0 | 0 | 0 | 0 |
| 115 | 0 | −0.3 | −0.7 | 0 | 0.3 | 0 | 0 | 0.7 | 0 | 0 | 0 | 0 | 0 | 0 | 0 | 0 |
| 116 | 0 | −0.25 | −0.75 | 0 | 0.25 | 0 | 0 | 0.75 | 0 | 0 | 0 | 0 | 0 | 0 | 0 | 0 |
| 117 | 0 | −0.2 | −0.8 | 0 | 0.2 | 0 | 0 | 0.8 | 0 | 0 | 0 | 0 | 0 | 0 | 0 | 0 |
| 118 | 0 | −0.15 | −0.85 | 0 | 0.15 | 0 | 0 | 0.85 | 0 | 0 | 0 | 0 | 0 | 0 | 0 | 0 |
| 119 | 0 | −0.1 | −0.9 | 0 | 0.1 | 0 | 0 | 0.9 | 0 | 0 | 0 | 0 | 0 | 0 | 0 | 0 |
| 120 | 0 | −0.05 | −0.95 | 0 | 0.05 | 0 | 0 | 0.95 | 0 | 0 | 0 | 0 | 0 | 0 | 0 | 0 |
| 121 | 0 | 0 | −1 | 0 | 0 | 0 | 0 | 1 | 0 | 0 | 0 | 0 | 0 | 0 | 0 | 0 |
| 122 | 0.5 | 0 | −1 | 0 | 0 | 0 | 0 | 0.95 | 0 | 0 | 0 | 0 | 0 | 0 | 0 | 0 |
| 123 | 0.1 | 0 | −1 | 0 | 0 | 0 | 0 | 0.8 | 0 | 0 | 0 | 0 | 0 | 0 | 0 | 0 |
| 124 | 0.15 | 0 | −1 | 0 | 0 | 0 | 0 | 0.85 | 0 | 0 | 0 | 0 | 0 | 0 | 0 | 0 |
| 125 | 0.2 | 0 | −1 | 0 | 0 | 0 | 0 | 0.8 | 0 | 0 | 0 | 0 | 0 | 0 | 0 | 0 |
| 126 | 0.25 | 0 | −1 | 0 | 0 | 0 | 0 | 0.75 | 0 | 0 | 0 | 0 | 0 | 0 | 0 | 0 |
| 127 | 0.3 | 0 | −1 | 0 | 0 | 0 | 0 | 0.7 | 0 | 0 | 0 | 0 | 0 | 0 | 0 | 0 |
| 128 | 0.35 | 0 | −1 | 0 | 0 | 0 | 0 | 0.65 | 0 | 0 | 0 | 0 | 0 | 0 | 0 | 0 |
| 129 | 0.4 | 0 | −1 | 0 | 0 | 0 | 0 | 0.6 | 0 | 0 | 0 | 0 | 0 | 0 | 0 | 0 |
| 130 | 0.45 | 0 | −1 | 0 | 0 | 0 | 0 | 0.55 | 0 | 0 | 0 | 0 | 0 | 0 | 0 | 0 |
| 131 | 0.5 | 0 | −1 | 0 | 0 | 0 | 0 | 0.5 | 0 | 0 | 0 | 0 | 0 | 0 | 0 | 0 |
| 132 | 0.55 | 0 | −1 | 0 | 0 | 0 | 0 | 0.45 | 0 | 0 | 0 | 0 | 0 | 0 | 0 | 0 |
| 133 | 0.6 | 0 | −1 | 0 | 0 | 0 | 0 | 0.4 | 0 | 0 | 0 | 0 | 0 | 0 | 0 | 0 |
| 134 | 0.65 | 0 | −1 | 0 | 0 | 0 | 0 | 0.35 | 0 | 0 | 0 | 0 | 0 | 0 | 0 | 0 |
| 135 | 0.7 | 0 | −1 | 0 | 0 | 0 | 0 | 0.3 | 0 | 0 | 0 | 0 | 0 | 0 | 0 | 0 |
| 136 | 0.75 | 0 | −1 | 0 | 0 | 0 | 0 | 0.25 | 0 | 0 | 0 | 0 | 0 | 0 | 0 | 0 |
| 137 | 0.8 | 0 | −1 | 0 | 0 | 0 | 0 | 0.2 | 0 | 0 | 0 | 0 | 0 | 0 | 0 | 0 |
| 138 | 0.85 | 0 | −1 | 0 | 0 | 0 | 0 | 0.15 | 0 | 0 | 0 | 0 | 0 | 0 | 0 | 0 |
| 139 | 0.9 | 0 | −1 | 0 | 0 | 0 | 0 | 0.1 | 0 | 0 | 0 | 0 | 0 | 0 | 0 | 0 |
| 140 | 0.95 | 0 | −1 | 0 | 0 | 0 | 0 | 0.05 | 0 | 0 | 0 | 0 | 0 | 0 | 0 | 0 |
| 141 | 1 | 0 | −1 | 0 | 0 | 0 | 0 | 0 | 0 | 0 | 0 | 0 | 0 | 0 | 0 | 0 |
| 142 | 0.95 | 0 | −1 | 0 | 0.05 | 0 | 0 | 0 | 0 | 0 | 0 | 0 | 0 | 0 | 0 | 0 |
| 143 | 0.9 | 0 | −1 | 0 | 0.1 | 0 | 0 | 0 | 0 | 0 | 0 | 0 | 0 | 0 | 0 | 0 |
| 144 | 0.85 | 0 | −1 | 0 | 0.15 | 0 | 0 | 0 | 0 | 0 | 0 | 0 | 0 | 0 | 0 | 0 |
| 145 | 0.8 | 0 | −1 | 0 | 0.2 | 0 | 0 | 0 | 0 | 0 | 0 | 0 | 0 | 0 | 0 | 0 |
| 146 | 0.75 | 0 | −1 | 0 | 0.25 | 0 | 0 | 0 | 0 | 0 | 0 | 0 | 0 | 0 | 0 | 0 |
| 147 | 0.7 | 0 | −1 | 0 | 0.3 | 0 | 0 | 0 | 0 | 0 | 0 | 0 | 0 | 0 | 0 | 0 |
| 148 | 0.65 | 0 | −1 | 0 | 0.35 | 0 | 0 | 0 | 0 | 0 | 0 | 0 | 0 | 0 | 0 | 0 |
| 149 | 0.6 | 0 | −1 | 0 | 0.4 | 0 | 0 | 0 | 0 | 0 | 0 | 0 | 0 | 0 | 0 | 0 |
| 150 | 0.55 | 0 | −1 | 0 | 0.45 | 0 | 0 | 0 | 0 | 0 | 0 | 0 | 0 | 0 | 0 | 0 |
| 151 | 0.5 | 0 | −1 | 0 | 0.5 | 0 | 0 | 0 | 0 | 0 | 0 | 0 | 0 | 0 | 0 | 0 |

APPENDIX A-continued

Simplified Steering Table

| Stim# | \multicolumn{16}{c}{Electrode#} | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| 152 | 0.45 | 0 | −1 | 0 | 0.55 | 0 | 0 | 0 | 0 | 0 | 0 | 0 | 0 | 0 | 0 | 0 |
| 153 | 0.4 | 0 | −1 | 0 | 0.6 | 0 | 0 | 0 | 0 | 0 | 0 | 0 | 0 | 0 | 0 | 0 |
| 154 | 0.35 | 0 | −1 | 0 | 0.65 | 0 | 0 | 0 | 0 | 0 | 0 | 0 | 0 | 0 | 0 | 0 |
| 155 | 0.3 | 0 | −1 | 0 | 0.7 | 0 | 0 | 0 | 0 | 0 | 0 | 0 | 0 | 0 | 0 | 0 |
| 156 | 0.25 | 0 | −1 | 0 | 0.75 | 0 | 0 | 0 | 0 | 0 | 0 | 0 | 0 | 0 | 0 | 0 |
| 157 | 0.2 | 0 | −1 | 0 | 0.8 | 0 | 0 | 0 | 0 | 0 | 0 | 0 | 0 | 0 | 0 | 0 |
| 158 | 0.15 | 0 | −1 | 0 | 0.85 | 0 | 0 | 0 | 0 | 0 | 0 | 0 | 0 | 0 | 0 | 0 |
| 159 | 0.1 | 0 | −1 | 0 | 0.9 | 0 | 0 | 0 | 0 | 0 | 0 | 0 | 0 | 0 | 0 | 0 |
| 160 | 0.05 | 0 | −1 | 0 | 0.95 | 0 | 0 | 0 | 0 | 0 | 0 | 0 | 0 | 0 | 0 | 0 |
| 161 | 0 | 0 | −1 | 0 | 1 | 0 | 0 | 0 | 0 | 0 | 0 | 0 | 0 | 0 | 0 | 0 |
| 162 | 0 | 0 | −1 | 0 | 0.95 | 0.05 | 0 | 0 | 0 | 0 | 0 | 0 | 0 | 0 | 0 | 0 |
| 163 | 0 | 0 | −1 | 0 | 0.9 | 0.1 | 0 | 0 | 0 | 0 | 0 | 0 | 0 | 0 | 0 | 0 |
| 164 | 0 | 0 | −1 | 0 | 0.85 | 0.15 | 0 | 0 | 0 | 0 | 0 | 0 | 0 | 0 | 0 | 0 |
| 165 | 0 | −1 | 0 | 0 | 0.8 | 0.2 | 0 | 0 | 0 | 0 | 0 | 0 | 0 | 0 | 0 | 0 |
| 166 | 0 | −1 | 0 | 0 | 0.75 | 0.25 | 0 | 0 | 0 | 0 | 0 | 0 | 0 | 0 | 0 | 0 |
| 167 | 0 | −1 | 0 | 0 | 0.7 | 0.3 | 0 | 0 | 0 | 0 | 0 | 0 | 0 | 0 | 0 | 0 |
| 168 | 0 | −1 | 0 | 0 | 0.65 | 0.35 | 0 | 0 | 0 | 0 | 0 | 0 | 0 | 0 | 0 | 0 |
| 169 | 0 | −1 | 0 | 0 | 0.6 | 0.4 | 0 | 0 | 0 | 0 | 0 | 0 | 0 | 0 | 0 | 0 |
| 170 | 0 | −1 | 0 | 0 | 0.55 | 0.45 | 0 | 0 | 0 | 0 | 0 | 0 | 0 | 0 | 0 | 0 |
| 171 | 0 | −1 | 0 | 0 | 0.5 | 0.5 | 0 | 0 | 0 | 0 | 0 | 0 | 0 | 0 | 0 | 0 |
| 172 | 0 | −1 | 0 | 0 | 0.45 | 0.55 | 0 | 0 | 0 | 0 | 0 | 0 | 0 | 0 | 0 | 0 |
| 173 | 0 | −1 | 0 | 0 | 0.4 | 0.6 | 0 | 0 | 0 | 0 | 0 | 0 | 0 | 0 | 0 | 0 |
| 174 | 0 | −1 | 0 | 0 | 0.35 | 0.65 | 0 | 0 | 0 | 0 | 0 | 0 | 0 | 0 | 0 | 0 |
| 175 | 0 | −1 | 0 | 0 | 0.3 | 0.7 | 0 | 0 | 0 | 0 | 0 | 0 | 0 | 0 | 0 | 0 |
| 176 | 0 | −1 | 0 | 0 | 0.25 | 0.75 | 0 | 0 | 0 | 0 | 0 | 0 | 0 | 0 | 0 | 0 |
| 177 | 0 | −1 | 0 | 0 | 0.2 | 0.8 | 0 | 0 | 0 | 0 | 0 | 0 | 0 | 0 | 0 | 0 |
| 178 | 0 | −1 | 0 | 0 | 0.15 | 0.85 | 0 | 0 | 0 | 0 | 0 | 0 | 0 | 0 | 0 | 0 |
| 179 | 0 | −1 | 0 | 0 | 0.1 | 0.9 | 0 | 0 | 0 | 0 | 0 | 0 | 0 | 0 | 0 | 0 |
| 180 | 0 | −1 | 0 | 0 | 0.05 | 0.95 | 0 | 0 | 0 | 0 | 0 | 0 | 0 | 0 | 0 | 0 |
| 181 | 0 | −1 | 0 | 0 | 0 | 1 | 0 | 0 | 0 | 0 | 0 | 0 | 0 | 0 | 0 | 0 |
| 182 | 0.05 | 0 | −0.95 | 0 | −0.05 | 0.95 | 0 | 0 | 0 | 0 | 0 | 0 | 0 | 0 | 0 | 0 |
| 183 | 0.1 | 0 | −0.9 | 0 | −0.1 | 0.9 | 0 | 0 | 0 | 0 | 0 | 0 | 0 | 0 | 0 | 0 |
| 184 | 0.15 | 0 | −0.85 | 0 | −0.15 | 0.85 | 0 | 0 | 0 | 0 | 0 | 0 | 0 | 0 | 0 | 0 |
| 185 | 0.2 | 0 | −0.8 | 0 | −0.2 | 0.8 | 0 | 0 | 0 | 0 | 0 | 0 | 0 | 0 | 0 | 0 |
| 186 | 0.25 | 0 | −0.75 | 0 | −0.25 | 0.75 | 0 | 0 | 0 | 0 | 0 | 0 | 0 | 0 | 0 | 0 |
| 187 | 0.3 | 0 | −0.7 | 0 | −0.3 | 0.7 | 0 | 0 | 0 | 0 | 0 | 0 | 0 | 0 | 0 | 0 |
| 188 | 0.35 | 0 | −0.65 | 0 | −0.35 | 0.65 | 0 | 0 | 0 | 0 | 0 | 0 | 0 | 0 | 0 | 0 |
| 189 | 0.4 | 0 | −0.6 | 0 | −0.4 | 0.6 | 0 | 0 | 0 | 0 | 0 | 0 | 0 | 0 | 0 | 0 |
| 190 | 0.45 | 0 | −0.55 | 0 | −0.45 | 0.55 | 0 | 0 | 0 | 0 | 0 | 0 | 0 | 0 | 0 | 0 |
| 191 | 0.5 | 0 | −0.5 | 0 | −0.5 | 0.5 | 0 | 0 | 0 | 0 | 0 | 0 | 0 | 0 | 0 | 0 |
| 192 | 0.55 | 0 | −0.45 | 0 | −0.55 | 0.45 | 0 | 0 | 0 | 0 | 0 | 0 | 0 | 0 | 0 | 0 |
| 193 | 0.6 | 0 | −0.4 | 0 | −0.6 | 0.4 | 0 | 0 | 0 | 0 | 0 | 0 | 0 | 0 | 0 | 0 |
| 194 | 0.65 | 0 | −0.35 | 0 | −0.65 | 0.35 | 0 | 0 | 0 | 0 | 0 | 0 | 0 | 0 | 0 | 0 |
| 195 | 0.7 | 0 | −0.3 | 0 | −0.7 | 0.3 | 0 | 0 | 0 | 0 | 0 | 0 | 0 | 0 | 0 | 0 |
| 196 | 0.75 | 0 | −0.25 | 0 | −0.75 | 0.25 | 0 | 0 | 0 | 0 | 0 | 0 | 0 | 0 | 0 | 0 |
| 197 | 0.8 | 0 | −0.2 | 0 | −0.8 | 0.2 | 0 | 0 | 0 | 0 | 0 | 0 | 0 | 0 | 0 | 0 |
| 198 | 0.85 | 0 | −0.15 | 0 | −0.85 | 0.15 | 0 | 0 | 0 | 0 | 0 | 0 | 0 | 0 | 0 | 0 |
| 199 | 0.9 | 0 | −0.1 | 0 | −0.9 | 0.1 | 0 | 0 | 0 | 0 | 0 | 0 | 0 | 0 | 0 | 0 |
| 200 | 0.95 | 0 | −0.05 | 0 | −0.95 | 0.05 | 0 | 0 | 0 | 0 | 0 | 0 | 0 | 0 | 0 | 0 |
| 201 | 1 | 0 | 0 | 0 | −1 | 0 | 0 | 0 | 0 | 0 | 0 | 0 | 0 | 0 | 0 | 0 |
| 202 | 0.95 | 0.05 | 0 | 0 | −1 | 0 | 0 | 0 | 0 | 0 | 0 | 0 | 0 | 0 | 0 | 0 |
| 203 | 0.9 | 0.1 | 0 | 0 | −1 | 0 | 0 | 0 | 0 | 0 | 0 | 0 | 0 | 0 | 0 | 0 |
| 204 | 0.85 | 0.15 | 0 | 0 | −1 | 0 | 0 | 0 | 0 | 0 | 0 | 0 | 0 | 0 | 0 | 0 |
| 205 | 0.8 | 0.2 | 0 | 0 | −1 | 0 | 0 | 0 | 0 | 0 | 0 | 0 | 0 | 0 | 0 | 0 |
| 206 | 0.75 | 0.25 | 0 | −1 | 0 | 0 | 0 | 0 | 0 | 0 | 0 | 0 | 0 | 0 | 0 | 0 |
| 207 | 0.7 | 0.3 | 0 | −1 | 0 | 0 | 0 | 0 | 0 | 0 | 0 | 0 | 0 | 0 | 0 | 0 |
| 208 | 0.65 | 0.35 | 0 | −1 | 0 | 0 | 0 | 0 | 0 | 0 | 0 | 0 | 0 | 0 | 0 | 0 |
| 209 | 0.6 | 0.4 | 0 | −1 | 0 | 0 | 0 | 0 | 0 | 0 | 0 | 0 | 0 | 0 | 0 | 0 |
| 210 | 0.55 | 0.45 | 0 | −1 | 0 | 0 | 0 | 0 | 0 | 0 | 0 | 0 | 0 | 0 | 0 | 0 |
| 211 | 0.5 | 0.5 | 0 | −1 | 0 | 0 | 0 | 0 | 0 | 0 | 0 | 0 | 0 | 0 | 0 | 0 |
| 212 | 0.45 | 0.55 | 0 | −1 | 0 | 0 | 0 | 0 | 0 | 0 | 0 | 0 | 0 | 0 | 0 | 0 |
| 213 | 0.4 | 0.6 | 0 | −1 | 0 | 0 | 0 | 0 | 0 | 0 | 0 | 0 | 0 | 0 | 0 | 0 |
| 214 | 0.35 | 0.65 | 0 | −1 | 0 | 0 | 0 | 0 | 0 | 0 | 0 | 0 | 0 | 0 | 0 | 0 |
| 215 | 0.3 | 0.7 | 0 | −1 | 0 | 0 | 0 | 0 | 0 | 0 | 0 | 0 | 0 | 0 | 0 | 0 |
| 216 | 0.25 | 0.75 | 0 | −1 | 0 | 0 | 0 | 0 | 0 | 0 | 0 | 0 | 0 | 0 | 0 | 0 |
| 217 | 0.2 | 0.8 | 0 | −1 | 0 | 0 | 0 | 0 | 0 | 0 | 0 | 0 | 0 | 0 | 0 | 0 |
| 218 | 0.15 | 0.85 | 0 | −1 | 0 | 0 | 0 | 0 | 0 | 0 | 0 | 0 | 0 | 0 | 0 | 0 |
| 219 | 0.1 | 0.9 | 0 | −1 | 0 | 0 | 0 | 0 | 0 | 0 | 0 | 0 | 0 | 0 | 0 | 0 |
| 220 | 0.05 | 0.95 | 0 | −1 | 0 | 0 | 0 | 0 | 0 | 0 | 0 | 0 | 0 | 0 | 0 | 0 |
| 221 | 0 | 1 | 0 | −1 | 0 | 0 | 0 | 0 | 0 | 0 | 0 | 0 | 0 | 0 | 0 | 0 |
| 222 | 0 | 0.95 | 0 | −1 | 0 | 0.05 | 0 | 0 | 0 | 0 | 0 | 0 | 0 | 0 | 0 | 0 |
| 223 | 0 | 0.9 | 0 | −1 | 0 | 0.1 | 0 | 0 | 0 | 0 | 0 | 0 | 0 | 0 | 0 | 0 |
| 224 | 0 | 0.85 | 0 | −1 | 0.15 | 0 | 0 | 0 | 0 | 0 | 0 | 0 | 0 | 0 | 0 | 0 |
| 225 | 0 | 0.8 | 0 | −1 | 0 | 0.2 | 0 | 0 | 0 | 0 | 0 | 0 | 0 | 0 | 0 | 0 |

APPENDIX A-continued

Simplified Steering Table

| Stim# | Electrode# | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| 226 | 0 | 0.75 | 0 | −1 | 0 | 0.25 | 0 | 0 | 0 | 0 | 0 | 0 | 0 | 0 | 0 | 0 |
| 227 | 0 | 0.7 | 0 | −1 | 0 | 0.3 | 0 | 0 | 0 | 0 | 0 | 0 | 0 | 0 | 0 | 0 |
| 228 | 0 | 0.65 | 0 | −1 | 0 | 0.35 | 0 | 0 | 0 | 0 | 0 | 0 | 0 | 0 | 0 | 0 |
| 229 | 0 | 0.6 | 0 | −1 | 0 | 0.4 | 0 | 0 | 0 | 0 | 0 | 0 | 0 | 0 | 0 | 0 |
| 230 | 0 | 0.55 | 0 | −1 | 0 | 0.45 | 0 | 0 | 0 | 0 | 0 | 0 | 0 | 0 | 0 | 0 |
| 231 | 0 | 0.5 | 0 | −1 | 0 | 0.5 | 0 | 0 | 0 | 0 | 0 | 0 | 0 | 0 | 0 | 0 |
| 232 | 0 | 0.45 | 0 | −1 | 0 | 0.55 | 0 | 0 | 0 | 0 | 0 | 0 | 0 | 0 | 0 | 0 |
| 233 | 0 | 0.4 | 0 | −1 | 0 | 0.6 | 0 | 0 | 0 | 0 | 0 | 0 | 0 | 0 | 0 | 0 |
| 234 | 0 | 0.35 | 0 | −1 | 0 | 0.65 | 0 | 0 | 0 | 0 | 0 | 0 | 0 | 0 | 0 | 0 |
| 235 | 0 | 0.3 | 0 | −1 | 0 | 0.7 | 0 | 0 | 0 | 0 | 0 | 0 | 0 | 0 | 0 | 0 |
| 236 | 0 | 0.25 | 0 | −1 | 0 | 0.75 | 0 | 0 | 0 | 0 | 0 | 0 | 0 | 0 | 0 | 0 |
| 237 | 0 | 0.2 | 0 | −1 | 0 | 0.8 | 0 | 0 | 0 | 0 | 0 | 0 | 0 | 0 | 0 | 0 |
| 238 | 0 | 0.15 | 0 | −1 | 0 | 0.85 | 0 | 0 | 0 | 0 | 0 | 0 | 0 | 0 | 0 | 0 |
| 239 | 0 | 0.1 | 0 | −1 | 0 | 0.9 | 0 | 0 | 0 | 0 | 0 | 0 | 0 | 0 | 0 | 0 |
| 240 | 0 | 0.05 | 0 | −1 | 0 | 0.95 | 0 | 0 | 0 | 0 | 0 | 0 | 0 | 0 | 0 | 0 |
| 241 | 0 | 0 | 0 | −1 | 0 | 1 | 0 | 0 | 0 | 0 | 0 | 0 | 0 | 0 | 0 | 0 |
| 242 | 0 | 0 | 0 | −1 | 0 | 0.95 | 0.05 | 0 | 0 | 0 | 0 | 0 | 0 | 0 | 0 | 0 |
| 243 | 0 | 0 | 0 | −1 | 0 | 0.9 | 0.1 | 0 | 0 | 0 | 0 | 0 | 0 | 0 | 0 | 0 |
| 244 | 0 | 0 | 0 | −1 | 0 | 0.85 | 0.15 | 0 | 0 | 0 | 0 | 0 | 0 | 0 | 0 | 0 |
| 245 | 0 | 0 | 0 | −1 | 0 | 0.8 | 0.2 | 0 | 0 | 0 | 0 | 0 | 0 | 0 | 0 | 0 |
| 246 | 0 | 0 | 0 | −1 | 0 | 0.75 | 0.25 | 0 | 0 | 0 | 0 | 0 | 0 | 0 | 0 | 0 |
| 247 | 0 | 0 | 0 | −1 | 0 | 0.7 | 0.3 | 0 | 0 | 0 | 0 | 0 | 0 | 0 | 0 | 0 |
| 248 | 0 | 0 | 0 | −1 | 0 | 0.65 | 0.35 | 0 | 0 | 0 | 0 | 0 | 0 | 0 | 0 | 0 |
| 249 | 0 | 0 | 0 | −1 | 0 | 0.6 | 0.4 | 0 | 0 | 0 | 0 | 0 | 0 | 0 | 0 | 0 |
| 250 | 0 | 0 | 0 | −1 | 0 | 0.55 | 0.45 | 0 | 0 | 0 | 0 | 0 | 0 | 0 | 0 | 0 |
| 251 | 0 | 0 | 0 | −1 | 0 | 0.5 | 0.5 | 0 | 0 | 0 | 0 | 0 | 0 | 0 | 0 | 0 |
| 252 | 0 | 0 | 0 | −1 | 0 | 0.45 | 0.55 | 0 | 0 | 0 | 0 | 0 | 0 | 0 | 0 | 0 |
| 253 | 0 | 0 | 0 | −1 | 0 | 0.4 | 0.6 | 0 | 0 | 0 | 0 | 0 | 0 | 0 | 0 | 0 |
| 254 | 0 | 0 | 0 | −1 | 0 | 0.35 | 0.65 | 0 | 0 | 0 | 0 | 0 | 0 | 0 | 0 | 0 |
| 256 | 0 | 0 | 0 | −1 | 0 | 0.3 | 0.7 | 0 | 0 | 0 | 0 | 0 | 0 | 0 | 0 | 0 |
| 257 | 0 | 0 | 0 | −1 | 0 | 0.25 | 0.75 | 0 | 0 | 0 | 0 | 0 | 0 | 0 | 0 | 0 |
| 258 | 0 | 0 | 0 | −1 | 0 | 0.2 | 0.8 | 0 | 0 | 0 | 0 | 0 | 0 | 0 | 0 | 0 |
| 259 | 0 | 0 | 0 | −1 | 0 | 0.15 | 0.85 | 0 | 0 | 0 | 0 | 0 | 0 | 0 | 0 | 0 |
| 260 | 0 | 0 | 0 | −1 | 0 | 0.1 | 0.9 | 0 | 0 | 0 | 0 | 0 | 0 | 0 | 0 | 0 |
| 261 | 0 | 0 | 0 | −1 | 0 | 0.05 | 0.95 | 0 | 0 | 0 | 0 | 0 | 0 | 0 | 0 | 0 |
| 262 | 0 | 0.05 | 0 | −0.95 | −0.05 | 0 | 1 | 0 | 0 | 0 | 0 | 0 | 0 | 0 | 0 | 0 |
| 263 | 0 | 0.1 | 0 | −0.9 | −0.1 | 0 | 0.95 | 0 | 0 | 0 | 0 | 0 | 0 | 0 | 0 | 0 |
| 264 | 0 | 0.15 | 0 | −0.85 | −0.15 | 0 | 0.9 | 0 | 0 | 0 | 0 | 0 | 0 | 0 | 0 | 0 |
| 265 | 0 | 0.2 | 0 | −0.8 | −0.2 | 0 | 0.85 | 0 | 0 | 0 | 0 | 0 | 0 | 0 | 0 | 0 |
| 266 | 0 | 0.25 | 0 | −0.75 | −0.25 | 0 | 0.8 | 0 | 0 | 0 | 0 | 0 | 0 | 0 | 0 | 0 |
| 267 | 0 | 0.3 | 0 | −0.7 | −0.3 | 0 | 0.75 | 0 | 0 | 0 | 0 | 0 | 0 | 0 | 0 | 0 |
| 268 | 0 | 0.35 | 0 | −0.65 | −0.35 | 0 | 0.7 | 0 | 0 | 0 | 0 | 0 | 0 | 0 | 0 | 0 |
| 269 | 0 | 0.4 | 0 | −0.6 | −0.4 | 0 | 0.65 | 0 | 0 | 0 | 0 | 0 | 0 | 0 | 0 | 0 |
| 270 | 0 | 0.45 | 0 | −0.55 | −0.45 | 0 | 0.6 | 0 | 0 | 0 | 0 | 0 | 0 | 0 | 0 | 0 |
| 271 | 0 | 0.5 | 0 | −0.5 | −0.5 | 0 | 0.55 | 0 | 0 | 0 | 0 | 0 | 0 | 0 | 0 | 0 |
| 272 | 0 | 0.55 | 0 | −0.45 | −0.55 | 0 | 0.5 | 0 | 0 | 0 | 0 | 0 | 0 | 0 | 0 | 0 |
| 273 | 0 | 0.6 | 0 | −0.4 | −0.6 | 0 | 0.45 | 0 | 0 | 0 | 0 | 0 | 0 | 0 | 0 | 0 |
| 274 | 0 | 0.65 | 0 | −0.35 | −0.65 | 0 | 0.4 | 0 | 0 | 0 | 0 | 0 | 0 | 0 | 0 | 0 |
| 275 | 0 | 0.7 | 0 | −0.3 | −0.7 | 0 | 0.35 | 0 | 0 | 0 | 0 | 0 | 0 | 0 | 0 | 0 |
| 276 | 0 | 0.75 | 0 | −0.25 | −0.75 | 0 | 0.3 | 0 | 0 | 0 | 0 | 0 | 0 | 0 | 0 | 0 |
| 277 | 0 | 0.8 | 0 | −0.2 | −0.8 | 0 | 0.25 | 0 | 0 | 0 | 0 | 0 | 0 | 0 | 0 | 0 |
| 278 | 0 | 0.85 | 0 | −0.15 | −0.85 | 0 | 0.2 | 0 | 0 | 0 | 0 | 0 | 0 | 0 | 0 | 0 |
| 279 | 0 | 0.9 | 0 | −0.1 | −0.9 | 0 | 0.15 | 0 | 0 | 0 | 0 | 0 | 0 | 0 | 0 | 0 |
| 280 | 0 | 0.95 | 0 | −0.05 | −0.95 | 0 | 0.1 | 0 | 0 | 0 | 0 | 0 | 0 | 0 | 0 | 0 |
| 281 | 0 | 1 | 0 | 0 | −1 | 0 | 0.05 | 0 | 0 | 0 | 0 | 0 | 0 | 0 | 0 | 0 |
| 282 | 0 | 0.95 | 0.05 | 0 | −1 | 0 | 0 | 0 | 0 | 0 | 0 | 0 | 0 | 0 | 0 | 0 |
| 283 | 0 | 0.9 | 0.1 | 0 | −1 | 0 | 0 | 0 | 0 | 0 | 0 | 0 | 0 | 0 | 0 | 0 |
| 284 | 0 | 0.85 | 0.15 | 0 | −1 | 0 | 0 | 0 | 0 | 0 | 0 | 0 | 0 | 0 | 0 | 0 |
| 285 | 0 | 0.8 | 0.2 | 0 | −1 | 0 | 0 | 0 | 0 | 0 | 0 | 0 | 0 | 0 | 0 | 0 |
| 286 | 0 | 0.75 | 0.25 | 0 | −1 | 0 | 0 | 0 | 0 | 0 | 0 | 0 | 0 | 0 | 0 | 0 |
| 287 | 0 | 0.7 | 0.3 | 0 | −1 | 0 | 0 | 0 | 0 | 0 | 0 | 0 | 0 | 0 | 0 | 0 |
| 288 | 0 | 0.65 | 0.35 | 0 | −1 | 0 | 0 | 0 | 0 | 0 | 0 | 0 | 0 | 0 | 0 | 0 |
| 289 | 0 | 0.6 | 0.4 | 0 | −1 | 0 | 0 | 0 | 0 | 0 | 0 | 0 | 0 | 0 | 0 | 0 |
| 290 | 0 | 0.55 | 0.45 | 0 | −1 | 0 | 0 | 0 | 0 | 0 | 0 | 0 | 0 | 0 | 0 | 0 |
| 291 | 0 | 0.5 | 0.5 | 0 | −1 | 0 | 0 | 0 | 0 | 0 | 0 | 0 | 0 | 0 | 0 | 0 |
| 292 | 0 | 0.45 | 0.55 | 0 | −1 | 0 | 0 | 0 | 0 | 0 | 0 | 0 | 0 | 0 | 0 | 0 |
| 293 | 0 | 0.4 | 0.6 | 0 | −1 | 0 | 0 | 0 | 0 | 0 | 0 | 0 | 0 | 0 | 0 | 0 |
| 294 | 0 | 0.35 | 0.65 | 0 | −1 | 0 | 0 | 0 | 0 | 0 | 0 | 0 | 0 | 0 | 0 | 0 |
| 295 | 0 | 0.3 | 0.7 | 0 | −1 | 0 | 0 | 0 | 0 | 0 | 0 | 0 | 0 | 0 | 0 | 0 |
| 296 | 0 | 0.25 | 0.75 | 0 | −1 | 0 | 0 | 0 | 0 | 0 | 0 | 0 | 0 | 0 | 0 | 0 |
| 297 | 0 | 0.2 | 0.8 | 0 | −1 | 0 | 0 | 0 | 0 | 0 | 0 | 0 | 0 | 0 | 0 | 0 |
| 298 | 0 | 0.15 | 0.85 | 0 | −1 | 0 | 0 | 0 | 0 | 0 | 0 | 0 | 0 | 0 | 0 | 0 |
| 299 | 0 | 0.1 | 0.9 | 0 | −1 | 0 | 0 | 0 | 0 | 0 | 0 | 0 | 0 | 0 | 0 | 0 |
| 300 | 0 | 0.05 | 0.95 | 0 | −1 | 0 | 0 | 0 | 0 | 0 | 0 | 0 | 0 | 0 | 0 | 0 |

APPENDIX A-continued

Simplified Steering Table

| Stim# | \multicolumn{16}{c}{Electrode#} | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| 301 | 0 | 0 | 1 | 0 | −1 | 0 | 0 | 0 | 0 | 0 | 0 | 0 | 0 | 0 | 0 | 0 |
| 302 | 0 | 0 | 0.95 | 0 | −1 | 0 | 0.05 | 0 | 0 | 0 | 0 | 0 | 0 | 0 | 0 | 0 |
| 303 | 0 | 0 | 0.9 | 0 | −1 | 0 | 0.1 | 0 | 0 | 0 | 0 | 0 | 0 | 0 | 0 | 0 |
| 304 | 0 | 0 | 0.85 | 0 | −1 | 0 | 0.15 | 0 | 0 | 0 | 0 | 0 | 0 | 0 | 0 | 0 |
| 305 | 0 | 0 | 0.8 | 0 | −1 | 0 | 0.2 | 0 | 0 | 0 | 0 | 0 | 0 | 0 | 0 | 0 |
| 306 | 0 | 0 | 0.75 | 0 | −1 | 0 | 0.25 | 0 | 0 | 0 | 0 | 0 | 0 | 0 | 0 | 0 |
| 307 | 0 | 0 | 0.7 | 0 | −1 | 0 | 0.3 | 0 | 0 | 0 | 0 | 0 | 0 | 0 | 0 | 0 |
| 308 | 0 | 0 | 0.65 | 0 | −1 | 0 | 0.35 | 0 | 0 | 0 | 0 | 0 | 0 | 0 | 0 | 0 |
| 309 | 0 | 0 | 0.6 | 0 | −1 | 0 | 0.4 | 0 | 0 | 0 | 0 | 0 | 0 | 0 | 0 | 0 |
| 310 | 0 | 0 | 0.55 | 0 | −1 | 0 | 0.45 | 0 | 0 | 0 | 0 | 0 | 0 | 0 | 0 | 0 |
| 311 | 0 | 0 | 0.5 | 0 | −1 | 0 | 0.5 | 0 | 0 | 0 | 0 | 0 | 0 | 0 | 0 | 0 |
| 312 | 0 | 0 | 0.45 | 0 | −1 | 0 | 0.55 | 0 | 0 | 0 | 0 | 0 | 0 | 0 | 0 | 0 |
| 313 | 0 | 0 | 0.4 | 0 | −1 | 0 | 0.6 | 0 | 0 | 0 | 0 | 0 | 0 | 0 | 0 | 0 |
| 314 | 0 | 0 | 0.35 | 0 | −1 | 0 | 0.65 | 0 | 0 | 0 | 0 | 0 | 0 | 0 | 0 | 0 |
| 315 | 0 | 0 | 0.3 | 0 | −1 | 0 | 0.7 | 0 | 0 | 0 | 0 | 0 | 0 | 0 | 0 | 0 |
| 316 | 0 | 0 | 0.25 | 0 | −1 | 0 | 0.75 | 0 | 0 | 0 | 0 | 0 | 0 | 0 | 0 | 0 |
| 317 | 0 | 0 | 0.2 | 0 | −1 | 0 | 0.8 | 0 | 0 | 0 | 0 | 0 | 0 | 0 | 0 | 0 |
| 318 | 0 | 0 | 0.15 | 0 | −1 | 0 | 0.85 | 0 | 0 | 0 | 0 | 0 | 0 | 0 | 0 | 0 |
| 319 | 0 | 0 | 0.1 | 0 | −1 | 0 | 0.9 | 0 | 0 | 0 | 0 | 0 | 0 | 0 | 0 | 0 |
| 320 | 0 | 0 | 0.05 | 0 | −1 | 0 | 0.95 | 0 | 0 | 0 | 0 | 0 | 0 | 0 | 0 | 0 |
| 321 | 0 | 0 | 0 | 0 | −1 | 0 | 1 | 0 | 0 | 0 | 0 | 0 | 0 | 0 | 0 | 0 |
| 322 | 0 | 0 | 0 | 0 | −1 | 0 | 0.95 | 0.05 | 0 | 0 | 0 | 0 | 0 | 0 | 0 | 0 |
| 323 | 0 | 0 | 0 | 0 | −1 | 0 | 0.9 | 0.1 | 0 | 0 | 0 | 0 | 0 | 0 | 0 | 0 |
| 324 | 0 | 0 | 0 | 0 | −1 | 0 | 0.85 | 0.15 | 0 | 0 | 0 | 0 | 0 | 0 | 0 | 0 |
| 325 | 0 | 0 | 0 | 0 | −1 | 0 | 0.8 | 0.2 | 0 | 0 | 0 | 0 | 0 | 0 | 0 | 0 |
| 326 | 0 | 0 | 0 | 0 | −1 | 0 | 0.75 | 0.25 | 0 | 0 | 0 | 0 | 0 | 0 | 0 | 0 |
| 327 | 0 | 0 | 0 | 0 | −1 | 0 | 0.7 | 0.3 | 0 | 0 | 0 | 0 | 0 | 0 | 0 | 0 |
| 328 | 0 | 0 | 0 | 0 | −1 | 0 | 0.65 | 0.35 | 0 | 0 | 0 | 0 | 0 | 0 | 0 | 0 |
| 329 | 0 | 0 | 0 | 0 | −1 | 0 | 0.6 | 0.4 | 0 | 0 | 0 | 0 | 0 | 0 | 0 | 0 |
| 330 | 0 | 0 | 0 | 0 | −1 | 0 | 0.55 | 0.45 | 0 | 0 | 0 | 0 | 0 | 0 | 0 | 0 |
| 331 | 0 | 0 | 0 | 0 | −1 | 0 | 0.5 | 0.5 | 0 | 0 | 0 | 0 | 0 | 0 | 0 | 0 |
| 332 | 0 | 0 | 0 | 0 | −1 | 0 | 0.45 | 0.55 | 0 | 0 | 0 | 0 | 0 | 0 | 0 | 0 |
| 333 | 0 | 0 | 0 | 0 | −1 | 0 | 0.4 | 0.6 | 0 | 0 | 0 | 0 | 0 | 0 | 0 | 0 |
| 334 | 0 | 0 | 0 | 0 | −1 | 0 | 0.35 | 0.65 | 0 | 0 | 0 | 0 | 0 | 0 | 0 | 0 |
| 335 | 0 | 0 | 0 | 0 | −1 | 0 | 0.3 | 0.7 | 0 | 0 | 0 | 0 | 0 | 0 | 0 | 0 |
| 336 | 0 | 0 | 0 | 0 | −1 | 0 | 0.25 | 0.75 | 0 | 0 | 0 | 0 | 0 | 0 | 0 | 0 |
| 337 | 0 | 0 | 0 | 0 | −1 | 0 | 0.2 | 0.8 | 0 | 0 | 0 | 0 | 0 | 0 | 0 | 0 |
| 338 | 0 | 0 | 0 | 0 | −1 | 0 | 0.15 | 0.85 | 0 | 0 | 0 | 0 | 0 | 0 | 0 | 0 |
| 339 | 0 | 0 | 0 | 0 | −1 | 0 | 0.1 | 0.9 | 0 | 0 | 0 | 0 | 0 | 0 | 0 | 0 |
| 340 | 0 | 0 | 0 | 0 | −1 | 0 | 0.05 | 0.95 | 0 | 0 | 0 | 0 | 0 | 0 | 0 | 0 |
| 341 | 0 | 0 | 0 | 0 | −1 | 0 | 0 | 1 | 0 | 0 | 0 | 0 | 0 | 0 | 0 | 0 |
| 342 | 0 | 0 | 0.05 | 0 | −0.95 | −0.05 | 0 | 0.95 | 0 | 0 | 0 | 0 | 0 | 0 | 0 | 0 |
| 343 | 0 | 0 | 0.1 | 0 | −0.9 | −0.1 | 0 | 0.9 | 0 | 0 | 0 | 0 | 0 | 0 | 0 | 0 |
| 344 | 0 | 0 | 0.15 | 0 | −0.85 | −0.15 | 0 | 0.85 | 0 | 0 | 0 | 0 | 0 | 0 | 0 | 0 |
| 345 | 0 | 0 | 0.2 | 0 | −0.8 | −0.2 | 0 | 0.8 | 0 | 0 | 0 | 0 | 0 | 0 | 0 | 0 |
| 346 | 0 | 0 | 0.25 | 0 | −0.75 | −0.25 | 0 | 0.75 | 0 | 0 | 0 | 0 | 0 | 0 | 0 | 0 |
| 347 | 0 | 0 | 0.3 | 0 | −0.7 | −0.3 | 0 | 0.7 | 0 | 0 | 0 | 0 | 0 | 0 | 0 | 0 |
| 348 | 0 | 0 | 0.35 | 0 | −0.65 | −0.35 | 0 | 0.65 | 0 | 0 | 0 | 0 | 0 | 0 | 0 | 0 |
| 349 | 0 | 0 | 0.4 | 0 | −0.6 | −0.4 | 0 | 0.6 | 0 | 0 | 0 | 0 | 0 | 0 | 0 | 0 |
| 350 | 0 | 0 | 0.45 | 0 | −0.55 | −0.45 | 0 | 0.55 | 0 | 0 | 0 | 0 | 0 | 0 | 0 | 0 |
| 351 | 0 | 0 | 0.5 | 0 | −0.5 | −0.5 | 0 | 0.5 | 0 | 0 | 0 | 0 | 0 | 0 | 0 | 0 |
| 352 | 0 | 0 | 0.55 | 0 | −0.45 | −0.55 | 0 | 0.45 | 0 | 0 | 0 | 0 | 0 | 0 | 0 | 0 |
| 353 | 0 | 0 | 0.6 | 0 | −0.4 | −0.6 | 0 | 0.4 | 0 | 0 | 0 | 0 | 0 | 0 | 0 | 0 |
| 354 | 0 | 0 | 0.65 | 0 | −0.35 | −0.65 | 0 | 0.35 | 0 | 0 | 0 | 0 | 0 | 0 | 0 | 0 |
| 355 | 0 | 0 | 0.7 | 0 | −0.3 | −0.7 | 0 | 0.3 | 0 | 0 | 0 | 0 | 0 | 0 | 0 | 0 |
| 356 | 0 | 0 | 0.75 | 0 | −0.25 | −0.75 | 0 | 0.25 | 0 | 0 | 0 | 0 | 0 | 0 | 0 | 0 |
| 357 | 0 | 0 | 0.8 | 0 | −0.2 | −0.8 | 0 | 0.2 | 0 | 0 | 0 | 0 | 0 | 0 | 0 | 0 |
| 358 | 0 | 0 | 0.85 | 0 | −0.15 | −0.85 | 0 | 0.15 | 0 | 0 | 0 | 0 | 0 | 0 | 0 | 0 |
| 359 | 0 | 0 | 0.9 | 0 | −0.1 | −0.9 | 0 | 0.1 | 0 | 0 | 0 | 0 | 0 | 0 | 0 | 0 |
| 360 | 0 | 0 | 0.95 | 0 | −0.05 | −0.95 | 0 | 0.05 | 0 | 0 | 0 | 0 | 0 | 0 | 0 | 0 |
| 361 | 0 | 0 | 1 | 0 | 0 | −1 | 0 | 0 | 0 | 0 | 0 | 0 | 0 | 0 | 0 | 0 |
| 362 | 0 | 0 | 0.95 | 0.05 | 0 | −1 | 0 | 0 | 0 | 0 | 0 | 0 | 0 | 0 | 0 | 0 |
| 363 | 0 | 0 | 0.9 | 0.1 | 0 | −1 | 0 | 0 | 0 | 0 | 0 | 0 | 0 | 0 | 0 | 0 |
| 364 | 0 | 0 | 0.85 | 0.15 | 0 | −1 | 0 | 0 | 0 | 0 | 0 | 0 | 0 | 0 | 0 | 0 |
| 365 | 0 | 0 | 0.8 | 0.2 | 0 | −1 | 0 | 0 | 0 | 0 | 0 | 0 | 0 | 0 | 0 | 0 |
| 366 | 0 | 0 | 0.75 | 0.25 | 0 | −1 | 0 | 0 | 0 | 0 | 0 | 0 | 0 | 0 | 0 | 0 |
| 367 | 0 | 0 | 0.7 | 0.3 | 0 | −1 | 0 | 0 | 0 | 0 | 0 | 0 | 0 | 0 | 0 | 0 |
| 368 | 0 | 0 | 0.65 | 0.35 | 0 | −1 | 0 | 0 | 0 | 0 | 0 | 0 | 0 | 0 | 0 | 0 |
| 369 | 0 | 0 | 0.6 | 0.4 | 0 | −1 | 0 | 0 | 0 | 0 | 0 | 0 | 0 | 0 | 0 | 0 |
| 370 | 0 | 0 | 0.55 | 0.45 | 0 | −1 | 0 | 0 | 0 | 0 | 0 | 0 | 0 | 0 | 0 | 0 |
| 371 | 0 | 0 | 0.5 | 0.5 | 0 | −1 | 0 | 0 | 0 | 0 | 0 | 0 | 0 | 0 | 0 | 0 |
| 372 | 0 | 0 | 0.45 | 0.55 | 0 | −1 | 0 | 0 | 0 | 0 | 0 | 0 | 0 | 0 | 0 | 0 |
| 373 | 0 | 0 | 0.4 | 0.6 | 0 | −1 | 0 | 0 | 0 | 0 | 0 | 0 | 0 | 0 | 0 | 0 |
| 374 | 0 | 0 | 0.35 | 0.65 | 0 | −1 | 0 | 0 | 0 | 0 | 0 | 0 | 0 | 0 | 0 | 0 |

APPENDIX A-continued

Simplified Steering Table

| Stim# | Electrode# | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| 375 | 0 | 0 | 0.3 | 0.7 | 0 | −1 | 0 | 0 | 0 | 0 | 0 | 0 | 0 | 0 | 0 | 0 |
| 376 | 0 | 0 | 0.25 | 0.75 | 0 | −1 | 0 | 0 | 0 | 0 | 0 | 0 | 0 | 0 | 0 | 0 |
| 377 | 0 | 0 | 0.2 | 0.8 | 0 | −1 | 0 | 0 | 0 | 0 | 0 | 0 | 0 | 0 | 0 | 0 |
| 378 | 0 | 0 | 0.15 | 0.85 | 0 | −1 | 0 | 0 | 0 | 0 | 0 | 0 | 0 | 0 | 0 | 0 |
| 379 | 0 | 0 | 0.1 | 0.9 | 0 | −1 | 0 | 0 | 0 | 0 | 0 | 0 | 0 | 0 | 0 | 0 |
| 380 | 0 | 0 | 0.05 | 0.95 | 0 | −1 | 0 | 0 | 0 | 0 | 0 | 0 | 0 | 0 | 0 | 0 |
| 381 | 0 | 0 | 0 | 1 | 0 | −1 | 0 | 0 | 0 | 0 | 0 | 0 | 0 | 0 | 0 | 0 |
| 382 | 0 | 0 | 0 | 0.95 | 0 | −1 | 0 | 0.05 | 0 | 0 | 0 | 0 | 0 | 0 | 0 | 0 |
| 383 | 0 | 0 | 0 | 0.9 | 0 | −1 | 0 | 0.1 | 0 | 0 | 0 | 0 | 0 | 0 | 0 | 0 |
| 384 | 0 | 0 | 0 | 0.85 | 0 | −1 | 0 | 0.15 | 0 | 0 | 0 | 0 | 0 | 0 | 0 | 0 |
| 385 | 0 | 0 | 0 | 0.8 | 0 | −1 | 0 | 0.2 | 0 | 0 | 0 | 0 | 0 | 0 | 0 | 0 |
| 386 | 0 | 0 | 0 | 0.75 | 0 | −1 | 0 | 0.25 | 0 | 0 | 0 | 0 | 0 | 0 | 0 | 0 |
| 387 | 0 | 0 | 0 | 0.7 | 0 | −1 | 0 | 0.3 | 0 | 0 | 0 | 0 | 0 | 0 | 0 | 0 |
| 388 | 0 | 0 | 0 | 0.65 | 0 | −1 | 0 | 0.35 | 0 | 0 | 0 | 0 | 0 | 0 | 0 | 0 |
| 389 | 0 | 0 | 0 | 0.6 | 0 | −1 | 0 | 0.4 | 0 | 0 | 0 | 0 | 0 | 0 | 0 | 0 |
| 390 | 0 | 0 | 0 | 0.55 | 0 | −1 | 0 | 0.45 | 0 | 0 | 0 | 0 | 0 | 0 | 0 | 0 |
| 391 | 0 | 0 | 0 | 0.5 | 0 | −1 | 0 | 0.5 | 0 | 0 | 0 | 0 | 0 | 0 | 0 | 0 |
| 392 | 0 | 0 | 0 | 0.45 | 0 | −1 | 0 | 0.55 | 0 | 0 | 0 | 0 | 0 | 0 | 0 | 0 |
| 393 | 0 | 0 | 0 | 0.4 | 0 | −1 | 0 | 0.6 | 0 | 0 | 0 | 0 | 0 | 0 | 0 | 0 |
| 394 | 0 | 0 | 0 | 0.35 | 0 | −1 | 0 | 0.65 | 0 | 0 | 0 | 0 | 0 | 0 | 0 | 0 |
| 395 | 0 | 0 | 0 | 0.3 | 0 | −1 | 0 | 0.7 | 0 | 0 | 0 | 0 | 0 | 0 | 0 | 0 |
| 396 | 0 | 0 | 0 | 0.25 | 0 | −1 | 0 | 0.75 | 0 | 0 | 0 | 0 | 0 | 0 | 0 | 0 |
| 397 | 0 | 0 | 0 | 0.2 | 0 | −1 | 0 | 0.8 | 0 | 0 | 0 | 0 | 0 | 0 | 0 | 0 |
| 398 | 0 | 0 | 0 | 0.15 | 0 | −1 | 0 | 0.85 | 0 | 0 | 0 | 0 | 0 | 0 | 0 | 0 |
| 399 | 0 | 0 | 0 | 0.1 | 0 | −1 | 0 | 0.9 | 0 | 0 | 0 | 0 | 0 | 0 | 0 | 0 |
| 400 | 0 | 0 | 0 | 0.05 | 0 | −1 | 0 | 0.95 | 0 | 0 | 0 | 0 | 0 | 0 | 0 | 0 |
| 401 | 0 | 0 | 0 | 0 | 0 | −1 | 0 | 1 | 0 | 0 | 0 | 0 | 0 | 0 | 0 | 0 |
| 402 | 0.05 | 0 | 0 | 0 | 0 | −1 | 0 | 0.95 | 0 | 0 | 0 | 0 | 0 | 0 | 0 | 0 |
| 403 | 0.1 | 0 | 0 | 0 | 0 | −1 | 0 | 0.9 | 0 | 0 | 0 | 0 | 0 | 0 | 0 | 0 |
| 404 | 0.15 | 0 | 0 | 0 | 0 | −1 | 0 | 0.85 | 0 | 0 | 0 | 0 | 0 | 0 | 0 | 0 |
| 405 | 0.2 | 0 | 0 | 0 | 0 | −1 | 0 | 0.8 | 0 | 0 | 0 | 0 | 0 | 0 | 0 | 0 |
| 406 | 0.25 | 0 | 0 | 0 | 0 | −1 | 0 | 0.75 | 0 | 0 | 0 | 0 | 0 | 0 | 0 | 0 |
| 407 | 0.3 | 0 | 0 | 0 | 0 | −1 | 0 | 0.7 | 0 | 0 | 0 | 0 | 0 | 0 | 0 | 0 |
| 408 | 0.35 | 0 | 0 | 0 | 0 | −1 | 0 | 0.65 | 0 | 0 | 0 | 0 | 0 | 0 | 0 | 0 |
| 409 | 0.4 | 0 | 0 | 0 | 0 | −1 | 0 | 0.6 | 0 | 0 | 0 | 0 | 0 | 0 | 0 | 0 |
| 410 | 0.45 | 0 | 0 | 0 | 0 | −1 | 0 | 0.55 | 0 | 0 | 0 | 0 | 0 | 0 | 0 | 0 |
| 411 | 0.5 | 0 | 0 | 0 | 0 | −1 | 0 | 0.5 | 0 | 0 | 0 | 0 | 0 | 0 | 0 | 0 |
| 412 | 0.55 | 0 | 0 | 0 | 0 | −1 | 0 | 0.45 | 0 | 0 | 0 | 0 | 0 | 0 | 0 | 0 |
| 413 | 0.6 | 0 | 0 | 0 | 0 | −1 | 0 | 0.4 | 0 | 0 | 0 | 0 | 0 | 0 | 0 | 0 |
| 414 | 0.65 | 0 | 0 | 0 | 0 | −1 | 0 | 0.35 | 0 | 0 | 0 | 0 | 0 | 0 | 0 | 0 |
| 415 | 0.7 | 0 | 0 | 0 | 0 | −1 | 0 | 0.3 | 0 | 0 | 0 | 0 | 0 | 0 | 0 | 0 |
| 416 | 0.75 | 0 | 0 | 0 | 0 | −1 | 0 | 0.25 | 0 | 0 | 0 | 0 | 0 | 0 | 0 | 0 |
| 417 | 0.8 | 0 | 0 | 0 | 0 | −1 | 0 | 0.2 | 0 | 0 | 0 | 0 | 0 | 0 | 0 | 0 |
| 418 | 0.85 | 0 | 0 | 0 | 0 | −1 | 0 | 0.15 | 0 | 0 | 0 | 0 | 0 | 0 | 0 | 0 |
| 419 | 0.9 | 0 | 0 | 0 | 0 | −1 | 0 | 0.1 | 0 | 0 | 0 | 0 | 0 | 0 | 0 | 0 |
| 420 | 0.95 | 0 | 0 | 0 | 0 | −1 | 0 | 0.05 | 0 | 0 | 0 | 0 | 0 | 0 | 0 | 0 |
| 421 | 1 | 0 | 0 | 0 | 0 | −1 | 0 | 0 | 0 | 0 | 0 | 0 | 0 | 0 | 0 | 0 |
| 422 | 0.95 | 0 | 0 | 0.05 | 0 | −0.95 | −0.05 | 0 | 0 | 0 | 0 | 0 | 0 | 0 | 0 | 0 |
| 423 | 0.9 | 0 | 0 | 0.1 | 0 | −0.9 | −0.1 | 0 | 0 | 0 | 0 | 0 | 0 | 0 | 0 | 0 |
| 424 | 0.85 | 0 | 0 | 0.15 | 0 | −0.85 | −0.15 | 0 | 0 | 0 | 0 | 0 | 0 | 0 | 0 | 0 |
| 425 | 0.8 | 0 | 0 | 0.2 | 0 | −0.8 | −0.2 | 0 | 0 | 0 | 0 | 0 | 0 | 0 | 0 | 0 |
| 426 | 0.75 | 0 | 0 | 0.25 | 0 | −0.75 | −0.25 | 0 | 0 | 0 | 0 | 0 | 0 | 0 | 0 | 0 |
| 427 | 0.7 | 0 | 0 | 0.3 | 0 | −0.7 | −0.3 | 0 | 0 | 0 | 0 | 0 | 0 | 0 | 0 | 0 |
| 428 | 0.65 | 0 | 0 | 0.35 | 0 | −0.65 | −0.35 | 0 | 0 | 0 | 0 | 0 | 0 | 0 | 0 | 0 |
| 429 | 0.6 | 0 | 0 | 0.4 | 0 | −0.6 | −0.4 | 0 | 0 | 0 | 0 | 0 | 0 | 0 | 0 | 0 |
| 430 | 0.55 | 0 | 0 | 0.45 | 0 | −0.55 | −0.45 | 0 | 0 | 0 | 0 | 0 | 0 | 0 | 0 | 0 |
| 431 | 0.5 | 0 | 0 | 0.5 | 0 | −0.5 | −0.5 | 0 | 0 | 0 | 0 | 0 | 0 | 0 | 0 | 0 |
| 432 | 0.45 | 0 | 0 | 0.55 | 0 | −0.45 | −0.55 | 0 | 0 | 0 | 0 | 0 | 0 | 0 | 0 | 0 |
| 433 | 0.4 | 0 | 0 | 0.6 | 0 | −0.4 | −0.6 | 0 | 0 | 0 | 0 | 0 | 0 | 0 | 0 | 0 |
| 434 | 0.35 | 0 | 0 | 0.65 | 0 | −0.35 | −0.65 | 0 | 0 | 0 | 0 | 0 | 0 | 0 | 0 | 0 |
| 435 | 0.3 | 0 | 0 | 0.7 | 0 | −0.3 | −0.7 | 0 | 0 | 0 | 0 | 0 | 0 | 0 | 0 | 0 |
| 436 | 0.25 | 0 | 0 | 0.75 | 0 | −0.25 | −0.75 | 0 | 0 | 0 | 0 | 0 | 0 | 0 | 0 | 0 |
| 437 | 0.2 | 0 | 0 | 0.8 | 0 | −0.2 | −0.8 | 0 | 0 | 0 | 0 | 0 | 0 | 0 | 0 | 0 |
| 438 | 0.15 | 0 | 0 | 0.85 | 0 | −0.15 | −0.85 | 0 | 0 | 0 | 0 | 0 | 0 | 0 | 0 | 0 |
| 439 | 0.1 | 0 | 0 | 0.9 | 0 | −0.1 | −0.9 | 0 | 0 | 0 | 0 | 0 | 0 | 0 | 0 | 0 |
| 440 | 0.05 | 0 | 0 | 0.95 | 0 | −0.05 | −0.95 | 0 | 0 | 0 | 0 | 0 | 0 | 0 | 0 | 0 |
| 441 | 0 | 0 | 0 | 1 | 0 | 0 | −1 | 0 | 0 | 0 | 0 | 0 | 0 | 0 | 0 | 0 |
| 442 | 0 | 0 | 0 | 0.95 | 0.05 | 0 | −1 | 0 | 0 | 0 | 0 | 0 | 0 | 0 | 0 | 0 |
| 443 | 0 | 0 | 0 | 0.9 | 0.1 | 0 | −1 | 0 | 0 | 0 | 0 | 0 | 0 | 0 | 0 | 0 |
| 444 | 0 | 0 | 0 | 0.85 | 0.15 | 0 | −1 | 0 | 0 | 0 | 0 | 0 | 0 | 0 | 0 | 0 |
| 445 | 0 | 0 | 0 | 0.8 | 0.2 | 0 | −1 | 0 | 0 | 0 | 0 | 0 | 0 | 0 | 0 | 0 |
| 446 | 0 | 0 | 0 | 0.75 | 0.25 | 0 | −1 | 0 | 0 | 0 | 0 | 0 | 0 | 0 | 0 | 0 |
| 447 | 0 | 0 | 0 | 0.7 | 0.3 | 0 | −1 | 0 | 0 | 0 | 0 | 0 | 0 | 0 | 0 | 0 |
| 448 | 0 | 0 | 0 | 0.65 | 0.35 | 0 | −1 | 0 | 0 | 0 | 0 | 0 | 0 | 0 | 0 | 0 |

APPENDIX A-continued

Simplified Steering Table

| Stim# | \multicolumn{16}{c}{Electrode#} | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| 449 | 0 | 0 | 0 | 0.6 | 0.4 | 0 | −1 | 0 | 0 | 0 | 0 | 0 | 0 | 0 | 0 | 0 |
| 450 | 0 | 0 | 0 | 0.55 | 0.45 | 0 | −1 | 0 | 0 | 0 | 0 | 0 | 0 | 0 | 0 | 0 |
| 451 | 0 | 0 | 0 | 0.5 | 0.5 | 0 | −1 | 0 | 0 | 0 | 0 | 0 | 0 | 0 | 0 | 0 |
| 452 | 0 | 0 | 0 | 0.45 | 0.55 | 0 | −1 | 0 | 0 | 0 | 0 | 0 | 0 | 0 | 0 | 0 |
| 453 | 0 | 0 | 0 | 0.4 | 0.6 | 0 | −1 | 0 | 0 | 0 | 0 | 0 | 0 | 0 | 0 | 0 |
| 454 | 0 | 0 | 0 | 0.35 | 0.65 | 0 | −1 | 0 | 0 | 0 | 0 | 0 | 0 | 0 | 0 | 0 |
| 455 | 0 | 0 | 0 | 0.3 | 0.7 | 0 | −1 | 0 | 0 | 0 | 0 | 0 | 0 | 0 | 0 | 0 |
| 456 | 0 | 0 | 0 | 0.25 | 0.75 | 0 | −1 | 0 | 0 | 0 | 0 | 0 | 0 | 0 | 0 | 0 |
| 457 | 0 | 0 | 0 | 0.2 | 0.8 | 0 | −1 | 0 | 0 | 0 | 0 | 0 | 0 | 0 | 0 | 0 |
| 458 | 0 | 0 | 0 | 0.15 | 0.85 | 0 | −1 | 0 | 0 | 0 | 0 | 0 | 0 | 0 | 0 | 0 |
| 459 | 0 | 0 | 0 | 0.1 | 0.9 | 0 | −1 | 0 | 0 | 0 | 0 | 0 | 0 | 0 | 0 | 0 |
| 460 | 0 | 0 | 0 | 0.05 | 0.95 | 0 | −1 | 0 | 0 | 0 | 0 | 0 | 0 | 0 | 0 | 0 |
| 461 | 0 | 0 | 0 | 0 | 1 | 0 | −1 | 0 | 0 | 0 | 0 | 0 | 0 | 0 | 0 | 0 |
| 462 | 0.05 | 0 | 0 | 0 | 0.95 | 0 | −1 | 0 | 0 | 0 | 0 | 0 | 0 | 0 | 0 | 0 |
| 463 | 0.1 | 0 | 0 | 0 | 0.9 | 0 | −1 | 0 | 0 | 0 | 0 | 0 | 0 | 0 | 0 | 0 |
| 464 | 0.15 | 0 | 0 | 0 | 0.85 | 0 | −1 | 0 | 0 | 0 | 0 | 0 | 0 | 0 | 0 | 0 |
| 465 | 0.2 | 0 | 0 | 0 | 0.8 | 0 | −1 | 0 | 0 | 0 | 0 | 0 | 0 | 0 | 0 | 0 |
| 466 | 0.25 | 0 | 0 | 0 | 0.75 | 0 | −1 | 0 | 0 | 0 | 0 | 0 | 0 | 0 | 0 | 0 |
| 467 | 0.3 | 0 | 0 | 0 | 0.7 | 0 | −1 | 0 | 0 | 0 | 0 | 0 | 0 | 0 | 0 | 0 |
| 468 | 0.35 | 0 | 0 | 0 | 0.65 | 0 | −1 | 0 | 0 | 0 | 0 | 0 | 0 | 0 | 0 | 0 |
| 469 | 0.4 | 0 | 0 | 0 | 0.6 | 0 | −1 | 0 | 0 | 0 | 0 | 0 | 0 | 0 | 0 | 0 |
| 470 | 0.45 | 0 | 0 | 0 | 0.55 | 0 | −1 | 0 | 0 | 0 | 0 | 0 | 0 | 0 | 0 | 0 |
| 471 | 0.5 | 0 | 0 | 0 | 0.5 | 0 | −1 | 0 | 0 | 0 | 0 | 0 | 0 | 0 | 0 | 0 |
| 472 | 0.55 | 0 | 0 | 0 | 0.45 | 0 | −1 | 0 | 0 | 0 | 0 | 0 | 0 | 0 | 0 | 0 |
| 473 | 0.6 | 0 | 0 | 0 | 0.4 | 0 | −1 | 0 | 0 | 0 | 0 | 0 | 0 | 0 | 0 | 0 |
| 474 | 0.65 | 0 | 0 | 0 | 0.35 | 0 | −1 | 0 | 0 | 0 | 0 | 0 | 0 | 0 | 0 | 0 |
| 475 | 0.7 | 0 | 0 | 0 | 0.3 | 0 | −1 | 0 | 0 | 0 | 0 | 0 | 0 | 0 | 0 | 0 |
| 476 | 0.75 | 0 | 0 | 0 | 0.25 | 0 | −1 | 0 | 0 | 0 | 0 | 0 | 0 | 0 | 0 | 0 |
| 477 | 0.8 | 0 | 0 | 0 | 0.2 | 0 | −1 | 0 | 0 | 0 | 0 | 0 | 0 | 0 | 0 | 0 |
| 478 | 0.85 | 0 | 0 | 0 | 0.15 | 0 | −1 | 0 | 0 | 0 | 0 | 0 | 0 | 0 | 0 | 0 |
| 479 | 0.9 | 0 | 0 | 0 | 0.1 | 0 | −1 | 0 | 0 | 0 | 0 | 0 | 0 | 0 | 0 | 0 |
| 480 | 0.95 | 0 | 0 | 0 | 0.05 | 0 | −1 | 0 | 0 | 0 | 0 | 0 | 0 | 0 | 0 | 0 |
| 481 | 1 | 0 | 0 | 0 | 0 | 0 | −1 | 0 | 0 | 0 | 0 | 0 | 0 | 0 | 0 | 0 |
| 482 | 0.95 | 0 | 0 | 0 | 0.05 | 0 | −0.95 | −0.05 | 0 | 0 | 0 | 0 | 0 | 0 | 0 | 0 |
| 483 | 0.9 | 0 | 0 | 0 | 0.1 | 0 | −0.9 | −0.1 | 0 | 0 | 0 | 0 | 0 | 0 | 0 | 0 |
| 484 | 0.85 | 0 | 0 | 0 | 0.15 | 0 | −0.85 | −0.15 | 0 | 0 | 0 | 0 | 0 | 0 | 0 | 0 |
| 485 | 0.8 | 0 | 0 | 0 | 0.2 | 0 | −0.8 | −0.2 | 0 | 0 | 0 | 0 | 0 | 0 | 0 | 0 |
| 486 | 0.75 | 0 | 0 | 0 | 0.25 | 0 | −0.75 | −0.25 | 0 | 0 | 0 | 0 | 0 | 0 | 0 | 0 |
| 487 | 0.7 | 0 | 0 | 0 | 0.3 | 0 | −0.7 | −0.3 | 0 | 0 | 0 | 0 | 0 | 0 | 0 | 0 |
| 488 | 0.65 | 0 | 0 | 0 | 0.35 | 0 | −0.65 | −0.35 | 0 | 0 | 0 | 0 | 0 | 0 | 0 | 0 |
| 489 | 0.6 | 0 | 0 | 0 | 0.4 | 0 | −0.6 | −0.4 | 0 | 0 | 0 | 0 | 0 | 0 | 0 | 0 |
| 490 | 0.55 | 0 | 0 | 0 | 0.45 | 0 | −0.55 | −0.45 | 0 | 0 | 0 | 0 | 0 | 0 | 0 | 0 |
| 491 | 0.5 | 0 | 0 | 0 | 0.5 | 0 | −0.5 | −0.5 | 0 | 0 | 0 | 0 | 0 | 0 | 0 | 0 |
| 492 | 0.45 | 0 | 0 | 0 | 0.55 | 0 | −0.45 | −0.55 | 0 | 0 | 0 | 0 | 0 | 0 | 0 | 0 |
| 493 | 0.4 | 0 | 0 | 0 | 0.6 | 0 | −0.4 | −0.6 | 0 | 0 | 0 | 0 | 0 | 0 | 0 | 0 |
| 494 | 0.35 | 0 | 0 | 0 | 0.65 | 0 | −0.5 | −0.5 | 0 | 0 | 0 | 0 | 0 | 0 | 0 | 0 |
| 495 | 0.3 | 0 | 0 | 0 | 0.7 | 0 | −0.45 | −0.55 | 0 | 0 | 0 | 0 | 0 | 0 | 0 | 0 |
| 496 | 0.25 | 0 | 0 | 0 | 0.75 | 0 | −0.4 | −0.6 | 0 | 0 | 0 | 0 | 0 | 0 | 0 | 0 |
| 497 | 0.2 | 0 | 0 | 0 | 0.8 | 0 | −0.35 | −0.65 | 0 | 0 | 0 | 0 | 0 | 0 | 0 | 0 |
| 498 | 0.15 | 0 | 0 | 0 | 0.85 | 0 | −0.3 | −0.7 | 0 | 0 | 0 | 0 | 0 | 0 | 0 | 0 |
| 499 | 0.1 | 0 | 0 | 0 | 0.9 | 0 | −0.25 | −0.75 | 0 | 0 | 0 | 0 | 0 | 0 | 0 | 0 |
| 500 | 0.50 | 0 | 0 | 0 | 0.95 | 0 | −0.2 | −0.8 | 0 | 0 | 0 | 0 | 0 | 0 | 0 | 0 |
| 501 | 0 | 0 | 0 | 0 | 1 | 0 | −0.15 | −0.85 | 0 | 0 | 0 | 0 | 0 | 0 | 0 | 0 |
| 502 | 0 | 0 | 0 | 0 | 0.95 | 0.05 | −0.1 | −0.9 | 0 | 0 | 0 | 0 | 0 | 0 | 0 | 0 |
| 503 | 0 | 0 | 0 | 0 | 0.9 | 0.1 | −0.05 | −0.95 | 0 | 0 | 0 | 0 | 0 | 0 | 0 | 0 |
| 504 | 0 | 0 | 0 | 0 | 0.85 | 0.15 | 0 | −1 | 0 | 0 | 0 | 0 | 0 | 0 | 0 | 0 |
| 505 | 0 | 0 | 0 | 0 | 0.8 | 0.2 | 0 | −1 | 0 | 0 | 0 | 0 | 0 | 0 | 0 | 0 |
| 506 | 0 | 0 | 0 | 0 | 0.75 | 0.25 | 0 | −1 | 0 | 0 | 0 | 0 | 0 | 0 | 0 | 0 |
| 507 | 0 | 0 | 0 | 0 | 0.7 | 0.3 | 0 | −1 | 0 | 0 | 0 | 0 | 0 | 0 | 0 | 0 |
| 508 | 0 | 0 | 0 | 0 | 0.65 | 0.35 | 0 | −1 | 0 | 0 | 0 | 0 | 0 | 0 | 0 | 0 |
| 509 | 0 | 0 | 0 | 0 | 0.6 | 0.4 | 0 | −1 | 0 | 0 | 0 | 0 | 0 | 0 | 0 | 0 |
| 510 | 0 | 0 | 0 | 0 | 0.55 | 0.45 | 0 | −1 | 0 | 0 | 0 | 0 | 0 | 0 | 0 | 0 |
| 511 | 0 | 0 | 0 | 0 | 0.5 | 0.5 | 0 | −1 | 0 | 0 | 0 | 0 | 0 | 0 | 0 | 0 |
| 512 | 0 | 0 | 0 | 0 | 0.45 | 0.55 | 0 | −1 | 0 | 0 | 0 | 0 | 0 | 0 | 0 | 0 |
| 513 | 0 | 0 | 0 | 0 | 0.4 | 0.6 | 0 | −1 | 0 | 0 | 0 | 0 | 0 | 0 | 0 | 0 |
| 514 | 0 | 0 | 0 | 0 | 0.35 | 0.65 | 0 | −1 | 0 | 0 | 0 | 0 | 0 | 0 | 0 | 0 |
| 515 | 0 | 0 | 0 | 0 | 0.3 | 0.7 | 0 | −0.1 | 0 | 0 | 0 | 0 | 0 | 0 | 0 | 0 |
| 516 | 0 | 0 | 0 | 0 | 0.25 | 0.75 | 0 | −1 | 0 | 0 | 0 | 0 | 0 | 0 | 0 | 0 |
| 517 | 0 | 0 | 0 | 0 | 0.2 | 0.8 | 0 | −1 | 0 | 0 | 0 | 0 | 0 | 0 | 0 | 0 |
| 518 | 0 | 0 | 0 | 0 | 0.15 | 0.85 | 0 | −1 | 0 | 0 | 0 | 0 | 0 | 0 | 0 | 0 |
| 519 | 0 | 0 | 0 | 0 | 0.1 | 0.9 | 0 | −1 | 0 | 0 | 0 | 0 | 0 | 0 | 0 | 0 |
| 520 | 0 | 0 | 0 | 0 | 0.05 | 0.95 | 0 | −1 | 0 | 0 | 0 | 0 | 0 | 0 | 0 | 0 |
| 521 | 0 | 0 | 0 | 0 | 0 | 1 | 0 | −1 | 0 | 0 | 0 | 0 | 0 | 0 | 0 | 0 |
| 522 | 0 | 0.05 | 0 | 0 | 0 | 0.95 | 0 | −1 | 0 | 0 | 0 | 0 | 0 | 0 | 0 | 0 |

APPENDIX A-continued

Simplified Steering Table

| Stim# | \multicolumn{16}{c}{Electrode#} |
|---|---|---|---|---|---|---|---|---|---|---|---|---|---|---|---|---|

| Stim# | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 523 | 0 | 0.1 | 0 | 0 | 0 | 0.9 | 0 | −1 | 0 | 0 | 0 | 0 | 0 | 0 | 0 | 0 |
| 524 | 0.05 | 0.1 | 0 | 0 | 0 | 0.85 | 0 | −1 | 0 | 0 | 0 | 0 | 0 | 0 | 0 | 0 |
| 525 | 0.1 | 0.1 | 0 | 0 | 0 | 0.8 | 0 | −1 | 0 | 0 | 0 | 0 | 0 | 0 | 0 | 0 |
| 526 | 0.1 | 0.15 | 0 | 0 | 0 | 0.75 | 0 | −1 | 0 | 0 | 0 | 0 | 0 | 0 | 0 | 0 |
| 527 | 0.1 | 0.2 | 0 | 0 | 0 | 0.7 | 0 | −1 | 0 | 0 | 0 | 0 | 0 | 0 | 0 | 0 |
| 528 | 0.15 | 0.2 | 0 | 0 | 0 | 0.65 | 0 | −1 | 0 | 0 | 0 | 0 | 0 | 0 | 0 | 0 |
| 529 | 0.2 | 0.2 | 0 | 0 | 0 | 0.6 | 0 | −1 | 0 | 0 | 0 | 0 | 0 | 0 | 0 | 0 |
| 530 | 0.2 | 0.25 | 0 | 0 | 0 | 0.55 | 0 | −1 | 0 | 0 | 0 | 0 | 0 | 0 | 0 | 0 |
| 531 | 0.2 | 0.3 | 0 | 0 | 0 | 0.5 | 0 | −1 | 0 | 0 | 0 | 0 | 0 | 0 | 0 | 0 |
| 532 | 0.25 | 0.3 | 0 | 0 | 0 | 0.45 | 0 | −1 | 0 | 0 | 0 | 0 | 0 | 0 | 0 | 0 |
| 533 | 0.3 | 0.3 | 0 | 0 | 0 | 0.4 | 0 | −1 | 0 | 0 | 0 | 0 | 0 | 0 | 0 | 0 |
| 534 | 0.3 | 0.35 | 0 | 0 | 0 | 0.35 | 0 | −1 | 0 | 0 | 0 | 0 | 0 | 0 | 0 | 0 |
| 535 | 0.3 | 0.4 | 0 | 0 | 0 | 0.3 | 0 | −1 | 0 | 0 | 0 | 0 | 0 | 0 | 0 | 0 |
| 536 | 0.35 | 0.4 | 0 | 0 | 0 | 0.25 | 0 | −1 | 0 | 0 | 0 | 0 | 0 | 0 | 0 | 0 |
| 537 | 0.4 | 0.4 | 0 | 0 | 0 | 0.2 | 0 | −1 | 0 | 0 | 0 | 0 | 0 | 0 | 0 | 0 |
| 538 | 0.4 | 0.45 | 0 | 0 | 0 | 0.15 | 0 | −1 | 0 | 0 | 0 | 0 | 0 | 0 | 0 | 0 |
| 539 | 0.4 | 0.5 | 0 | 0 | 0 | 0.1 | 0 | −1 | 0 | 0 | 0 | 0 | 0 | 0 | 0 | 0 |
| 540 | 0.45 | 0.5 | 0 | 0 | 0 | 0.05 | 0 | −1 | 0 | 0 | 0 | 0 | 0 | 0 | 0 | 0 |
| 541 | 0.5 | 0.5 | 0 | 0 | 0 | 0 | 0 | −1 | 0 | 0 | 0 | 0 | 0 | 0 | 0 | 0 |

What is claimed is:

1. A method of programming a controller that controls electrical stimulation energy output to a plurality of electrodes, the controller storing a set of programmed stimulation parameters associated with the plurality of electrodes, the method comprising:
  comparing the programmed stimulation parameter set with a plurality of sets of reference stimulation parameters, each of the reference sets of stimulation parameters being associated with the plurality of electrodes;
  determining if an identical match between the programmed stimulation parameter set and any one of the reference stimulation parameter sets exists based on the comparison;
  if an identical match exists, selecting the identically matched stimulation parameter set as an initial stimulation parameter set;
  if an identical match does not exist, determining a best fit between the programmed stimulation parameter set and the reference stimulation parameter sets and selecting the best fit stimulation parameter set as the initial stimulation parameter set;
  wherein the best fit determination comprises prioritizing the electrodes, and narrowing the reference stimulation parameter sets down to a single stimulation parameter set based on the electrode prioritization, wherein the single stimulation parameter set is selected as the initial stimulation parameter set; and
  programming the controller with a new set of programmable stimulation parameters based on the initial stimulation parameter set.

2. The method of claim 1, wherein the electrode prioritization is based on magnitudes of stimulation energy independently associated with the electrodes.

3. The method of claim 1, wherein the electrode prioritization is based on polarities independently associated with the electrodes.

4. The method of claim 1, wherein narrowing the reference stimulation parameter sets comprises initially determining a first set of the reference stimulation parameter sets that best match the programmable stimulation parameter set for the highest priority electrode, wherein the initial stimulation parameter set is selected from the first set of the reference stimulation parameter sets.

5. The method of claim 4, wherein narrowing the reference stimulation parameter sets further comprises determining a next set of reference stimulation parameter sets from the first set of the reference stimulation parameter sets that best match the programmed stimulation parameter set for the next highest priority electrode, and repeating this step until the single stimulation parameter set remains.

* * * * *